United States Patent
Dalchau et al.

(10) Patent No.: US 12,191,002 B2
(45) Date of Patent: Jan. 7, 2025

(54) DYNAMIC CHARACTERIZATION OF SYNTHETIC GENETIC CIRCUITS IN LIVING CELLS

(71) Applicant: Microsoft Technology Licensing, LLC, Redmond, WA (US)

(72) Inventors: Neil Dalchau, Cambridge (GB); Andrew Nicholas John Brojer Phillips, London (GB); Paul Grant, Cambridge (GB)

(73) Assignee: Microsoft Technology Licensing, LLC, Redmond, WA (US)

( * ) Notice: Subject to any disclaimer, the term of this patent is extended or adjusted under 35 U.S.C. 154(b) by 0 days.

(21) Appl. No.: 18/169,178

(22) Filed: Feb. 14, 2023

(65) Prior Publication Data
US 2023/0282303 A1    Sep. 7, 2023

Related U.S. Application Data

(63) Continuation of application No. 16/252,561, filed on Jan. 18, 2019, now Pat. No. 11,694,766.

(30) Foreign Application Priority Data
Jun. 28, 2018   (GB) .................................. 1810636.9

(51) Int. Cl.
| | | |
|---|---|---|
| G16B 5/30 | (2019.01) | |
| C12N 15/63 | (2006.01) | |
| G16B 5/00 | (2019.01) | |
| G16B 20/00 | (2019.01) | |
| G16B 25/00 | (2019.01) | |

(52) U.S. Cl.
CPC ............... G16B 5/30 (2019.02); C12N 15/63 (2013.01); G16B 5/00 (2019.02); G16B 20/00 (2019.02); G16B 25/00 (2019.02)

(58) Field of Classification Search
CPC . G16B 5/30; G16B 5/00; G16B 20/00; G16B 25/00; G16B 40/10; C12N 15/63
See application file for complete search history.

(56) References Cited

U.S. PATENT DOCUMENTS 11,694,766 B2 * 7/2023 Dalchau ................ G16B 40/10
                                                    702/19

OTHER PUBLICATIONS

Rudge et al., "Characterization of Intrinsic Properties of Promoters", ACS Synthetic Biology, vol. 5, No. 1, Jan. 7, 2016, pp. 89-98, XP55624758, ISSN: 2161-5063, DOI: 10.1021/acssynbio.5b00116 (Year: 2016).*
Communication under Rule 71(3) EPC Received for European Application No. 19735076.2, mailed on Feb. 15, 2024, 9 pages.

* cited by examiner

*Primary Examiner* — Tom Y Lu
(74) *Attorney, Agent, or Firm* — Barta Jones, PLLC

(57) ABSTRACT

The present invention relates to a method for determining one or more intrinsic properties of a DNA component from a plurality of measurements obtained over a time period from a cell culture, with each cell comprising the DNA component, wherein the DNA component is involved in transcription of one or more target signals, wherein the plurality of measurements comprises measurements relating to the density of the cell culture over the time period and measurements relating to the amount of the one or more target signals in the cell culture over the time period.

20 Claims, 36 Drawing Sheets

Ratiometric characterisation

HSL double receiver (R33-S175)

```
system doublereceiver
= {
|cells( )|
|CFP(P76,aCFP)
|YFP(P81,aYFP)
|LuxR(aR33)
|LasR(aS175)
}
```

HSL sender (Relay P76-LasI)

```
system relayP76LasI =
{
|cells( )|
|LuxR(aR33)
|LasR(aS175)
|CFP(P76,aCFP)
|YFP(P81,aYFP)
|LasI(P76)
}
```

Arabinose-inducible promoter (PBAD)

```
system pbad = {
  |cells( )|
  |YFP(PBad,aYFP_PB)
}
```

HSL degrader (AiiA)

```
system lactonase = {
  |cells( )|
  |LuxR(aR33)
  |LasR(aS175)
  |CFP(P76,aCFP)
  |YFP(P81,aYFP)
  |AiiA(PBad)
}
```

DYNAMIC CHARACTERIZATION OF SYNTHETIC GENETIC CIRCUITS IN LIVING CELLS

CROSS-REFERENCE TO RELATED APPLICATION

This application is a continuation application of and claims priority to U.S. patent application Ser. No. 16/252,561, entitled "DYNAMIC CHARACTERIZATION OF SYNTHETIC GENETIC CIRCUITS IN LIVING CELLS," filed on Jan. 18, 2019, which claims priority to GB Application No. 1810636.9, entitled "DYNAMIC CHARACTERIZATION OF SYNTHETIC GENETIC CIRCUITS IN LIVING CELLS," filed on Jun. 28, 2018, the disclosures of which are incorporated herein by reference in their entireties.

BACKGROUND

Synthetic biology includes designing and building artificial biological systems to aid in the investigation of how biological systems (and components of those systems) work, and to perform useful functions, such as the production of biological medicinal products or the conversion of waste material into valuable chemical products.

However, due to the complexity of biological systems, it has been difficult to establish methods that can be applied to characterise their components, which would then allow new systems with predictable behaviour to be designed. As such, a lot of effort has to be put into in vitro testing and modification of new systems in order to optimise them.

Generating an artificial biological system generally involves introducing a new genetic circuit into a host, such as a bacterial cell. The cell's innate machinery is then utilised to perform a new function based on the genetic circuit. Synthetic genetic circuits are constructed via genetic engineering from DNA-based components, e.g. protein coding, promoter and enhancer sequences etc. In general, the behaviour of these components in a living system is currently not predictable from their sequence. Additionally, quantitative characterisation is complicated by the activity of components depending on the concentration of regulators and the metabolic activity of the cell, both of which change over time. As such, when observing the performance of a particular genetic circuit in a cell, it is difficult to separate the intrinsic properties of the DNA-based component (e.g. the ability of a promoter to recruit polymerase) from extrinsic factors (e.g. cellular metabolic state, ribosome availability). Knowledge of the intrinsic properties of DNA-based components would be useful in the process of designing new genetic circuits with predictable behaviour.

Many methodologies have been developed in the past to infer parameters of ordinary differential equation (ODE) models of genetic component behaviour, but the majority of these methods do not take into account the metabolic state of the cell.

Recently it has been shown that variations in genetic circuit activity resulting from metabolic differences between cell cultures can be mitigated using so-called ratiometric methods. These methods divide the target output (e.g. produced protein) of a new genetic circuit under investigation, by the output of a constitutive control genetic circuit, whose activity depends on the metabolic state of the cell in an equivalent way to the target (Yordanov et al., ACS Synthetic Biology, 3(8):578-588, 2014; Rudge et al., ACS Synthetic Biology, 5(1):89-98, 2016). In particular, Yordanov et al., describe a computational method for automated characterisation of genetic components (ACS Synthetic Biology, 3(8) 3(8):578-588, 2014) which uses two fluorescent reporter signals, one to monitor the transcriptional activity of a target genetic circuit and another to monitor the activity of a control genetic circuit in which gene expression is under the control of a constitutive promoter. The authors directly combine the fluorescence signals into a single time-series, which is then mapped to a single quantity by averaging within a time window of interest. For example, while the cells are in exponential growth or alternatively in stationary phase.

However, these ratiometric methods rely on measurements during time windows in which activity of the genetic circuit is assumed to be constant. Therefore, these methods fail to capture dynamic behaviours.

Del Vecchio and colleagues created a library of genetic activation cascades in *E. coli* bacteria, in which they explicitly tune the resource demand of each gene, and show that resource competition shapes the response of genetic circuits (Qian et al., ACS Synth Biol. (2017); 6(7): 1263-1272).

Therefore, there remains a need for a method for characterising the intrinsic properties of genetic components of genetic circuits.

SUMMARY

According to one aspect the present invention provides a method for determining one or more intrinsic properties of a DNA component, from a plurality of measurements obtained over a time period from a cell culture, with each cell comprising the DNA component, wherein the DNA component is involved in transcription of one or more target signals, wherein the plurality of measurements comprises measurements relating to the density of the cell culture over the time period and measurements relating to the amount of the one or more target signals in the cell culture over the time period, the method comprising:

(a) estimating parameter values for a first mathematical model that describes cell culture density over time, by minimizing a measure of the difference between the first mathematical model output and the measurements relating to the density of the cell culture over the time period;

(b) estimating parameters quantifying the intrinsic properties of the DNA component, by embedding these parameters within a further mathematical model that describes the production of the one or more target signals over time, and by minimizing a measure of the difference between the model outputs and the measurements relating to the amount of the one or more target signals, wherein the further mathematical model additionally uses the parameter values estimated in (a) or parameter values based thereon.

The present invention improves on existing methods by providing a method that allows a DNA component, which is involved in transcription of one or more target signals in a synthetic genetic circuit, to be characterised dynamically. As a result, genetic circuits containing this DNA component can be designed and optimised in silico before having to be prepared in vitro, leading to time and cost savings.

In a further aspect, the present invention provides a computer program product embodied on a computer readable storage and comprising code which is configured so as to perform the operations of the above-described method when run on a computer system.

In a still further aspect, the present invention provides a method of optimizing expression of at least one gene comprised in a genetic circuit, wherein the genetic circuit further comprises a DNA component which is involved in transcription of the at least one gene, wherein the method comprises: (1) determining one or more intrinsic properties of the DNA component using the method described above; (2) using the one or more intrinsic properties of the DNA component determined in (1) to simulate expression of the at least one gene from the genetic circuit in at least two different arrangements of the genetic circuit; (3) selecting the arrangement in (2) that results in optimal expression of the at least one gene; and (4) making the arrangement of the genetic circuit selected in step (3).

BRIEF DESCRIPTION OF THE DRAWINGS

To assist understanding of the present disclosure and to show how it may be put into effect, reference is made, by way of example only, to the accompanying drawings in which:

FIG. 1A. Feedback loops between inserted genetic components and the growth and resources of the host cell are replaced with an open loop scheme that permits parameter identification. FIG. 1B. The parameter identification for each synthetic circuit comprises three inference problems, that can proceed sequentially or in parallel. Furthermore, characterisation of multiple circuits can be composed into a dependency graph, where circuits with common components can reuse parameters characterised previously. FIG. 1C. The computational graph of panel FIG. 1B can be condensed.

FIG. 2A. The $P_{Las}$-LuxI relay device, with double reporter. FIG. 2B. The $P_{Lux}$-LasI device, with double reporter.

FIG. 4A. Feedback loops between inserted genetic components and the growth and resources of the host cell are replaced with an open loop scheme that permits parameter identification. FIG. 4B. Flow diagrams illustrate connections between observation data (grey boxes) and parameter sets (circle nodes) for multiple circuits. FIG. 4C. Flow diagrams illustrate connections between observation data (grey boxes) and parameter sets (circle nodes) for multiple circuits. FIG. 4D. The computational graph of FIGS. 4B and 4C can be condensed.

FIG. 5A. Autofluorescence characterised with cells expressing no CFP or YFP, but measured at 480 nm and 530 nm in response to varying concentrations of EtOH. FIG. 5B. Fluorescent protein degradation characterised using CFP and YFP with a constitutive promoter. FIG. 5C. HSL double receiver characterised by measuring 4 variant circuits with different ribosome binding sites for LuxR and LasR expression and treated with C6-HSL or C12-HSL. FIG. 5D. HSL senders were characterised inducibly expressing LasI in response to different concentrations of C6-HSL via PLux76. FIG. 5E. The PBad promoter was characterised by inducing expression of YFP with different concentrations of arabinose. FIG. 5F. The HSL degrader, AiiA, was characterised by inducing its expression via PBad, then measuring the response of the double receiver to different concentrations of HSL.

FIG. 5G. CFP fluorescent measurements at varying nM concentrations of EtOH (in ten-fold dilutions starting from $1.7\times10^9$ nM) from autofluorescence characterization as per FIG. 5A. Upper bracket on right hand side represents grouping of lines of example measurements and model simulations from $1.7\times10^7$ to $1.7\times10^1$, $1.7\times10^{-1}$ and 0 nM EtOH. The lower two solid lines ending within this bracket are example measurements for $1.7\times10^8$ nM. Lower bracket: upper two dashed lines ending in this bracket represent model simulations for $1.7\times10^8$ nM. Lower bracket: lower two solid lines overlapping with dashed lines represent example measurements overlapping with model simulations for $1.7\times10^9$ nM. FIG. 5H. YFP fluorescent measurements at varying nM concentrations of EtOH (in ten-fold dilutions starting from $1.7\times10^9$ nM) from autofluorescence characterization as per FIG. 5A. Upper bracket on right hand side represents grouping of example measurements and model simulations from most of the EtOH concentrations. Lower bracket: upper pair of dashed lines represent model simulations for $1.7\times10^8$ nM. Lower bracket, lower dashed lines ending in this bracket represent model simulations for $1.7\times10^9$ nM, which track dots representing example measurements for $1.7\times10^9$ nM EtOH. FIG. 5I. CFP fluorescent measurements at varying μg/ml concentrations of chloramphenicol (5 μg/ml; 2.5 μg/ml; 1.25 μg/ml; 0.625 μg/ml; 0.1325 μg/ml; and 0 μg/ml) from standard promoter characterisation as per FIG. 5B. Lines ending in upper bracket on right hand are those representing example measurements and model simulations from 0 μg/ml, 0.1325 μg/ml, and 0.625 μg/ml. Lines ending in the lower bracket on the right hand side are those representing example measurements and model simulations from 1.25 μg/ml. Arrow points to solid and dashed lines from 5 μg/ml and 2.5 μg/ml which track along the bottom of the graph. FIG. 5J. YFP fluorescent measurements at varying μg/ml concentrations of chloramphenicol (5 μg/ml; 2.5 μg/ml; 1.25 μg/ml; 0.625 μg/ml; 0.1325 μg/ml; and 0 μg/ml) from standard promoter characterisation as per FIG. 5B. Top arrow points to example measurements from 1.25 μg/ml chloramphenicol. Lines ending in upper bracket are those representing example measurements and model simulations from 0 μg/ml, 0.1325 μg/ml, and 0.625 μg/ml. Dashed lines ending in lower bracket are those from model simulations from 1.25 μg/ml. Bottom arrow points to solid and dashed lines from 5 μg/ml and 2.5 μg/ml which track along the bottom of the graph. FIG. 5K. CFP fluorescent measurements at varying nM concentrations of C6 (25000 nM; 8333.3 nM; 2777.8 nM; 925.9 nM; 308.6 nM; 102.9 nM; 34.2 nM; 11.4 nM; 3.8 nM; 1.3 nM; 0.4 nM; and 0 nM) from HSL double receiver characterisation as per FIG. 5C. Top arrow points to solid lines generated by example measurements with 25000 nM (darker line) and 8333.3 nM (lighter line). Dashed lines ending in upper bracket represent lines generated by model simulations with 25000 nM (darker line) and 8333.3 nM (lighter line). Solid line ending in upper middle bracket, and dashed line ending directly beneath it relate to 925.9 nM C6. Solid line ending in middle bracket, and dashed line ending directly beneath it relate to 308.6 nM C6. Solid line ending in lower middle bracket, and dashed line ending directly beneath it relate to 102.9 nM C6. Lines ending in bottom bracket represent the concentrations beneath 102.9 nM C6. FIG. 5L. YFP fluorescent measurements at varying nM concentrations of C12 (25000 nM; 8333.3 nM; 2777.8 nM; 925.9 nM; 308.6 nM; 102.9 nM; 34.2 nM; 11.4 nM; 3.8 nM; 1.3 nM; 0.4 nM; and 0 nM) from HSL double receiver characterisation as per FIG. 5C. Lines ending in top bracket relate to 25000 nM, 8333.3 nM, 2777.8 nM, and 925.9 nM C12. Top arrow points to solid and dashed line from 308.6 nM C12. Upper middle arrow points to solid and dashed lines from 102.9 nM C12. Middle arrow points to solid and dashed lines from 34.3 nM C12. Lower middle arrow points to solid and dashed lines from 11.4 nM C12. Bottom arrow points to solid and dashed lines generated with all other concentrations. FIG. 5M. CFP fluorescent measurements at varying nM concentrations of C6 (25000 nM; 8333.3 nM; 2777.8 nM; 925.9 nM; 308.6 nM; 102.9 nM; 34.2 nM; 11.4 nM; 3.8 nM; 1.3 nM; 0.4 nM; and 0 nM) from HSL sender characterisation as per FIG. 5D. Lines ending in upper bracket are solid and dashed lines generated by 25000 nM and 8333.3 nM C6. Lines ending in upper middle bracket relate to 2777.8 nM and 925.9 nM C6. Lines ending in middle bracket relate to 308.6 nM C6. Lines ending in lower middle bracket relate to 102.9 nM C6. Solid and dashed lines ending in lower bracket are generated with the lower concentrations of C6. FIG. 5N. YFP fluorescent measurements at varying nM concentrations of C12 (25000 nM; 8333.3 nM; 2777.8 nM; 925.9 nM; 308.6 nM; 102.9 nM; 34.2 nM; 11.4 nM; 3.8 nM; 1.3 nM; 0.4 nM; and 0 nM) from HSL sender characterisation as per FIG. 5D. Dashed lines ending in upper bracket relate to 25000 nM, 8333.3 nM, 2777.8 nM, 925.9 nM, and 305.6 nM C12. Solid lines ending in middle bracket relate to 25000 nM, 8333.3 nM, 2777.8 nM, 925.9 nM, 305.6 nM, and 102.9 nM C12. The dashed line ending within this bracket relates to 102.9 nM C12. Dashed and solid lines at top arrow relate to 34.3 nM C12. Dashed and solid lines at bottom arrow relate to 11.4 nM C12. Lines generated by lower concentrations end within lower bracket. FIG. 5O. YFP fluorescent measurements at varying mM concentrations of arabinose (25 mM; 12.5 mM; 6.25 mM and 3.13 mM) from arabinose-inducible promoter characterisation as per FIG. 5E. Top arrow points to solid and dashed lines generated by 25 mM. Upper middle arrow points to solid and dashed lines generated by 12.5 mM. Lower middle arrow points to solid and dashed lines generated by 6.25 mM, and bottom arrow points to solid and dashed lines generated by 3.13 mM. FIG. 5P. CFP fluorescent measurements at varying mM concentrations of arabinose (5 mM; 2.5 mM; 1.25 mM, 0.625 mM, 0.3125 mM and 0 mM) from HSL degrader characterisation as per FIG. 5F. Top arrow points to solid line generated by 0.625 mM. Arrow second from top points to dashed line generated by 0.625 mM. Arrow third from top points to solid line generated by 0 mM. Arrow fourth from top points to dashed line generated by 0 mM. Arrow second from bottom points to dashed line generated by 2.5 mM. Bottom arrow points to solid line generated by 2.5 mM. FIG. 5Q. YFP fluorescent measurements at varying mM concentrations of arabinose (5 mM; 2.5 mM; 1.25 mM, 0.625 mM, 0.3125 mM and 0 mM) from HSL degrader characterisation as per FIG. 5F. Top arrow points to solid line generated by 1.25 mM. Arrow second from top points to dashed line generated by 1.25 mM. Arrow third from top points to dashed line generated by 0 mM. Arrow fourth from top points to solid line generated by 0 mM. Arrow second from bottom points to solid and dashed lines generated by 0.3125 mM. Bottom arrow points to solid and dashed lines generated by 2.5 mM.

FIG. 7E. HSL treatment: $C_6=25000$ nM. Thick line and thin line within region b are YFP data and model lines—overlapping and not distinguishable from each other on this graph. FIG. 7F. HSL treatment: $C_6=5000$ nM. Thick line and thin line within region b are YFP data and model lines—overlapping and not distinguishable from each other on this graph. FIG. 7G. HSL treatment: $C_6=1000$ nM. Thick line and thin line within region b are YFP data and model lines—overlapping and not distinguishable from each other on this graph. FIG. 7H. HSL treatment: $C_6=200$ nM. Thick line and thin line within region b are YFP data and model lines—overlapping and not distinguishable from each other on this graph. FIG. 7I. HSL treatment: $C_6=40$ nM. Thick line and thin line within region b are YFP data and model lines—overlapping and not distinguishable from each other on this graph. FIG. 7J. HSL treatment: $C_6=8$ nM. Arrow a indicates CFP thick and thin lines—overlapping and not distinguishable from each other on this graph. Arrow b indicates YFP thick and thin lines—overlapping and not distinguishable from each other on this graph.

FIG. 7K. HSL treatment: $C_{12}=25000$ nM. FIG. 7L. HSL treatment: $C_{12}=5000$ nM. Thick line and thin line within region a are CFP data and model lines—overlapping and not distinguishable from each other on this graph. FIG. 7M. HSL treatment: $C_{12}=1000$ nM. Thick line and thin line within region a are CFP data and model lines—overlapping and not distinguishable from each other on this graph. FIG. 7N. HSL treatment: $C_{12}=200$ nM. Thick line and thin line within region a are CFP data and model lines—overlapping and not distinguishable from each other on this graph. FIG. 7O. HSL treatment: $C_{12}=40$ nM. Thick line and thin line within region a are CFP data and model lines—overlapping and not distinguishable from each other on this graph. FIG. 7P. HSL treatment: $C_{12}=8$ nM. Arrow a indicates YFP solid line and arrow b indicates CFP solid line.

FIG. 12A. The $P_{OLas}$-LuxI relay device, with double reporter. FIG. 12B. The $P_{OLux}$-LasI device, with double reporter.

DETAILED DESCRIPTION

Figure 1A:
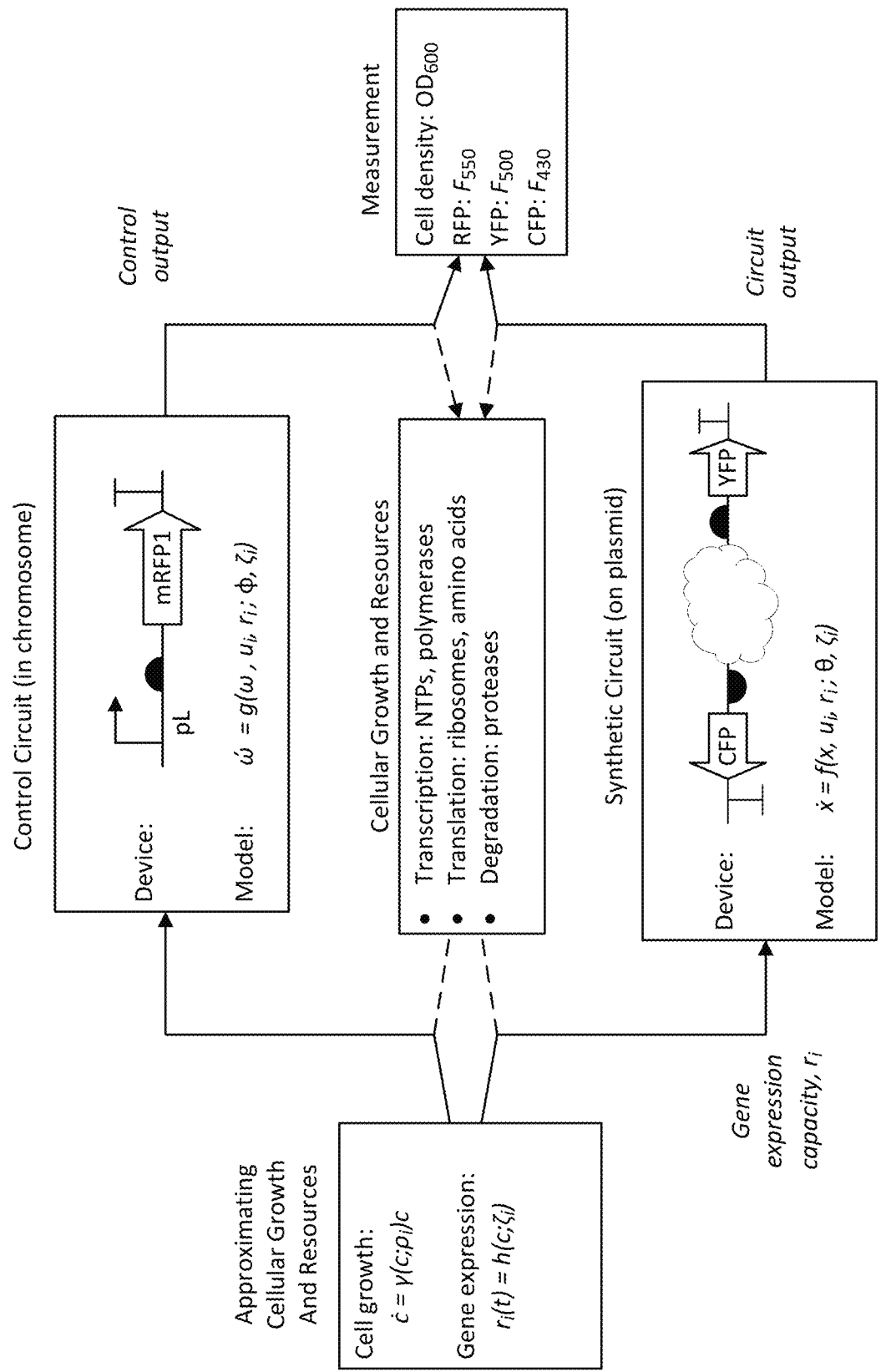
FIGS. 1A, 1B and 1C show diagrams to visually depict an example of a ratiometric method according to the invention.

As discussed above, the present invention provides a method for determining one or more intrinsic properties of a DNA component, from a plurality of measurements obtained over a time period from a cell culture, with each cell comprising the DNA component, wherein the DNA component is involved in transcription of one or more target signals, wherein the plurality of measurements comprises measurements relating to the density of the cell culture over the time period and measurements relating to the amount of the one or more target signals in the cell culture over the time period, the method comprising:
(a) estimating parameter values for a first mathematical model that describes cell culture density over time, by minimizing a measure of the difference between the first mathematical model output and the measurements relating to the density of the cell culture over the time period;
(b) estimating parameters quantifying the intrinsic properties of the DNA component, by embedding these parameters within a further mathematical model that describes the production of the one or more target signals over time, and by minimizing a measure of the difference between the model outputs and the measurements relating to the amount of the one or more target signals, wherein the further mathematical model additionally uses the parameter values estimated in (a) or parameter values based thereon.

The method can be used to characterise one or more intrinsic properties of a DNA component which is involved in transcription. In an expression system, such as in the situation where the DNA component is a promoter driving expression of a gene in a bacterial cell culture, the level of gene transcription will depend not only on the nature of the DNA component itself, but also on external (or extrinsic) factors such as availability of the cell's transcription machinery or even DNA sequences local to the DNA component. In the context of the present invention intrinsic properties of the DNA component are those that arise from the DNA component itself. In particular, intrinsic properties are those that result from the sequence of the DNA component, any modifications of the DNA component (such as methylation), and any 3D structure of the DNA component. The DNA component may be a regulatory sequence which is capable of regulating transcription of a gene. The DNA component can be a promoter or an enhancer. An intrinsic property of such a component may be the ability of the component to recruit polymerase, to bind transcription factors, or to regulate the transcriptional product of a gene.

In an embodiment, the method further comprises obtaining the measurements referred to above by culturing cells comprising the DNA component and taking the measurements over the time period.

The method comprises the use of a plurality of measurements obtained over a time period from a cell culture (or cell colony), wherein each cell comprises the DNA component. The DNA component is involved in transcription of one or more target signals. In particular, the DNA component is part of a genetic circuit from which the one or more target signals are transcribed. This genetic circuits can be integrated in the chromosomes of the cells of the culture. Alternatively, this genetic circuit can be on separate genetic elements such as plasmids, bacteriophage, cosmids, bacterial artificial chromosomes, yeast artificial chromosomes or mammalian artificial chromosomes. In particular, the genetic circuit can be on a plasmid. The copy number of the genetic circuit comprising the DNA component may be known or unknown.

The one or more target signals may be RNA or protein signals. In particular, it is desirable for the level of the one or more target signal to be measured repeatedly over the time period without significantly interfering with or disrupting the growth of the cell culture. Where the one or more target signals are RNA they may be measured by e.g. RNAseq technology. Where the one or more target signals are proteins they can be measured in other ways. For example, the target signal may be one or more luminescent or fluorescent proteins. Preferably the one or more target signals are different fluorescent proteins (e.g. green, yellow, red, or cyan fluorescent proteins—GFP, YFP, RFP and CFP, respectively) and the measurements relating to the amount of the one or more target signals in the cell culture over the time period in the method are measurements of the amount of fluorescence at a particular wavelength corresponding to the type of fluorescent protein being used. In an example, the one or more target signals are selected from yellow fluorescent protein (YFP), cyan fluorescent protein (CFP) and red fluorescent protein (RFP).

In the detailed description below the method is formulated with reference to specific target signals, i.e. RFP, CFP and YFP. However, it will be appreciated that other target signals can be used in these more detailed methods and equations.

In a preferred embodiment of the invention a non-linear observer process is used to compare the mathematical models with the measurements obtained from each cell culture. In particular, these measurements are usually cell-aggregated measurements that relate to the whole cell culture. For example, where measurements relate to the amount of fluorescence at a particular wavelength from a particular well of a microtitre plate, this is the fluorescence of the whole colony/culture within that well and therefore correspond to a cell-aggregated measure. However, the models describing the production of target signals (or other signals referred to herein) preferably describe intracellular interactions and therefore intracellular concentrations. Therefore, to compare the models with the bulk fluorescence data, a non-linear observer process is used.

For example, where the signals are CFP and YFP, for each wavelength w, bulk fluorescent variables can be described as $$B_{480}=([CFP]+[F_{480}]) \times c + B^{back}_{480}$$

$$B_{530}=([YFP]+[F_{530}]) \times c + B^{back}_{530}$$

where $[F_w]$ is the per-cell autofluorescence at wavelength w, c is cell density, and $B^{back}_w$ is the constant background fluorescence at wavelength w.

The cell culture (or colony) can be a culture of eukaryotic or prokaryotic cells. In particular, the cells can be bacterial, mammalian or yeast cells. In one example the cells are *E. coli* cells or CHO cells.

The measurements relating to the density of the cell culture over the time period can be any measurement which reflects cell culture density. Suitable ways of measuring cell culture density are known in the art. However, it is most convenient to measure the optical densities of the cell culture over the time period, in particular, measurements at a wavelength of 600 nm, i.e. $OD_{600}$.

The length of the time period is not particularly limited but should be long enough to cover the cell culture growth phases of interest, e.g. one or more of the lag phase, the exponential phase, the stationary phase and the death phase. Preferably the time period covers at least the exponential phase. During the time period measurements are taken at regular time intervals, which will depend on the speed of cell culture growth, usually every 5 to 20 minutes, or every 10 to 15 minutes. Preferably the measurements are taken as frequently as possible. In reality this depends on what the machine set up allows.

The method may be performed with a single cell culture. However, preferably it is performed with measurements from a plurality of separate cell cultures, each being subjected to different culture conditions, i.e. different external conditions. These conditions may be relevant to transcription (and optionally also translation) of the one or more target signals, e.g. the presence or absence of different nutrients or different concentrations of nutrients, etc. As described further below, variations in cell behaviour between the plurality of separate cell cultures (e.g. wells of a microtitre plate) that have been subjected to different conditions, can be quantified using the measurements and the model described herein. These variations can be used to factor out assumedly equivalent variations in the functioning of the gene circuit comprising the DNA component and the one or more target signals, so as to establish the intrinsic properties of the DNA component.

In particular, the plurality of cultures should be grown in separate compartments. For example, the plurality of cell cultures may be grown in different wells of a microtitre plate. In this regard, the description below may refer to "well-specific" properties. However, it will be appreciated that other containers or compartments may be used to grow the separate cell cultures.

The measurements obtained from the cell culture or plurality of cell cultures are used in order to quantify the one or more intrinsic properties of the DNA component. In particular, these are: measurements relating to the density of the cell culture over the time period and measurements relating to the amount of one or more target signals in the cell culture over the time period. In one aspect of this method of the invention, which is described further below, the measurements also include measurements relating to the amount of a reference signal in the cell culture over the time period.

The parts of the method can be performed separately, simultaneously or sequentially. In particular, it is not necessary for part (a) to have been completed for all measurements before (b) is started.

Similarly, the method refers to a first mathematical model and a further mathematical model (which, as described below, can be designated as the third mathematical model). However, the designations "first", and "further" are arbitrary designations for ease of reference and are not intended to imply any order of use. Moreover, the first and further mathematical models may be separate models or parts of a single model.

In one example of the method of this aspect of the invention, the measurements may be ones obtained from a cell culture in which each cell further comprises a reference promoter that initiates transcription of a reference signal; wherein the plurality of measurements of the method further comprises measurements relating to the amount of the reference signal in the cell culture over the time period; wherein the method further comprises estimating parameter values for a second mathematical model that describes the capacity of the cell culture to produce the reference signal over time, by minimizing a measure of the difference between the second mathematical model output and the measurements relating to the amount of the reference signal in the cell culture over the time period, wherein the second mathematical model additionally uses the parameter values estimated in (a); and the further mathematical model being a third mathematical model, wherein said additional use of parameter values comprises using the parameter values estimated based on (a) by the second mathematical model, taking the second mathematical model to provide an estimate of the capacity of the cell culture to produce the one or more target signals over time.

In particular, in this example the method may be regarded as a method for determining one or more intrinsic properties of a DNA component, from a plurality of measurements obtained over a time period from a cell culture, with each cell comprising the DNA component and a reference promoter, wherein the DNA component is involved in transcription of one or more target signals and the reference promoter initiates transcription of a reference signal, wherein the plurality of measurements comprises: (i) measurements relating to the density of the cell culture over the time period; (ii) measurements relating to the amount of the reference signal in the cell culture over the time period; and (iii) measurements relating to the amount of the one or more target signals in the cell culture over the time period, the method comprising:

(1) estimating parameter values for a first mathematical model that describes cell culture density over time, by minimizing a measure of the difference between the first mathematical model output and the measurements relating to the density of the cell culture over the time period;

(2) estimating parameter values for a second mathematical model that describes the capacity of the cell culture to produce the reference signal over time, by minimizing a measure of the difference between the second mathematical model output and the measurements relating to the amount of the reference signal in the cell culture over the time period, wherein the second mathematical model additionally uses the parameter values estimated in (1);

(3) estimating parameters quantifying the intrinsic properties of the DNA component, by embedding these parameters within a third mathematical model that describes the production of the one or more target signals over time, and by minimizing a measure of the difference between the model outputs and the measurements relating to the amount of the one or more target signals, wherein the third mathematical model additionally uses the parameter values estimated in (2) by taking the second mathematical model to provide an estimate of the capacity of the cell culture to produce the one or more target signals over time.

In an embodiment, the method further comprises obtaining the measurements referred to above by culturing cells comprising the DNA component and the reference promoter, and taking measurements (i), (ii) and (iii) over the time period.

The method comprises the use of a plurality of measurements obtained over a time period from a cell culture (or cell colony), wherein each cell comprises the DNA component. The DNA component is involved in transcription of one or more target signals and the reference promoter initiates/regulates transcription of a reference signal. In particular, the DNA component is part of a genetic circuit from which the one or more target signals are transcribed. The reference promoter is part of a genetic circuit from which the reference signal is transcribed. These genetic circuits can be integrated in the chromosomes of the cells of the culture. Alternatively, these genetic circuits can be on separate genetic elements such as plasmids, bacteriophage, cosmids, bacterial artificial chromosomes, yeast artificial chromosomes or mammalian artificial chromosomes. In particular, the genetic circuits can be on one or more plasmids. In one example the genetic circuit comprising the reference promoter ("the control circuit" as shown in FIG. 1A) is integrated in a chromosome, whereas the genetic circuit comprising the DNA component (the "synthetic circuit" as shown in FIG. 1A) is on a plasmid. Most preferably the genetic circuit of the reference promoter is chromosomally integrated or is on the same plasmid as the genetic circuit of the DNA component.

The copy number of the genetic circuit comprising the DNA component and the copy number of the genetic circuit comprising the reference promoter may be known. The genetic circuit comprising the DNA component and the genetic circuit comprising the reference promoter may be on the same extra chromosomal element, e.g. the same plasmid.

The one or more target signals and the reference signal may be RNA or protein signals. It is desirable for the level of the one or more target signal and the reference signal to be measured repeatedly over the time period without significantly interfering with or disrupting the growth of the cell culture. Where the one or more target signals and the reference signal are RNA they may be measured by e.g. RNAseq technology. Where the one or more target signals and reference signals are proteins they can be measured in other ways. For example, the target signal and the reporter signal may be one or more luminescent or fluorescent proteins. Preferably the one or more target signals and the reporter signal are different fluorescent proteins (e.g. green, yellow, red, or cyan fluorescent proteins—GFP, YFP, RFP and CFP, respectively) and the measurements of (ii) and (iii) in the method are measurements of the amount of fluorescence at a particular wavelength corresponding to the type of fluorescent protein being used. In a preferred example, the target signal is yellow fluorescent protein (YFP) and the reference signal is red fluorescent protein (RFP).

In particular, the reference promoter and reference signal are chosen to capture the same external factors that influence transcription (and translation if the signals are protein signals) of the one or more target signals, i.e. such that the activity of the genetic circuit comprising the reference promoter and reference signal depends on the metabolic state of the cell in an equivalent way to the genetic circuit comprising the DNA component and the one or more target signals. The reference promoter may be a constitutive promoter.

The cell culture (or colony) can be a culture of eukaryotic or prokaryotic cells. In particular, the cells can be bacterial, mammalian or yeast cells. Preferably the cells are *E. coli* cells or CHO cells.

The measurements relating to the density of the cell culture over the time period can be any measurement which reflects cell culture density. Suitable ways of measuring cell culture density are known in the art. However, it is most convenient to measure the optical densities of the cell culture over the time period, in particular, measurements at a wavelength of 600 nm, i.e. $OD_{600}$.

The length of the time period is not particularly limited but should be long enough to cover the cell culture growth phases of interest, e.g. one or more of the lag phase, the exponential phase, the stationary phase and the death phase. Preferably the time period covers at least the exponential phase. During the time period measurements are taken at regular time intervals, which will depend on the speed of cell culture growth, usually every 5 to 20 minutes, and preferably around every 10 to 15 minutes.

The method may be performed with a single cell culture. However, preferably it is performed with measurements from a plurality of separate cell cultures, each being subjected to different culture conditions, i.e. different external conditions. These conditions may be relevant to transcription (and optionally also translation) of the one or more target signals and the reference signal, e.g. the presence or absence of different nutrients or different concentrations of nutrients, etc. As described further below, variations in cell behaviour between the plurality of separate cell cultures (e.g. wells of a microtitre plate) that have been subjected to different conditions, can be quantified using the measurements and the model (that describes the capacity of the cell culture to produce of the reference signal). These variations can be used to factor out assumedly equivalent variations in the functioning of the gene circuit comprising the DNA component and the one or more target signals, so as to establish the intrinsic properties of the DNA component.

In particular, the plurality of cultures should be grown in separate compartments. For example, the plurality of cell cultures may be grown in different wells of a microtitre plate. In this regard, the description below may refer to "well-specific" properties. However, it will be appreciated that other containers or compartments may be used to grow the separate cell cultures.

The measurements (i), (ii) and (iii) obtained from the cell culture or plurality of cell cultures are used in order to quantify the one or more intrinsic properties of the DNA component. The parts of the method using these measurements are indicated as (1), (2) and (3). These parts can be performed separately, simultaneously or sequentially. In particular, it is not necessary for (1) and (2) to have been completed for all measurements before (3) is started.

Similarly, (1), (2) and (3) of the method refer to a first mathematical model, a second mathematical model and a third mathematical model respectively. However, the designations "first", "second" and "third" are arbitrary designations for ease of reference and are not intended to imply any order of use. Moreover, the first, second and third mathematical models may be separate models or parts of a single model.

FIGS. 1A to C and 4A to D provide graphical depictions of the characterisation methods of the present invention.

Figure 1B:
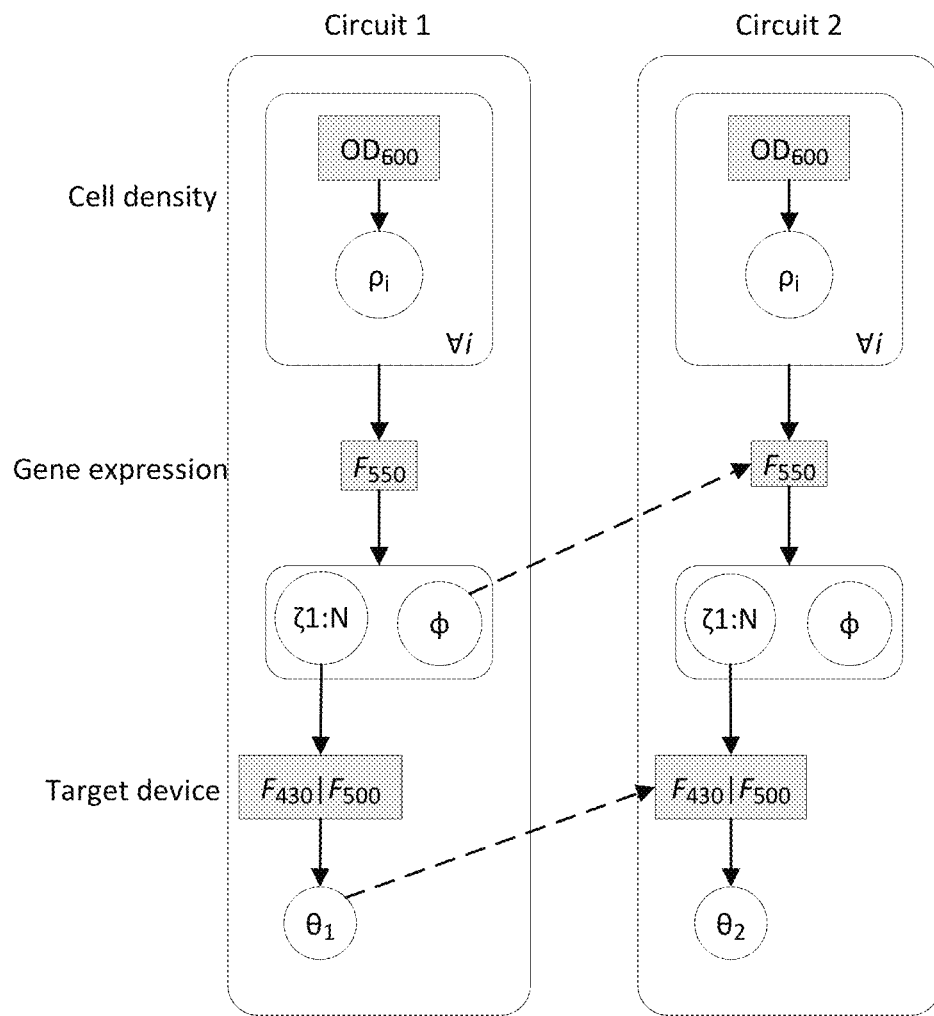
Figure 1C:
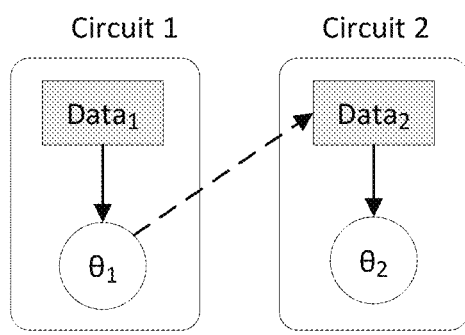

FIGS. 1A to C show a graphical depiction of ratiometric dynamic characterisation method as an example of an aspect of the invention. The method seeks to infer the quantitative properties of a synthetic circuit while accounting for the feedback of the synthetic circuit consuming cellular resources and inhibiting growth. To approximate this closed loop system, an open loop approximation is proposed, which is shown in FIG. 1A, that allows each cell culture i (expressing different circuits and/or experiencing different treatments) to have a model of cell growth ($\gamma$) and gene expression capacity (h) that are parameterized by circuit/condition-specific parameters ($\rho\_i$, $\xi_i$). The model of the synthetic circuit f therefore embeds these circuit-specific factors. A flow diagram shown in FIG. 1B illustrates connections between observation data (grey boxes) and parameter sets (circle nodes) for multiple circuits. For each condition i, cell growth parameters $\rho_i$ are inferred against $OD_{600}$ measurements. Next, gene expression capacity parameters are inferred against bulk fluorescence measurements of chromosomally integrated constitutive expression of mRFP1 ($F_{550}$), simultaneously for all conditions, to enable both circuit-specific ($\xi_i$) and circuit non-specific ($\phi$) parameters to be inferred. Finally, the parameters of the synthetic circuit are inferred against bulk fluorescence measurements of spectrally distinct fluorescent proteins (here ECFP and EYFP). If parameters of a model have been inferred previously, their marginal posteriors are propagated to the inference of the current circuit. This is indicated by the dashed arrows. As shown in FIG. 1C the computation graph of panel B can be condensed, but it should be noted that arbitrary acyclic graphs can be defined over the outlined procedure.

FIGS. 4A to D shows a further graphical depiction of the dynamic characterisation methods according to the invention. (A.) The method seeks to infer the quantitative properties of a synthetic circuit while accounting for the feedback of the synthetic circuit consuming cellular resources and inhibiting growth. To approximate this closed loop system, an open loop approximation is proposed that allows each cell culture i (expressing different circuits and/or experiencing different treatments) to be described by models of cell growth ($\gamma$) and gene expression capacity (h) that are parameterized by circuit/condition-specific parameters ($\rho_i$, $\xi_i$). The model of the circuit f therefore embeds these circuit-specific factors. (B,C.) A flow diagram illustrates connections between observation data (grey boxes) and parameter sets (circle nodes) for multiple circuits. For each condition i, cell growth parameters $\rho_i$ are inferred against $OD_{600}$ measurements. In ratiometric characterisation (panel C), gene expression capacity parameters are inferred against bulk fluorescence measurements of chromosomally integrated constitutive expression of mRFP1 ($F_{550}$), simultaneously for all conditions, to enable both circuit-specific ($\xi_i$) and circuit non-specific ($\phi$) parameters to be inferred. Finally, the parameters of the synthetic circuit are inferred against bulk fluorescence measurements of spectrally distinct fluorescent proteins (here ECFP and EYFP), and incorporate parameters for cell growth and for ratiometric characterisation. If parameters of a model have been inferred previously, their marginal posteriors are propagated to the inference of the current circuit. This is indicated by the dashed arrows. D. The computation graph of panels B and C can be condensed to indicate the dependency of multiple circuits more succinctly.

Cell Growth Characterisation/Cell Growth Phase

In (a) of the method the cell growth is characterised. In particular, parameter values are estimated for a first mathematical model that describes cell culture density over time, by minimizing a measure of the difference between the first mathematical model output and the measurements relating to density of the cell culture over the time period. Where the method is performed with measurements (e.g. measurements (i), (ii) and (iii)) obtained from a plurality of separate cell cultures, the growth of each cell culture is modelled separately (i.e. (a) is performed separately for each cell culture) to explicitly capture acceleration/deceleration of growth in response to variations in transcription activity and cell culture size in each culture.

Suitable mathematical models for characterising cell growth are known in the art. Preferably the model is the logistic cell growth model, more preferably the lag-logistic growth model.

The method of (a) may use an optimisation algorithm to minimize a measure of the difference between the first mathematical model output and the measurements relating to density of the cell culture over the time period. In particular, minimizing a measure of the difference in (a) may be minimizing a sum of squared errors or the absolute differences between the first mathematical model and the measurements relating to the density of the cell culture over the time period. Preferably the minimizing a measure of the difference in (a) uses a Nelder-Mead simplex algorithm.

In the description below the first mathematical model is the lag logistic growth model and the measurements relating to the density of the cell culture are optical density $OD_{600}$ measurements. Still further, the measurements of (i) comprise measurements relating to the cell density of a plurality of separate cell cultures over the time period grown in separate wells of a microtitre plate. These embodiments are preferred, however, it will be appreciated that (a) can be performed with other cell growth models, and with other measurements relating to the density of the cell culture. Moreover, containers other than microtitre plates can be used to grow the plurality of cell cultures.

The lag logistic growth model is described by:

$$\frac{dc}{dt} = \begin{cases} 0, & t < t_{lag} \\ rc\left(1 - \frac{c}{K}\right), & t \geq t_{lag} \end{cases}$$

where c is cell density, r is the per capita colony growth rate and K is the carrying capacity, which represents the maximum colony size. The time-evolution of this equation depends also on the initial cell density, $c^0 := c\ (t=0)$. In the measured $OD_{600}$ signal, there is non-cellular background signal, which is parameterized as a (plate-level) parameter $X_b$, which is shared by the separate cell cultures. Therefore, the time evolution of the OD signal of a single cell colony (e.g. in well i) is modelled as:

$$x_i(t) = \frac{K_i e^{r_i t} c_0}{K_i - c_i^0 + e^{r_i t} c_i^0} + x_b$$

where $r_i$, $K_i$, $C^0_i$ are the specific cell growth parameters of the cell colony in well i.

By assuming that the initial cell density is small, it can be taken that $X_i\ (0) \approx X_b$. Therefore, the parameter $X_b$ can be identified as the average over the first time point of the OD signal in each cell culture (e.g. in each well). This leaves the identification of the culture specific (e.g. well-specific) parameters as a set of inference problems in which we seek to minimize the sum of the square errors (SSE) between model and data for each well separately $$P_i^{OD} = \min_{\theta_i}\{SSE(\theta_i \mid OD)\}$$

where $\theta i = (r_i, K_i, c^0_i)$. For simple optimisation problems over few parameters, it is possible to obtain good performance (both reliability and efficiency) using direct search methods such as the Nelder-Mead simplex algorithm (Nelder et al., Computer Journal (1964); 7: 308-313). The implementation in MathNet.Numerics (http://numerics.mathdotnet.com/) can be used for cell growth characterisation.

Alternatively, the cell growth can be characterised by the lag logistic model as follows:

If $x_k$ is defined to be the measured signal corresponding to $OD_{600}$ at time-points $t_k$ (k=1, ... $n_r$), then this can be related to a model of cell growth described by c(t) according to $$x_k \sim \hat{x}(t_k) = c(t_k) + x_b$$

where $x_b$ is the background fluorescence and c represents Gaussian-distributed measurement noise with standard deviation σ.

To model cell density, the following general equation is used $$\frac{dc}{dt} = \gamma(c; \rho) \cdot c$$

where γ (c;ρ) is the specific growth rate function that is parameterized by ρ. For the lag-logistic model, γ is defined by $$\gamma(c, \rho) = \begin{cases} 0, & t < t_{lag} \\ r\left(1 - \frac{c}{K}\right), & t \geq t_{lag} \end{cases}$$

Here r is the per capita colony growth rate, K is the carrying capacity representing the maximum colony size and $t_{lag}$ is the duration of the lag phase of bacterial growth. Accordingly, the parameters of cell growth for colony i are given by $\rho_i = \{r_i, K_i, t_{lag,i}\}$. The time-evolution of c(t) depends also on the initial cell density, $c^0 := c(t\ 0)$, which is fixed to the intended dilution factor (0.2%) during preparation of the assay. In the measured $OD_{600}$ signal, there is a non-cellular background signal, which is parameterized as a plate-level shared parameter $x_b$. As a closed-form solution exists for the lag-logistic model, the time evolution of the OD signal in well i can simply be modelled as $$\hat{x}_i(t) = \frac{K_i e^{r_i(t-t_{lag})} c^0}{K_i - c^0 + e^{r_i(t-t_{lag})} c^0} + x_b$$

By assuming that the initial cell density is small, it can be taken that $c_i\ (0) \approx 0$, and so the background absorbance measurement will be approximately equal to the initial absorbance measurement. Therefore, the parameter $x_b$ is identified as the average over the first time point of the OD signal in each well. This leaves the identification of the well-specific parameters as a set of inference problems in which we seek to minimize the deviation between the data $(x_k)$ and simulation $(\hat{x}(t_k))$.

To obtain parameter estimates, it is assumed that the deviation between data and simulation is Gaussian-distributed with standard deviation σ. We seek to maximise the log-likelihood of producing the data in well i with parameters $\rho_i$ $$\max_{\rho_i}\{l(\rho_i)\}$$

where $l(\rho_i)$ is the sum of the log-probabilities of Gaussian observations for $x_k - \hat{x}_k(t_i)$, with variance $\sigma^2$. For simple optimisation problems over few parameters, it is possible to obtain good performance (both reliability and efficiency) using direct search methods such as the Nelder-Mead simplex algorithm (Nelder and Mead, The Computer Journal, 7(4):308-313, 1965). The implementation in MathNet.Numerics (http://numerics.mathdotnet.com/) can be used.

Characterisation of the Ratiometric Reference (Control) Signal/Control Phase

In a further part of the method parameter values are estimated for a second mathematical model that describes the capacity of the cell culture to produce the reference signal over time, by minimizing a measure of the difference between the second mathematical model output and the measurements relating to the amount of the reference signal in the at least one cell culture over the time period, wherein the second mathematical model additionally uses the parameter values estimated in (a).

In particular, the parametized first mathematical model from (a) can be used in in this part of the method to determine a time-dependent dilution rate for the cell culture (or for each cell culture of the plurality of cell cultures) as part of the second mathematical model.

The second mathematical model describes the capacity of the cell culture to produce the reference signal over time, which can then be taken or used as an estimate of the capacity of the cell culture to produce the one or more target signals over time, i.e. the second mathematical model can serve as a proxy for the ability of the cell culture to produce other gene expression products, such as the one or more target signals.

Preferably the second mathematical model models the reference signal as a chemical reaction network. The method of this part may use an optimisation algorithm to minimize a measure of the difference between the second mathematical model output and the measurements relating to the amount of the reference signal over the time period. In particular, minimizing a measure of the difference in this part may use a Markov chain Monte Carlo (MCMC) method, preferably a Metropolis-Hastings algorithm.

Where the method is performed with measurements (e.g. measurements (i), (ii) and (iii)) obtained from a plurality of separate cell cultures (subjected to different conditions), the capacity of each culture to produce the reference signal over time is modelled separately (i.e. this part is performed separately) for each cell culture. In this way variations between the different cell cultures can be quantified.

In the description below the reference signal is red fluorescent protein (RFP) and the measurements relating to the amount of reference signal in the cell culture are measurements of the level of RFP fluorescence. These embodiments are preferred; however, it will be appreciated that this part of the method can be performed with another reference signal, and with other related measurements of the level of the reporter signal.

In particular, in this part of the method the fluorescence signals from the RFP can be modelled directly as a chemical reaction network (CRN), and this parameterized model can be used to apply equivalent extrinsic variations to a model of the target fluorescence signal.

The model may utilise an open loop approximation and may not explicitly describe feedback of the gene circuit consuming cellular resources and inhibiting growth. In this regard, the model may include a description of DNA and RNA, or DNA, RNA and protein but exclude a specific description of the host cell machinery. For example, it may exclude a specific description of polymerases and/or ribosomes.

Specifically, constitutive production of RFP mRNA, followed by translation and fluorescent protein maturation can be described by the following CRN:

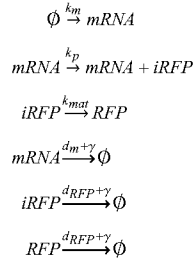

$$\emptyset \xrightarrow{k_m} mRNA$$

$$mRNA \xrightarrow{k_p} mRNA + iRFP$$

$$iRFP \xrightarrow{k_{mat}} RFP$$

$$mRNA \xrightarrow{d_m + \gamma} \emptyset$$

$$iRFP \xrightarrow{d_{RFP} + \gamma} \emptyset$$

$$RFP \xrightarrow{d_{RFP} + \gamma} \emptyset$$

where $k_m$, and pc are transcription, translation and maturation of RFP respectively, $\gamma$ is the rate of dilution, and $d_m$, $d_{RFP}$ are degradation rates of mRNA and (RFP) protein. Assuming mass action, the corresponding ordinary differential equations for the time evolution of the concentrations of each molecule can be written as:

$$\frac{d[mRNA]}{dt} = k_m - (d_m + \gamma)[mRNA]$$

$$\frac{d[iRFP]}{dt} = k_p[mRNA] - (d_{RFP} + \gamma + \mu_R)[iRFP]$$

$$\frac{d[RFP]}{dt} = \mu_R[iRFP] - (d_{RFP} + \gamma)[RFP]$$

Here, the effect of dilution is described as a quantity $\gamma^{(i)}$, where i denotes the particular colony being measured. This dilution term represents the decline in concentration as the volume of cells increases, and since the cell growth for each cell culture (e.g. each well) is characterised, the parameterized logistic model from step (a) can be used to determine an accurate time-dependent dilution rate for each cell culture (e.g. each well in the microtiter plate). In particular, for well i, the specific growth rate may be assigned as $\gamma^{(i)} = r_i(1 - c/K_i)$ (for $t \geq t_{lag}$, and 0 otherwise).

The dynamics of transcription and mRNA turnover are usually faster than translation and protein turnover, and therefore a separation of timescales argument can be applied to simplify the model equations (5). By assuming that the mRNA equation is in a quasi-equilibrium, equation 5a can be approximated as:

$$[mRNA]^* \approx \frac{k_m}{d_m + \gamma}$$

Accordingly, the simplified model can be updated. In addition, if the maturation time is faster than the turnover time for the fluorescent protein, then an even simpler model can be derived.

In order to describe measurements of a circuit exposed to different conditions, the model sets in which some parameters are sample-specific can be considered and inter-sample variations can be incorporated, while others are assumed to be fixed properties of the biochemistry. Accordingly, for a sample i, the simplified model of the reference (control) signal becomes $$\frac{d[RFP]^{(i)}}{dt} = k_c^{(i)} - (d_{RFP} + \gamma^{(i)})[RFP]^{(i)}$$

In this formulation, $k_c^{(i)}$ represents the gene expression capacity of the cells in sample i.

A sample specific $k_c$ enables the capture of differences in transcription, translation and mRNA degradation that arise from differences in the general state of the cells under their measured conditions. This might include an increased burden on the ribosome pool leading to lower translation (Gorochowski et al., ACS Synthetic Biology, 2014, 3 (3): 129-139; Ceroni et al., Nature Methods, 2015, 12(5): 415-418), increased burden on polymerases leading to lower transcription (Tan et al., Nature Chemical Biology, 2009, 5(11): 842-848), or differences in mRNA degradation of different mRNA sequences (Bouvet and Belasco, Nature, 1992, 360(6403): 488-491). Accordingly, these can include both intrinsic and extrinsic properties (Rudge et al., ACS Synthetic Biology, 2016, 5(1): 89-98) of gene circuits. By describing cell growth and gene expression rates with well-specific values, we can arbitrarily account for any interdependency between the two (Scott et al., Science, 2010, 330(6007): 1099-1102), despite not explicitly modelling the feedback process.

In principle, gene expression capacity could be any arbitrary time-dependent function, which could seek to describe the feedback from high circuit activity and therefore strong metabolic burden on cellular gene expression. But in practice, it is possible to make assumptions about the form of these functions, in order to make parameter inference tractable.

In particular, the assumption can be made that gene expression capacity switches between two values, $r_{exp}$ and $r_{stat}$, representing exponential and stationary phase growth. This implements the hypothesis that gene expression capacity will be generally higher during exponential phase, and transitions to a lower rate as the cell culture approaches its carrying capacity, and metabolism slows down. The OD measurements and logistic model can be used to define when the transition occurs, by defining a critical colony density $K_c$. Putting this together, the function used can be defined as $$k_c^{(i)} = \frac{r_c^{(i)}[x]^{n_c} + r_s K_c^{n_c}}{[x]^{n_c} + K_c^{n_c}},$$

where $n_c$ determines how fast $K_c^{(i)}$ switches between $r_c^{(i)}$ and $r_s$.

Finally, it is important to note that uniform values of $r_s$, $k_c$ and $n_c$ are used to prevent overfitting.

The parameter inference problem can therefore be defined for this part of the method. For convenience, we define $\theta$ to be the vector of parameter values sought. For the switch hypothesis, values of $r_c^{(i)}$, $r_s$, $K_c$ and $n_c$ are sought to parameterise the switch function, in addition to the hypothesis-independent parameter $d_{RFP}$. Given estimates of the logistic growth parameters ($r^{(i)}$, $K^{(i)}$, $c_0^{(i)}$) for each measured cell culture obtained in (a), the parameters of the gene expression capacity function can be inferred by comparing RFP fluorescence measurements with simulations of the simplified model (Grant et al., Molecular Systems Biology, 2016, 12(1): 849-849). In contrast to the optimisation procedure in (a), as indicated above the Markov chain Monte Carlo (MCMC) methods are preferred for the optimisation procedure in (b). In particular, the Nelder-Mead algorithm was found to perform poorly for this inference problem, frequently getting stuck in sub-optimal global optima of the cost function. MCMC methods are able to reduce the impact of this problem. In practice, we found consistent convergence to single optimal regions in parameter space for each problem that we attempted.

The Metropolis-Hastings algorithm as implemented in the Filzbach software may be used to perform the MCMC parameterizations. This requires first specifying a likelihood function that evaluates the likelihood score for a candidate parameter set $\theta$. If we denote by $R_{i,1}, \ldots, R_{i,n}$ the RPF measurements of well i at time points $t_1, \ldots, t_n$, then the associated likelihood function can be defined as:

$$L(\theta) = \prod_{i=1}^{n_W} \prod_{j=1}^{n} \frac{1}{\sqrt{2\sigma}} \exp\left\{-\frac{([RFP]^{(i)}(t_j) - R_{i,j})^2}{2\sigma^2}\right\}$$

where $n_W$ is the number of wells.

As a variation to the above, gene expression capacity for a reference signal such as red fluorescent protein (RRP) can be modelled as follows:

Constitutive production of RFP mRNA, followed by translation and fluorescent protein maturation can be described by the following chemical reaction network:

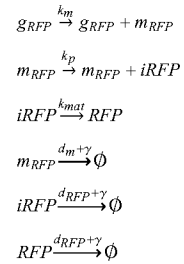

where $k_m$, $k_p$ and $k_{mat}$ ($\mu_R$) are transcription, translation and maturation of RFP respectively, $\gamma$ is the rate of dilution, and $d_m$, $d_{RFP}$ are degradation rates of mRNA and (RFP) protein.

From the reaction set of the above paragraph, corresponding ordinary differential equations for the time evolution of the concentrations of each molecule, assuming mass action kinetics can be written as $$\frac{d[m_{RFP}]}{dt} = k_m - (d_m + \gamma)[m_{RFP}]$$

$$\frac{d[iRFP]}{dt} = k_p[m_{RFP}] - (d_{RFP} + \gamma + \mu_R)[iRFP]$$

$$\frac{d[RFP]}{dt} = \mu_R[iRFP] - (d_{RFP} + \gamma)[RFP]$$

Here, the effect of dilution is described by the specific growth rate $\gamma$, from the following equation already shown above:

$$\gamma(c, \rho) = \begin{cases} 0, & t < t_{lag} \\ r\left(1 - \frac{c}{K}\right), & t \geq t_{lag} \end{cases}$$

This dilution term represents the decline in concentration as the volume of cells increases, and since the cell growth for each well is characterised, the parameterized logistic model can be used to determine an accurate time-dependent dilution rate for each well in the microtiter plate.

The dynamics of transcription and mRNA turnover are usually faster than translation and protein turnover, and therefore a separation of timescales argument can be applied to simplify the model equations (of the above paragraph) as $[m_{RFP}]^* \approx k_m/d_m + \gamma$. By further assuming that the mRNA dynamics are faster than dilution, the above expression becomes constant, and can be incorporated into a single quantity incorporating the mRNA equilibrium and the translation rate $k_p$. If the maturation time is faster than the turnover time for the fluorescent proteins, then an even simpler model can be derived:

$$\frac{d[RFP]_i}{dt} = a_{RFP} - (d_{RFP} - \gamma_i(c))[RFP]_i$$

where $\alpha_{RFP}$ incorporates transcription, translation, fluorescent protein maturation and mRNA degradation rates.

The reaction model above assumes a particular level of abstraction for describing the inserted biochemical components. Specifically, it enables the description of each component of the central dogma (DNA, RNA, protein) explicitly, but ignores host cell machinery (RNA polymerase, ribosomes, proteases, etc). In particular, an open loop analogue is parameterised. In the previous section regarding cell growth characterisation, it was shown that well-specific parameters can be used to describe well-specific growth curves. In essence, this is the first step towards an open loop system. When the synthetic circuit creates more burden on the cell, lower values of $r_i$ and $K_i$ will be observed.

A quantity $h_i(c; \xi_i)$ can be introduced which is a function of sample-specific parameters $\xi_i$ that quantifies the gene expression capacity of sample i such that all gene expression terms in the model are proportional to $h_i$. As the RFP measurements are used to parameterise $h_i$, $\alpha_{RFP}$ is exchanged for $h_i$ in the equation above, as it would not be possible to separate the two values if expressed as a product. As such, the values inferred for $h_i$ are in units of (mature) RFP molecules per unit time.

A sample-specific (enables differences in transcription, translation and mRNA degradation to be captured that arise from differences in the general state of the cells under their measured conditions. This might include an increased burden on the ribosome pool leading to lower translation, increased burden on polymerases leading to lower transcription, or differences in mRNA degradation of different mRNA sequences. Accordingly, these can include both intrinsic and extrinsic properties of synthetic gene circuits. By describing cell growth and gene expression rates with well-specific values, any interdependency between the two can be arbitrarily accounted for, despite not explicitly modelling the feedback process. In principle, gene expression capacity could be any arbitrary time-dependent function, which could seek to describe the feedback from high circuit activity and therefore strong metabolic burden on cellular gene expression. Here, several contrasting yet relatively simple assumptions are considered about the functional form of $h_i(c)$.

To generalize the description of the control phase, we describe the control circuit (from which the control/reference signal is produced) as $$\dot{x}_C = f_C(x_C, u_i, h_i; \phi, \xi_i)$$

$$y_C = g_C(x_C)$$

where $x_c$ is a vector of state variables that at least includes [RFP], $\mu_i$ are the treatments being applied to the circuit in well i, $h_i$ is the model of gene expression capacity as defined above, $\Phi$ are well-independent parameters and xi, are the parameters for $h_i(c)$.

Characterisation of the DNA Component—Target Phase

In this part of the method parameters quantifying the intrinsic properties of the DNA component are estimated, by embedding these parameters within a further mathematical model that describes the production of the one or more target signals over time, and by minimizing a measure of the difference between the model outputs and the measurements relating to the amount of the one or more target signals, wherein the further mathematical model additionally uses the parameter values estimated in (a) (i.e. cell growth characterisation) or parameter values based thereon. Where the further mathematical model uses parameter values estimated in (a) this is referred to as direct dynamic characterisation. Such a method does not seek to establish gene expression capacity based on a reference signal. In particular, where the method is performed with measurements from a plurality of cell cultures characterisation does not attempt to quantify between-culture variations in gene expression capacity.

Alternatively, the further mathematical model can be termed as the third mathematical model and use parameter values based on parameter values estimated for the first mathematical model. In one embodiment this means that the parameter values estimated for the first mathematical model are used in a second mathematical model which seeks to quantify overall gene expression capacity of the cell colony, as described in the section above. This further/third mathematical model uses the parameter values estimated using the second mathematical model by taking the second mathematical model to provide an estimate of the capacity of the cell culture to produce one or more target signals over time.

In this part of the method parameters quantifying the intrinsic properties of the DNA component are estimated, by embedding these parameters within a further/third mathematical model that describes the production of the one or more target signals over time, and by minimizing a measure of the difference between the model outputs and the measurements relating to the amount of the one or more target signals, wherein the third mathematical model additionally uses the parameter values estimated in the part of the method involving the second mathematical model by taking the second mathematical model to provide an estimate of the capacity of the cell culture to produce the one or more target signals over time.

As mentioned previously, the general idea of dynamic ratiometric characterisation is to use the measurements and model of the reference signal to quantify variations in cell behaviour between separate cell cultures (e.g. in wells of a microtiter plate), and use these to factor out assumedly equivalent variations in the functioning of the genetic circuit comprising the DNA component.

In the description below we describe the use of a genetic circuit in which the target signal is from yellow fluorescent protein and the measurements relating to the amount of the target signal is measurements of the level of YFP fluorescence. These embodiments are preferred, however, it will be appreciated that (c) can be performed with other target signals, and with other related measurements of the level of the target signal.

The simplest synthetic gene circuit involving constitutive expression of YFP can be considered first. For consistency, the same chemical reaction network model as for constitutive expression of the reference signal (equations 7 above) can be used, but with YFP-specific degradation and maturation parameters.

$$\frac{d[YFP]^{(i)}}{dt} = \rho_Y k_c^{(i)} - (d_{YFP} + \gamma^{(i)})[YFP]^{(i)} \quad (10)$$

As transcription, translation and mRNA degradation will differ between YFP and RFP, and to incorporate the same notion of ratiometric characterisation from before (Yordanov et al., ACS Synthetic Biology, 3(8):578-588, 2014; Rudge et al., ACS Synthetic Biology, 5(1):89-98, 2016), we consider the gene expression capacity of YFP to be proportional to the gene expression capacity of RFP, with a factor $\rho\gamma$.

Alternatively, the method involving the further/third mathematical model can be performed using the compact general formulation $$\dot{x}_T = f_T(x_T, u_i, h_i; \theta, \xi_i)$$

$$y_T = g_T(x_T)$$

Where x is a vector of state variables that at least includes variables for the intracellular concentration of each measured fluorescent protein and $\theta$ contains the global circuit parameters. For ratiometric dynamic characterisation, $h_i$ (c; $\xi_i$) is determined during the control phase (utilising measurements relating to the amount of one or more target signals), with the maximum likelihood estimates of $\xi_i$ used to simulate $f(x, u_i, h_i)$.

For direct dynamic characterisation, $h_i$ is simply set to be 1 throughout.

Inferring Parameters of ODE Models Using Markov Chain Monte Carlo

According to the invention, the Markov chain Monte Carlo (MCMC) methods can be used in either one or both of the parts of the method using the second or further/third mathematical models. In particular, in both of these parts of the method parameters are inferred for ordinary differential equation (ODE) models, given some observational data. It is preferred that these parts of the method do not use the Nelder-Mead algorithm.

MCMC methods also have the advantage of characterising the uncertainty of parameter estimates, which can arise from several sources: measurement error, process error (molecular stochasticity) and model misspecification.

For notational convenience, $\theta$ is defined to be the vector of parameter values sought. In particular, the Metropolis-Hastings algorithm as implemented in the Filzbach software (http://www.github.com/prediction machines/filzbach) can be used to perform the MCMC parameterizations. This requires specifying a function that evaluates the log-likelihood score for a candidate parameter set $\theta$, and prior distributions of each parameter, which encode prior belief of its plausible values.

Computing the log-likelihood. If we denote by $y_{w, i, j}$, the bulk fluorescence wavelengths w (w$\in$\{480,530,610\}) in well i (i=1, ..., $n_c$) at time-points $t_j$ (j=1, ..., $n_t$), then a likelihood function for wavelength w can be defined as $$L_w(\theta) = p(y_w | \theta) = \prod_i \prod_j \frac{1}{\sqrt{2\pi}\sigma} \exp\left\{-\frac{(B_w^{(i)}(t_j) - y_{w,i,j})^2}{2\sigma^2}\right\}$$

where $n_c$ is the number of colonies (e.g. wells in the 96-well plate). In the control phase, we simply use $L_{610}$ as the complete likelihood function, while in the target phase we use $L_{480} \times L_{530}$ when both CFP and YFP reporters are present in a circuit, and just one term otherwise. The parameter $\sigma$ describes the standard deviation of the data. Here, we infer a during application of MCMC. As is commonly done in likelihood-based analyses, we work with the log of the likelihood score, as this is numerically favourable. This is straightforward here, as the products in $L_w$ become summations in $\log L_w$.

Specification of prior distributions. Prior distributions encode our prior belief about the values of parameters. When characterising a variable that has not previously been used in a model before, it can be difficult to know how to set the prior, so in this case we use a uniform distribution with wide bounds. This prevents the MCMC sampler from being swayed by an inappropriate value. When a parameter has been seen in another analysis, we propagate the marginal posterior from the previous analysis as a prior. To do this, we use truncated Gaussian distributions, where the mean and standard deviation are calculated from the previous MCMC samples, and the bounds are taken as the uniform prior bounds of that same analysis.

Accordingly, in one embodiment, the method of the invention uses the marginal parameter posteriors of parameters that have been inferred in an upstream inference. In particular, the method may use a Gaussian approximation of the marginal posterior of the parameter as a prior, but other parametric distribution approximations can also be used.

Computing the Posterior Predictive Distribution

To evaluate a model against unseen data, we approximate the posterior predictive distribution of the data, given our best estimates of the distributions of the model's parameters. To do this, we formulate a model of the synthetic gene circuit being measured. In this article, we show calculations for the posterior predictive distribution of a circuit for which the parameters have already been characterised, so all are specified as truncated Gaussians, as described above. The predictions are formed by applying the cell growth phase and control phase as appropriate for dynamic characterisation, but for the target phase we integrate over the prior.

Accordingly, we approximate $p(y'|y)$ by marginalising over the posteriors of $p(\theta|y)$ to give approximate priors $\pi_\theta$ and then producing Monte Carlo samples $\theta_k \sim \pi_\theta$, as $$\log p(y' | y) = \log \int p(y' | \theta) p(\theta | y) d\theta$$

$$\approx \frac{1}{N} \sum_{k=1}^{N} \log p(y' | \theta_k)$$

FURTHER ASPECTS

As indicated above the method of the invention determines one or more intrinsic properties of a DNA component. Knowledge of these properties, can then be used to adapt the DNA component and include it in a genetic circuit to improve the performance of that circuit, e.g. by increasing the number of copies of the DNA component in the genetic circuit so as to improve efficiency of transcription of a gene.

In particular, the present invention further provides a method of optimizing expression of at least one gene comprised in a genetic circuit, wherein the genetic circuit further comprises a DNA component which is involved in transcription of the at least one gene, wherein the method comprises: (1) determining one or more intrinsic properties of the DNA component using the method of the invention described above; (2) using the one or more intrinsic properties of the DNA component determined in (1) to simulate expression of the at least one gene from the genetic circuit in at least two different arrangements of the genetic circuit; (3) selecting the arrangement in (2) that results in optimal expression of the at least one gene; and (4) making the arrangement of the genetic circuit selected in step (3).

The invention further provides a computer program product embodied on a computer readable storage and comprising code which is configured so as to perform the operations of the method for determining one or more intrinsic properties of a DNA component (as described above) when run on a computer system.

The following are intended as examples only and do not limit the present invention.

EXAMPLES

Results

To demonstrate how dynamic characterisation can be used to quantify the properties of biological compo-nents, we investigated homoserine lactone (HSL) signalling components. These components have been studied considerably in their natural contexts, including the Lux system from *V. fischeri* (Stevens et al., J. Bacteriol., 179(2): 557-562, 1997) and the Las system from *P. aureginosa* (Schuster et al., PNAS, 101(45): 15833-15839, 2004). The Lux and Las systems have also been used in synthetic biology contexts, either alone (Danino et al., Nature, 463(7279): 326-330, 2010), in co-culture (Balagadde et al., Molecular Systems Biology, 4(1):187, 2008), or integrated into the same host organism (Grant et al., Molecular Systems Biology, 12(1): 849, 2016). Here, we sought to apply dynamic characterisation to measurements of synthetic gene circuits that incorporate Lux and Las signalling components—receivers, senders and degraders—to establish quantitative estimates of their behaviours in *E. coli*.

Inference Graphs Enable Precise Specification of Parameter Dependencies.

An inference graph is defined as a Directed Acyclic Site Graph, where each node in the graph contains one or more sites and each site is a system, referred to by the system name. Each node essentially denotes an inference problem, consisting of one or more systems with shared parameters. Each edge between two nodes is labelled with a set of parameters to propagate from the source node to the target node. The syntax of inference site graphs is defined as follows, where italicised names denote syntax variables:

Property ::=
| Fixed
| Normal
Parameter ::=
| Name
| Name = Property
Location ::=
| Name
| Name.Name
Edge ::=
Edge Location − > [Parameter$_1$,...; Parameter$_N$] Location
Node ::=
node Name
systems = [Name$_1$;...; Name$_N$];
settings = Inference_settings;

We use a dot notation to refer to a specific system at a given node in the graph. For the corresponding implementation, the system-specific parameters can be given global names by using the system name as a prefix to avoid parameter clashes. If only a single system is present at a node, we allow syntactic sugar so that the system name can be used as the node name, and the system inference settings can be used as the node inference settings. Note that we also allow edges between nodes directly, to indicate that the parameters are shared between all systems present at the node. A node is executed by running inference on the node using the distributions of the parameters from the in-bound nodes as priors. The execution semantics essentially associates parameter posteriors to each node at the end of an inference run, where some parameters are local to a specific system at the node, while other parameters are shared between all systems at the node Modular Construction and Modelling of Synthetic Gene Circuits.

In order to characterise HSL signalling components, we designed a collection of synthetic gene circuits of increasing complexity, reusing components in equivalent genetic contexts as much as possible (FIG. 5A to F). For each circuit, a model was proposed that explicitly describes the inserted components, with parameters reused when the same promoter, ribosome binding site and protein coding regions were used. The models are all derived from elementary chemical reactions but make several assumptions about the timescales of different biological processes, culminating in only proteins and small molecules being explicitly described by ordinary differential equations (as described elsewhere herein). In FIG. 5A to F, a code snippet shows the module calls within a chemical reaction network (CRN) model, illustrating via a simple graphical schema how the modular design of each circuit maps directly onto a programmatic description. Also shown in FIG. 5A to F are example comparisons of calibrated model simulations against measurements, for each circuit.

Figure 5A:
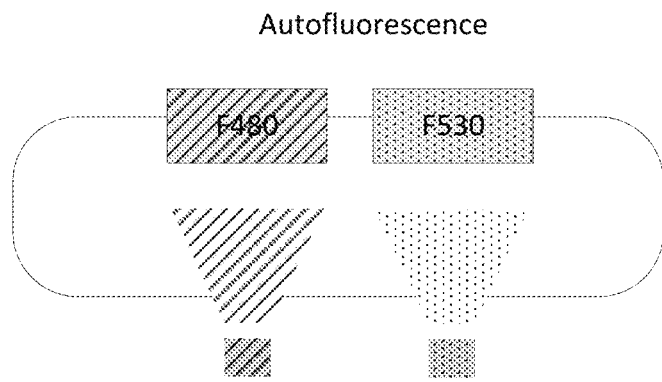
FIG. 5A to F shows the modular design and characterisation of HSL signalling components. The synthetic gene circuit and corresponding module calls within chemical reaction network (CRN) program for each circuit are shown.

We started by characterising cellular autofluorescence, so that such quantification could be used to account for autofluorescence in measurements of circuits expressing YFP and CFP explicitly (FIG. 5A). To apportion cell number and autofluorescent material appropriately, we pharmacologically perturbed the cells with EtOH, which above a threshold concentration led to very slow cell growth. We found that the per-cell rate of autofluorescence production at 480 nm (corresponding to CFP measurements) was an order of magnitude higher than at 530 nm (corresponding to YFP measurements). The autofluorescence parameters were then reused in subsequent circuits.

Figure 5B:
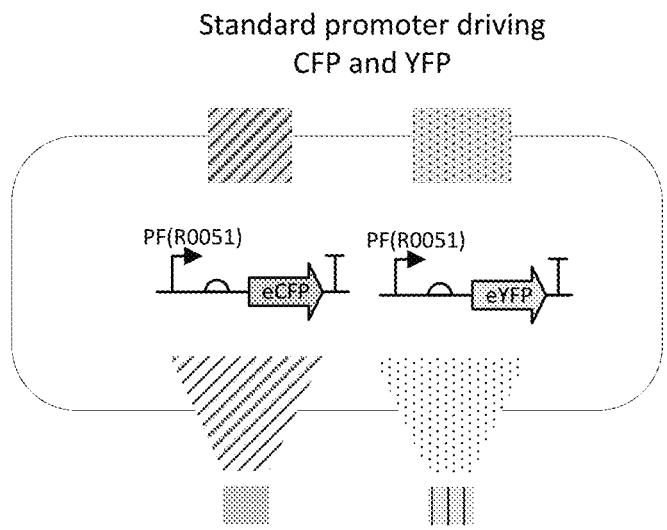

As CFP and YFP are used in the majority of the synthetic gene circuits considered, we attempted to characterise their stability in a circuit free of the complexity of inducible expression (FIG. 5B). Therefore, we expressed each fluorescent protein constitutively using the PR promoter, and then measured this PRPR circuit for 36 hours. A model of the PRPR circuit incorporated autofluorescence terms, which shared information with the Auto circuit in FIG. 5A. The observed curvature in the time-series measurements of PRPR enabled identification of the CFP and YFP degradation parameters.

Figure 5C:
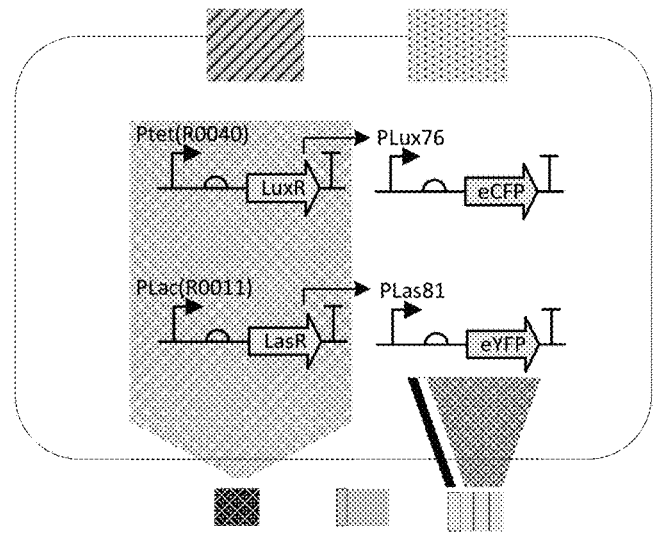

The first HSL components we characterised were the receiver proteins and HSL-inducible promoters, as these receiver components must be used in circuits that seek to characterise HSL senders and/or degraders. We used the double receiver (DR) circuits developed by the authors and their collaborators in (Grant et al., Molecular Systems Biology, 12(1): 849, 2016), which acts as a dual reporter of C6-HSL and C12-HSL (FIG. 5C). This is achieved by the constitutive expression of LuxR and LasR, and the inducible expression of fluorescent reporter proteins by genetically altered PLux promoters that respond almost orthogonally to regulators composed of C6-HSL bound to LuxR or C12-HSL bound to LasR. In this way, CFP reports the concentration of C6-HSL and YFP reports the concentration of C12-HSL, both across a broad range of concentrations. Because different promoters and ribosome binding sites are upstream of the coding sequences for CFP and YFP, as compared to the PRPR circuit, the parameters for their maximal production rate were assumed to take on new parameters. However, the degradation parameters were assumed to be the same as for PRPR, as the degradation rate is an intrinsic property of the protein. We used four different DR circuits, each incorporating a unique combination of ribosome binding sites in their LuxR and LasR expression cassettes. As explained in previous work, this enables the effect of variable intracellular concentrations of LuxR and LasR to be modelled and therefore characterised quantitatively, which is critical for identifying chemical and genetic crosstalk (Grant et al., Molecular Systems Biology, 12(1): 849, 2016). We found that the accumulation of fluorescent protein in response to different concentrations of C6-HSL and C12-HSL could be captured with parameterizations that were similar to those found previously (Grant et al., Molecular Systems Biology, 12(1): 849, 2016), demonstrating that dynamic characterisation applied to circuits with only moderate changes in promoter activity over time produces equivalent results to static methods.

Figure 5D:
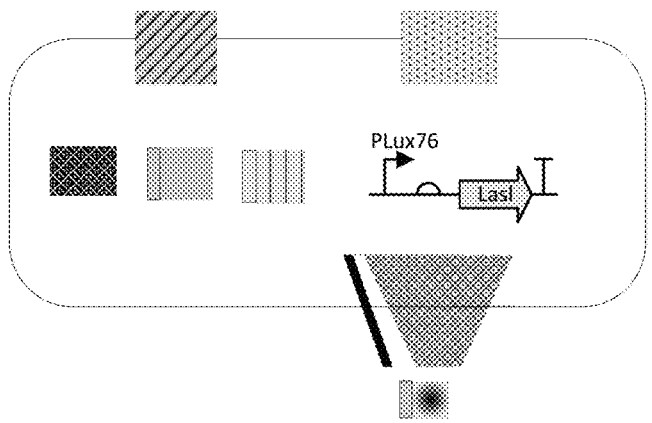
Figure 12A:
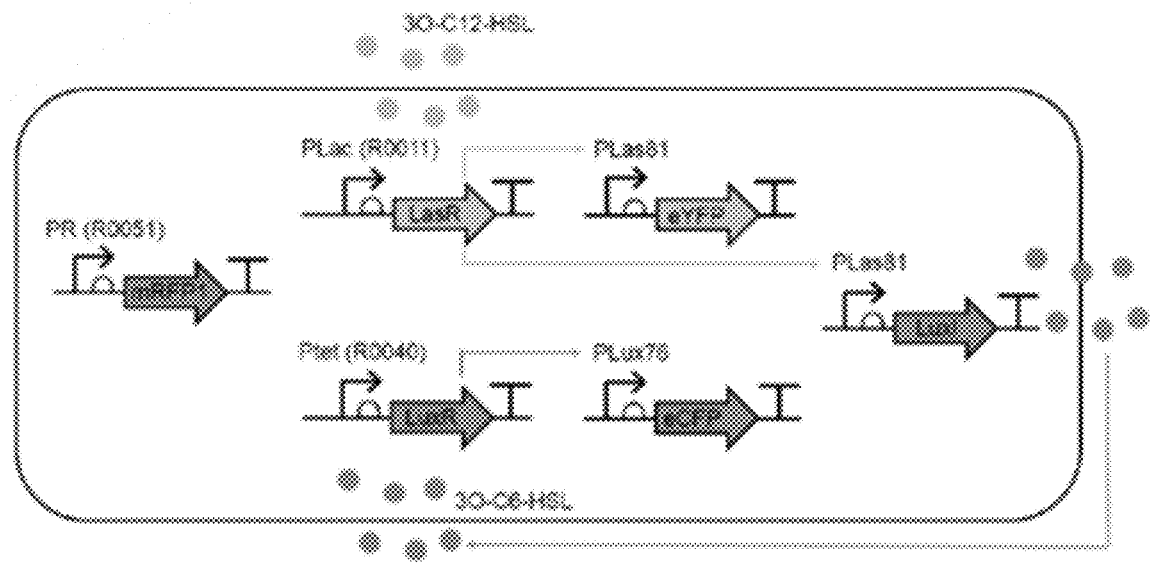
FIGS. 12A and 12B show relay circuit network diagrams.
Figure 12B:
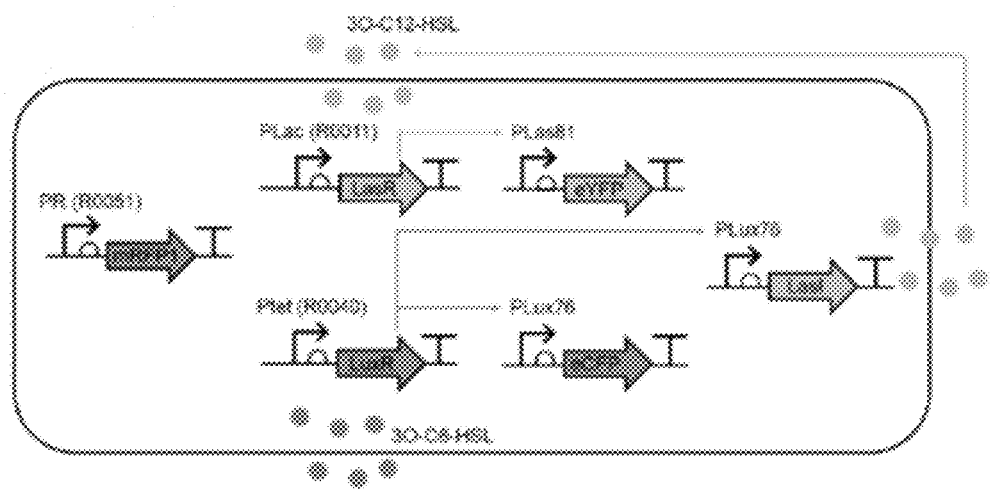

We next characterised LuxI and LasI, the synthases of C6-HSL and C12-HSL respectively. HSL sender relay circuits were designed that inducibly express the synthase of one signal in response to the other, producing a truly time-varying promoter activity for the response to the synthesized signal that therefore cannot be characterised using static methods. The first relay uses the C6-HSL-responsive pLux76 promoter to drive expression of LasI (abbreviated as P76-LasI from now on), leading to intracellular production of C12-HSL and subsequent induced expression of YFP via the pLas81 promoter (FIGS. 5D & 12B). The second uses the C12-HSL responsive pLas81 promoter to drive expression of LuxI (P81-LuxI), leading to intracellular production of C6-HSL and subsequent induced expression of CFP (FIG. 12A). Again, reusing component characterisation of the previously described circuits, we modelled time-series measurements of the response to different concentrations of C6-HSL and C12-HSL, enabling quantification of the ability of LuxI and LasI to synthesize HSLs.

Figure 5E:
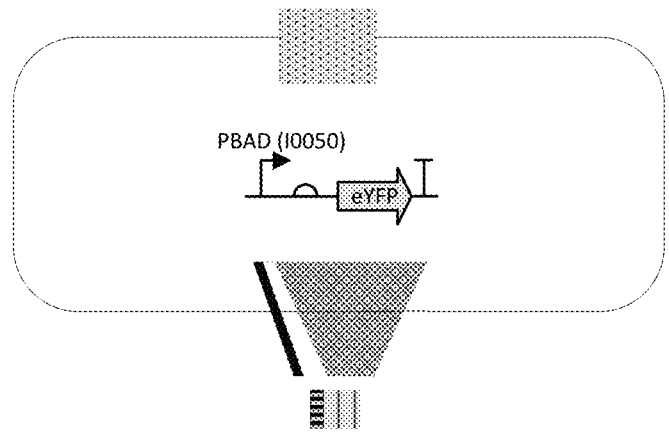
Figure 5F:
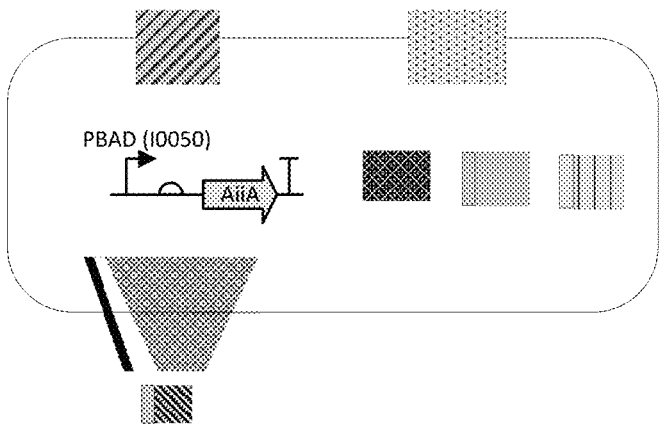
Figure 5G:
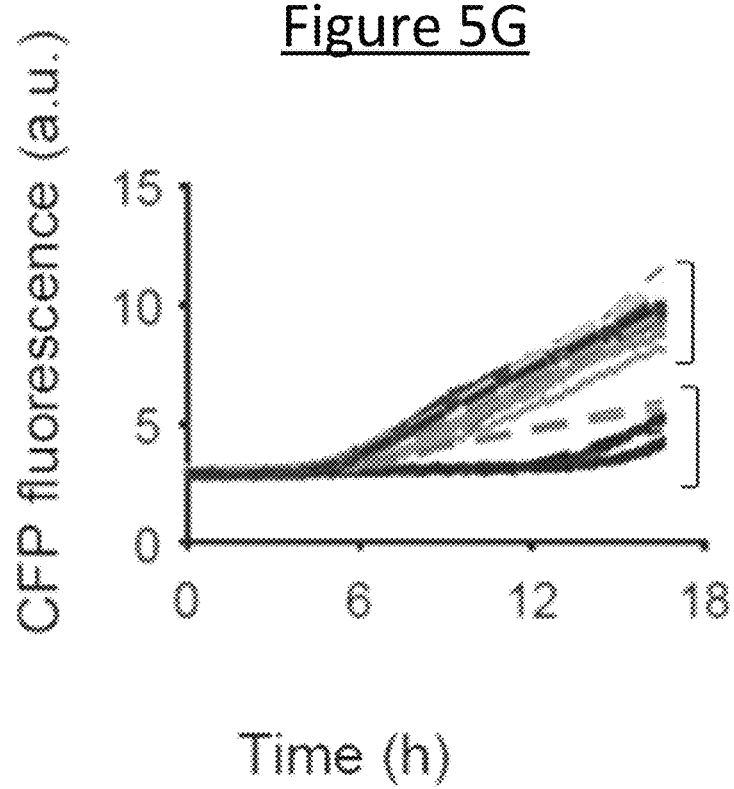
FIG. 5G to Q provide graphs showing example measurements (solid lines (or dots in FIG. 5H) and calibrated model simulations (dashed lines) for the synthetic circuits represented in FIGS. 5A to 5F.
Figure 5H:
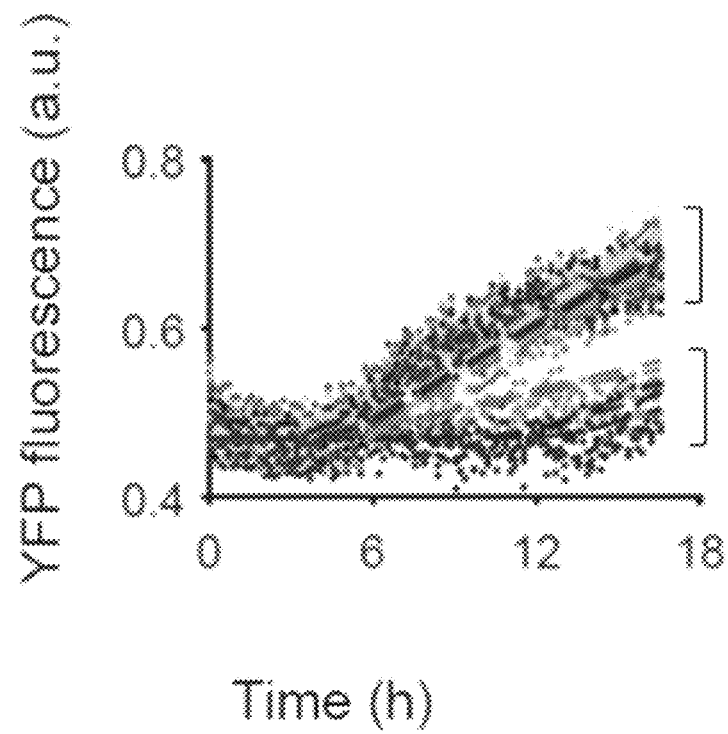
Figure 5I:
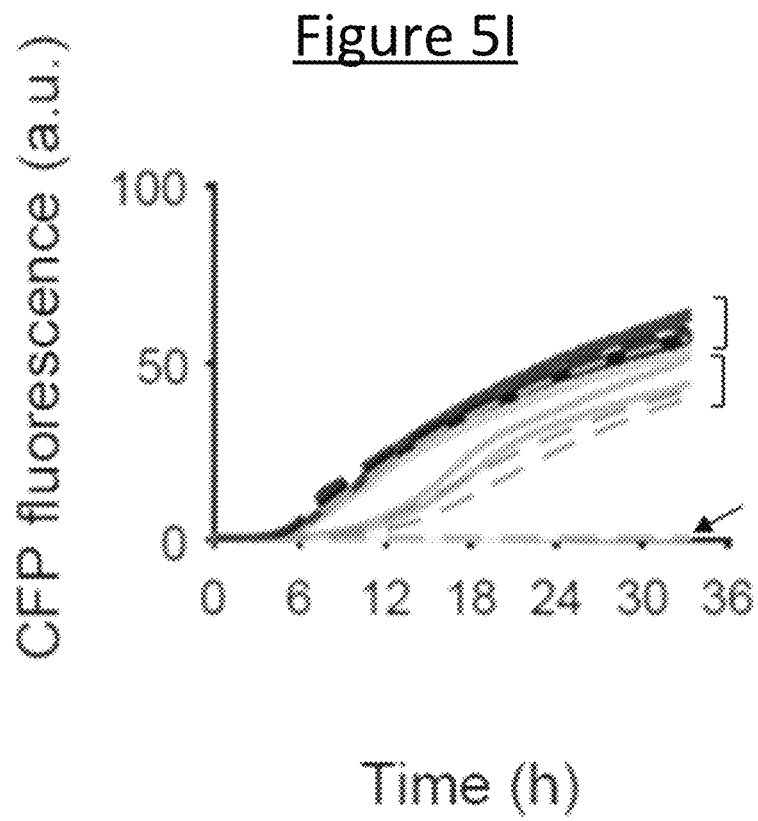
Figure 5J:
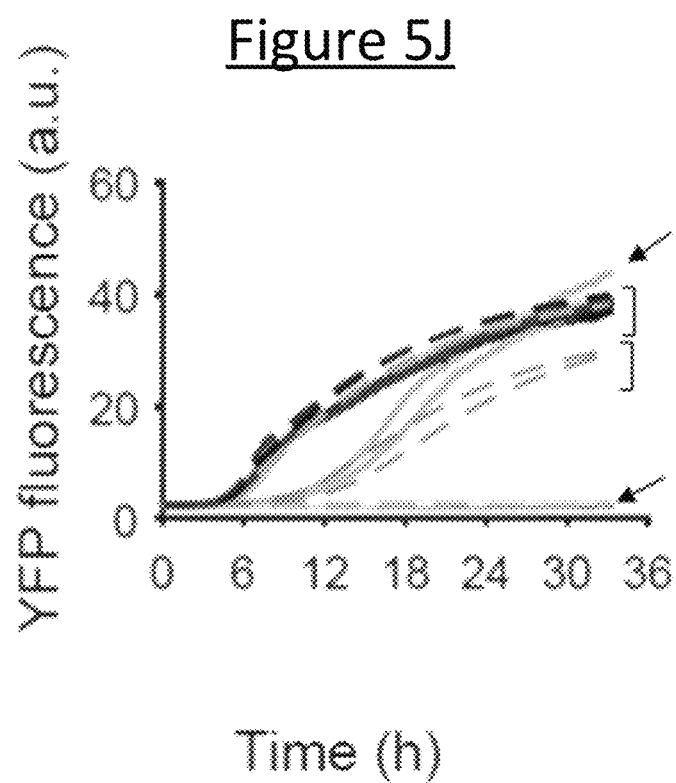
Figure 5K:
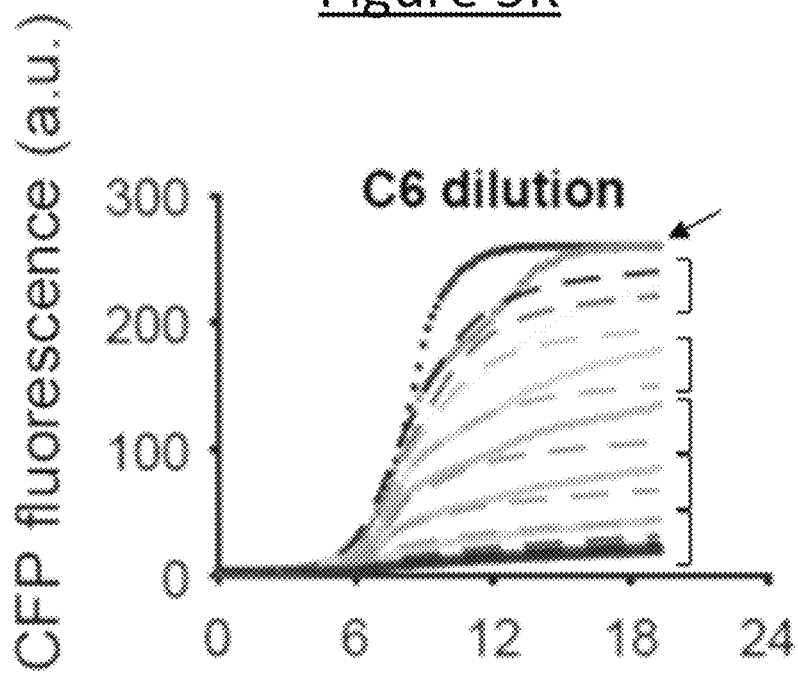
Figure 5L:
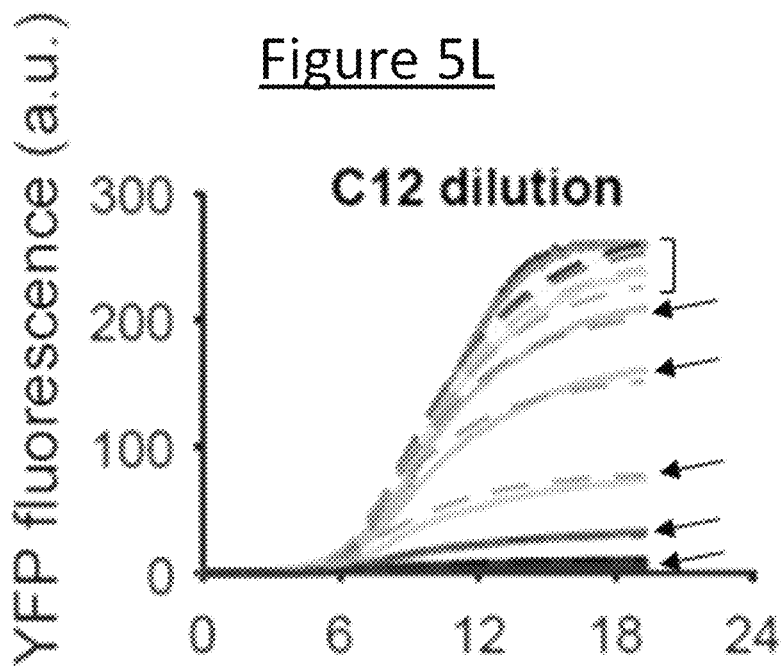
Figure 5M:
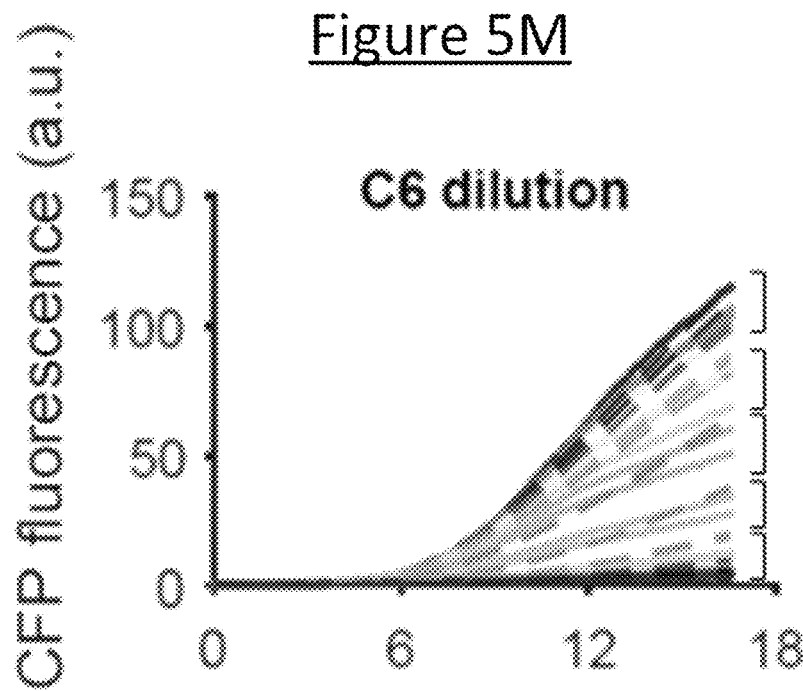
Figure 5N:
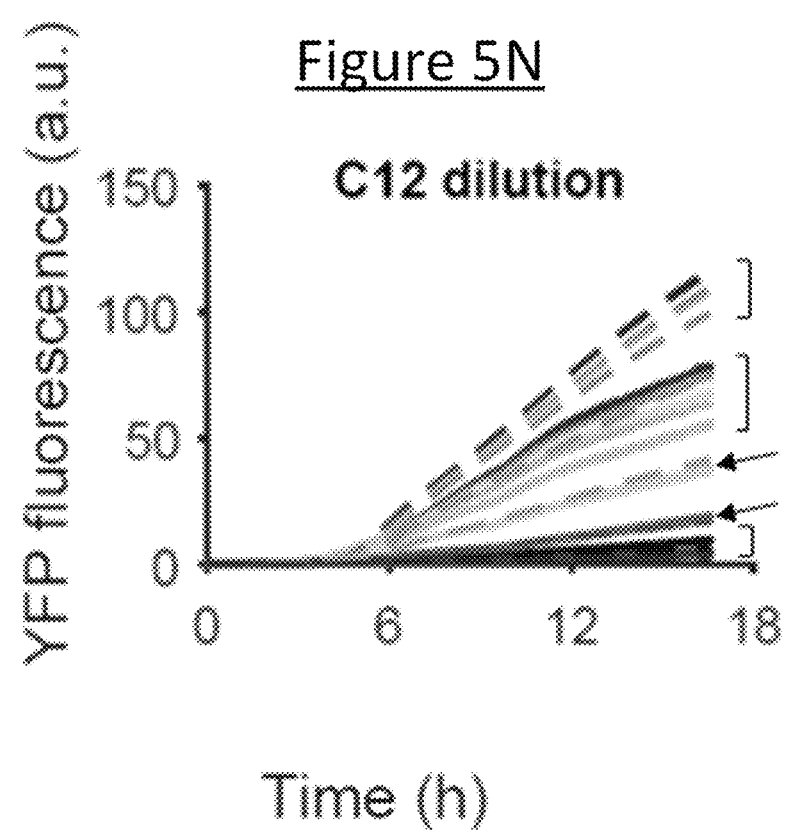
Figure 5O:
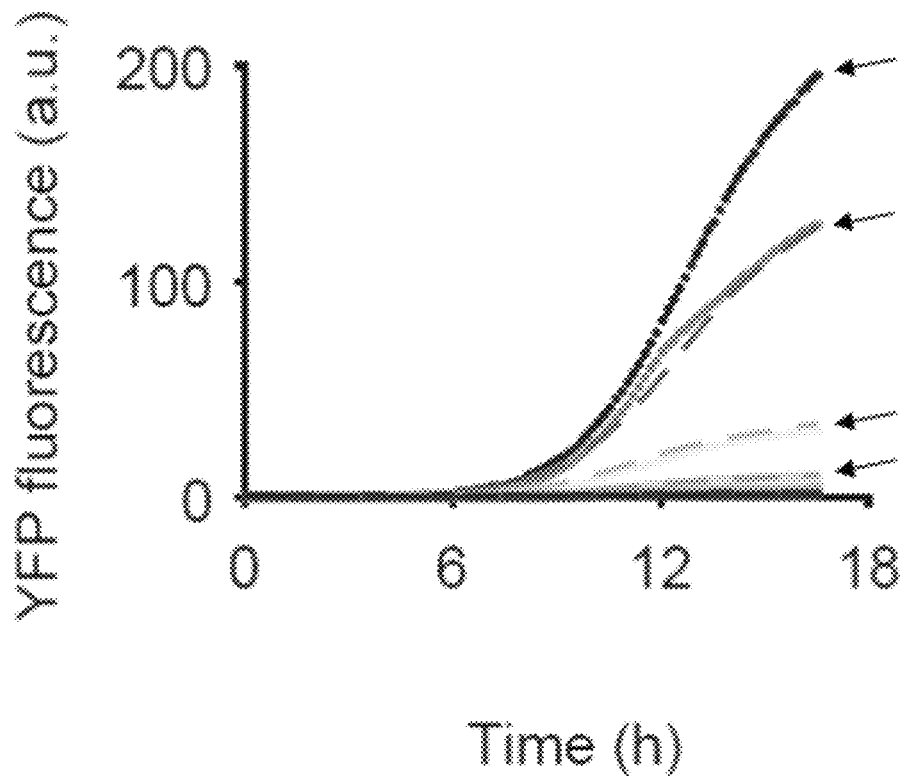
Figure 5P:
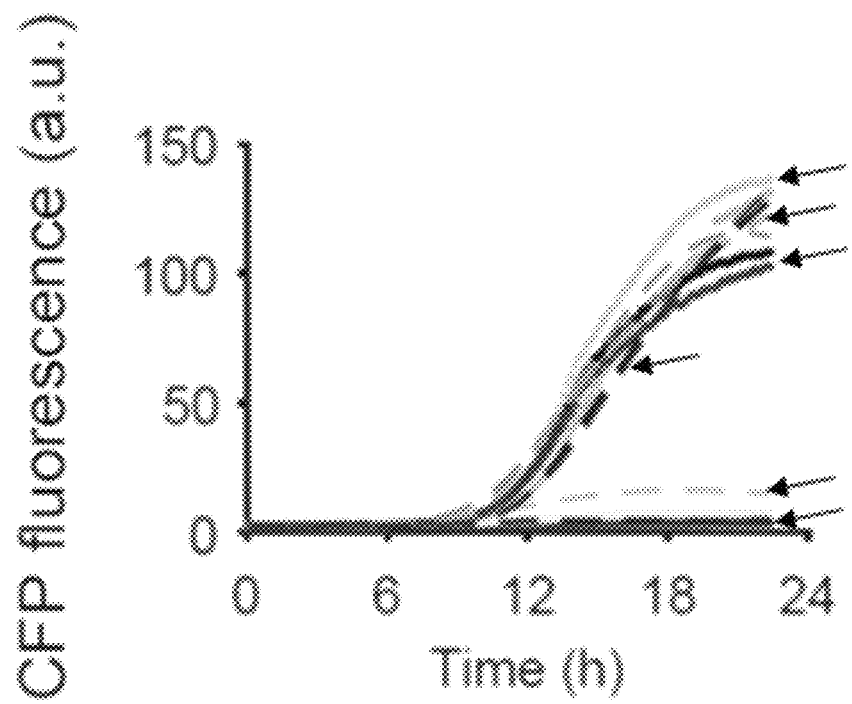
Figure 5Q:
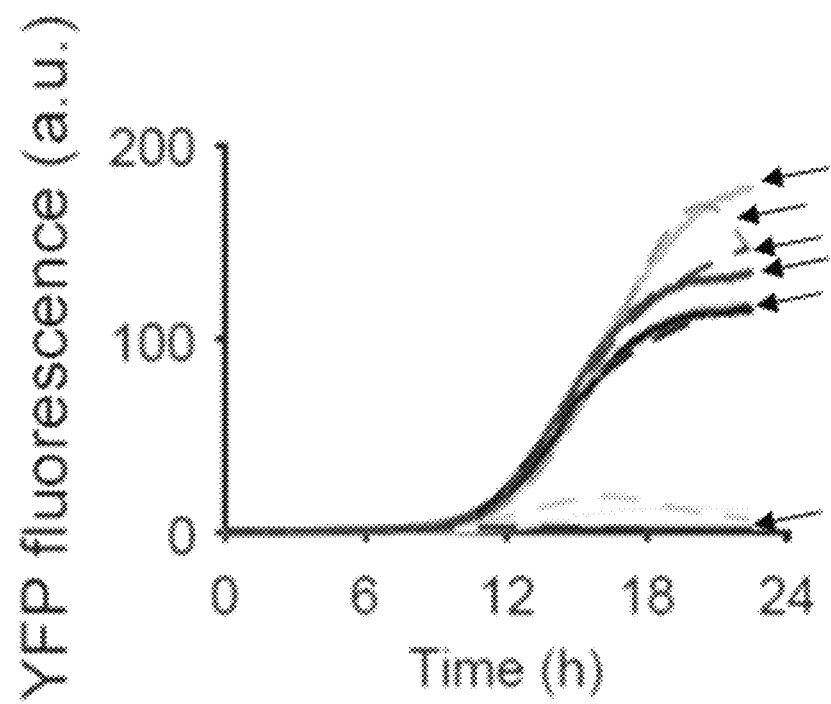
Figure 13:
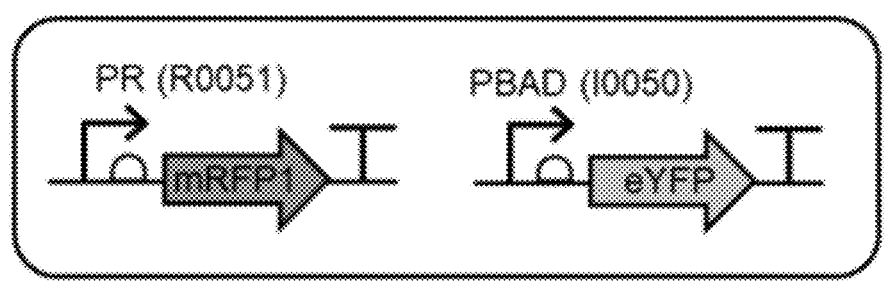
FIG. 13 shows the design of PBAD gene circuit.

To characterise the HSL degrader AiiA (Liu et al., Biochemistry, 47(29):7706-7714, 2008), we designed a circuit in which AiiA was placed under the control of the arabinose-inducible PBad promoter (FIG. 5F), so that different intracellular levels of AiiA could be produced experimentally. However, analogous to the strategy used thus far, we first characterised a simpler circuit in which the properties of arabinose induction of PBad could be quantified, by simply using PBad to drive YFP expression (FIGS. 5E & 13). Incorporating the YFP autofluorescence parameter from above, our model of the Pbad circuit closely described the experimental measurements in response to different concentrations of arabinose (FIG. 5E) and enabled identification of the transfer function parameters for arabinose-induction. Embedding the characterised PBad and DR modules into the model of the AiiA circuit enabled modelling of the response to different concentrations of C6-HSL, C12-HSL and arabinose. Of particular importance in reproducing the observed bulk fluorescence dynamics was the incorporation of the effect on cell growth of high arabinose induction of AiiA, which was observable in the $OD_{600}$ data, and therefore quantified during the cell growth phase of dynamic characterisation.

Time-Varying Gene Expression Capacity Improves Model Fit in Stationary Phase.

The simplest assumption that can be made about cellular gene expression capacity (h(c)) is that it remains constant through time. However, because circuit activity changes over time, this assumption is likely to break down, as RNA polymerases and ribosomes may become limiting when circuit activity increases. As such, we considered four alternative time-dependent functions for defining h(c) and applied dynamic characterisation to each circuit (Table 1).

TABLE 1

Functional forms used to define gene expression capacity ($h_i(c)$).

| Description | Function ($h_i(c)$) |
|---|---|
| Constant | $r_c^{(i)}$ |
| TargetGrowth<br>Tracks the growth-rate γ,<br>falling to a basal level $\epsilon_c$. | $r_c^{(i)}((1 - \epsilon_c)\gamma(c) + \epsilon_c)$ |
| TargetGrowthDelay<br>Tracks the growth-rate γ<br>at time t − τ | $r_c^{(i)}((1 - \epsilon_c)\gamma(c(t - \tau)) + \epsilon_c)$ |
| TargetRSwitch<br>Sigmoid that switches at<br>c = $K_c$ from a well-specific<br>value $r_c$ to a relative value $\epsilon_c$ | $r_c^{(i)} \dfrac{c^{n_c} + \epsilon_c K_c^{n_c}}{c^{n_c} + K_c^{n_c}}$ |
| TargetSwitch<br>Sigmoid that switches at<br>c = $K_c$ from a well-specific<br>value $r_c$ to a non-well-specific<br>basal value $r_s$ | $\dfrac{r_c^{(i)} c^{n_c} + r_s K_c^{n_c}}{c^{n_c} + K_c^{n_c}}$ |

In each case, the well-specific component $rc^{(i)}$ is inferred during the control phase, under a Constant hypothesis. Then, the non-well-specific parameters (e.g. $\epsilon_c$ in TargetGrowth) is inferred in the target phase alongside the target circuit parameters θ. As such, these hypotheses assume that the gene expression capacity for the chromosomally integrated control undergoes contrasting regulation from that of the plasmid-expressed circuit components. In principle, every gene expressed on the plasmid might be regulated differently, which would require gene-specific functions and/or parameterisations. Here, we only consider one such function and parameterisation that is applied to the whole circuit, preventing a combinatorial increase in the number of parameters to infer.

Dynamic Characterisation can be Applied Sequentially or Simultaneously to Multiple Datasets.

Figure 6A:
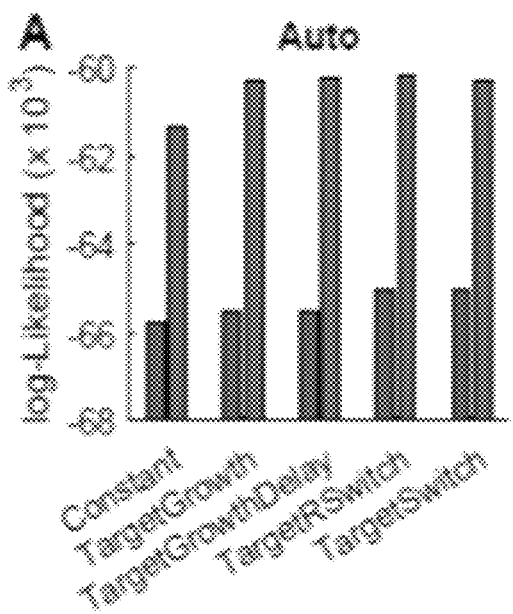
FIG. 6A bar chart showing maximum log-likelihood score of inference problem of autofluorescent as per FIG. 5A for the 5 hypotheses about the dynamics of gene expression capacity shown in Table 1. (Right hand bars: Ratiometric characterisation method; Left hand bars: Direct characterisation method.)
Figure 6B:
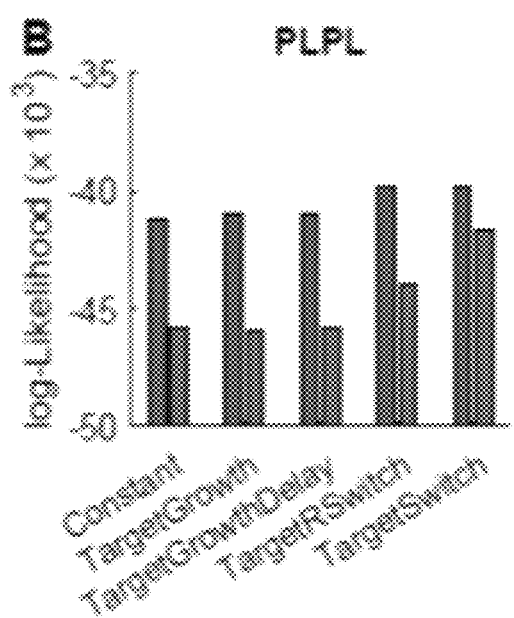
FIG. 6B bar chart showing maximum log-likelihood score of inference problem of constitutive promoter gene circuit shown in FIG. 10 for the 5 hypotheses about the dynamics of gene expression capacity shown in Table 1. (Right hand bars: Ratiometric characterisation method; Left hand bars: Direct characterisation method.)
Figure 6C:
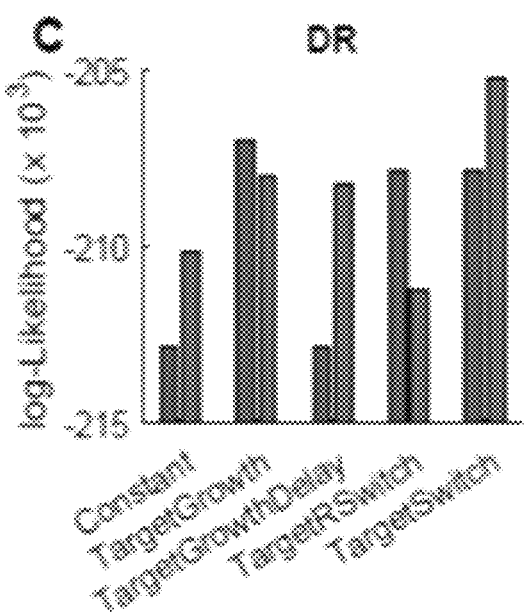
FIG. 6C bar chart showing maximum log-likelihood score of inference problem of AHL double receiver gene circuit shown in FIG. 11, for the 5 hypotheses about the dynamics of gene expression capacity shown in Table 1. (Right hand bars: Ratiometric characterisation method; Left hand bars: Direct characterisation method.)
Figure 6D:
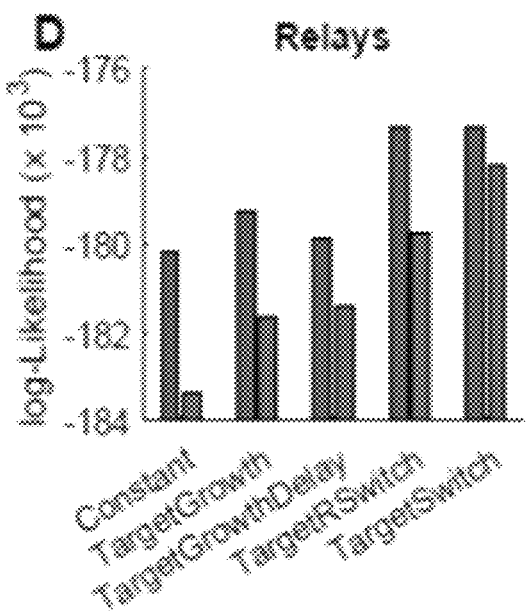
FIG. 6D bar chart showing maximum log-likelihood score of inference problem of AHL senders (relays) gene circuits shown in FIGS. 12A and 12B, for the 5 hypotheses about the dynamics of gene expression capacity shown in Table 1. (Right hand bars: Ratiometric characterisation method; Left hand bars: Direct characterisation method.)
Figure 6E:
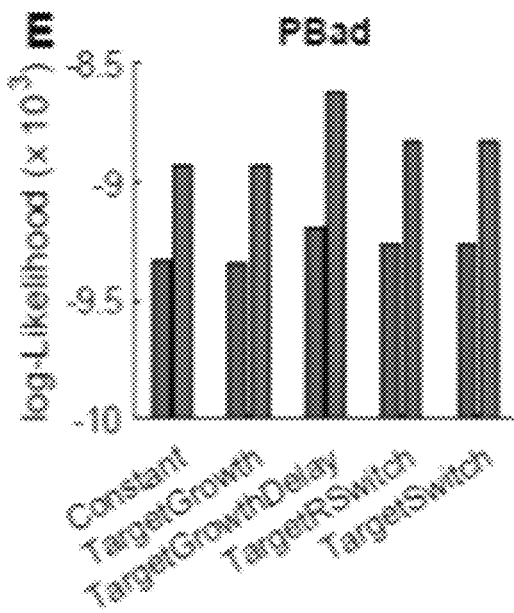
FIG. 6E bar chart showing maximum log-likelihood score of inference problem of PBad gene circuit shown in FIG. 13, for the 5 hypotheses about the dynamics of gene expression capacity shown in Table 1. (Right hand bars: Ratiometric characterisation method; Left hand bars: Direct characterisation method.)
Figure 6F:
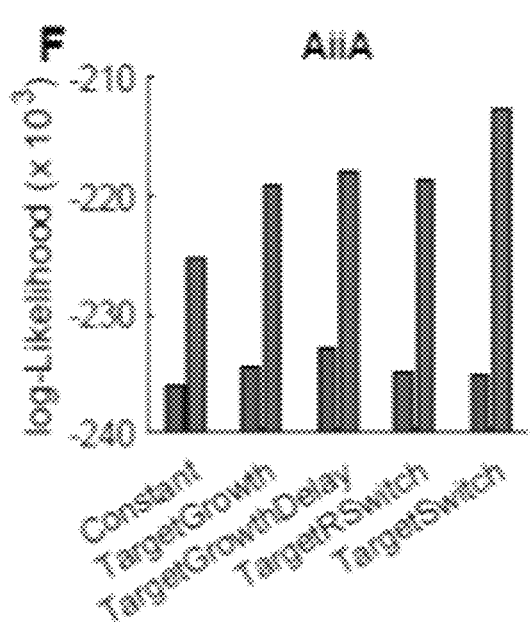
FIG. 6F bar chart showing maximum log-likelihood score of inference problem of AHL laconase (AiiA) gene circuit shown in FIG. 14, for the 5 hypotheses about the dynamics of gene expression capacity shown in Table 1. (Right hand bars: Ratiometric characterisation method; Left hand bars: Direct characterisation method.)
Figure 6G:
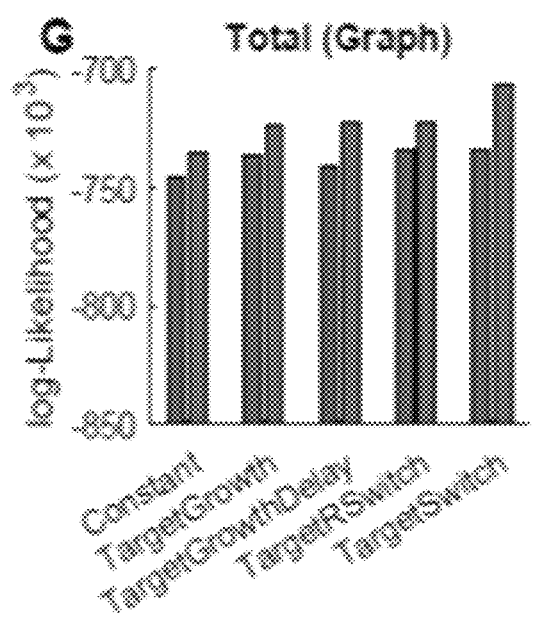
FIG. 6G bar chart showing the sum of the maximum log-likelihood score of the six inference problems represented in FIGS. 6A to 6F, for the 5 hypotheses about the dynamics of gene expression capacity shown in Table 1. (Right hand bars: Ratiometric characterisation method; Left hand bars: Direct characterisation method.)
Figure 6H:
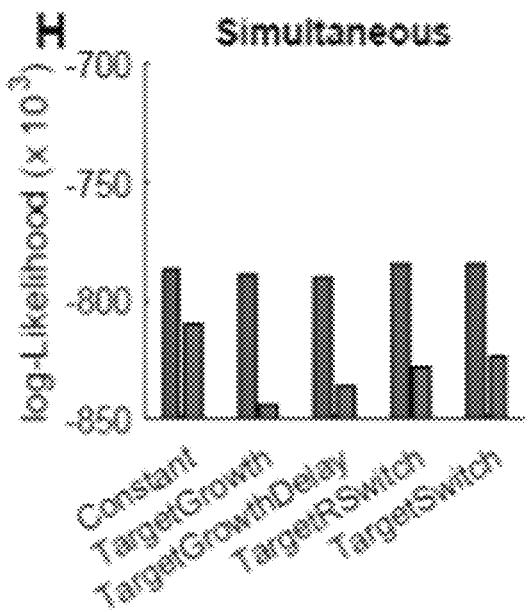
FIG. 6H bar chart showing maximum log-likelihood score of the simultaneous method applied to parametize the six circuits of FIGS. 6A to 6F, for the 5 hypotheses about the dynamics of gene expression capacity shown in Table 1. (Right hand bars: Ratiometric characterisation method; Left hand bars: Direct characterisation method.)
Figure 7A:
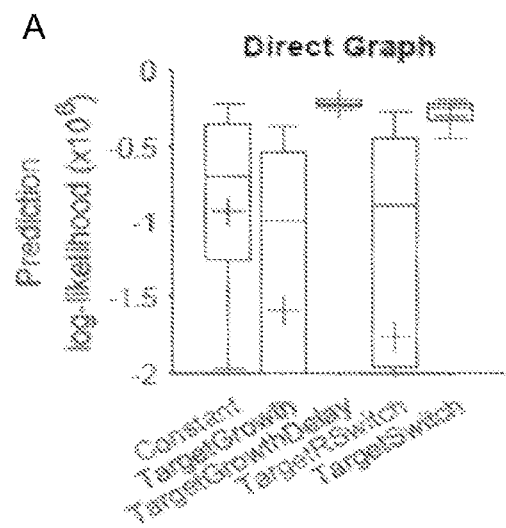
FIG. 7A graph showing the posterior predictive distribution quantified for direct dynamic characterisation using the graph-based method for the 5 hypotheses about the dynamics of gene expression capacity shown in Table 1. The box-plots indicate the interquartile range of samples from the marginalized parameter posteriors. The plus symbols indicate the means of each distribution.
Figure 7B:
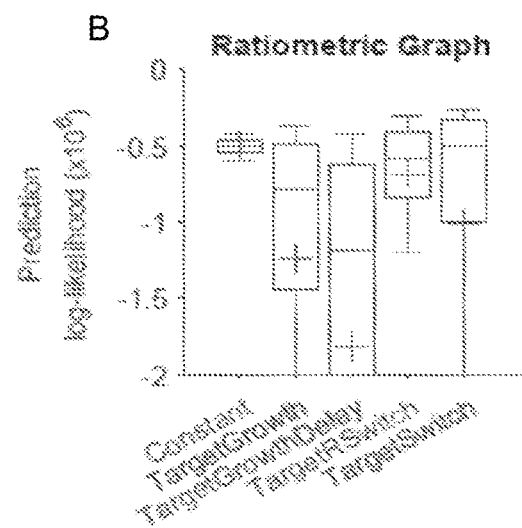
FIG. 7B graph showing the posterior predictive distribution quantified for ratiometric dynamic characterisation using the graph-based method for the 5 hypotheses about the dynamics of gene expression capacity shown in Table 1. The box-plots indicate the interquartile range of samples from the marginalized parameter posteriors. The plus symbols indicate the means of each distribution.
Figure 7C:
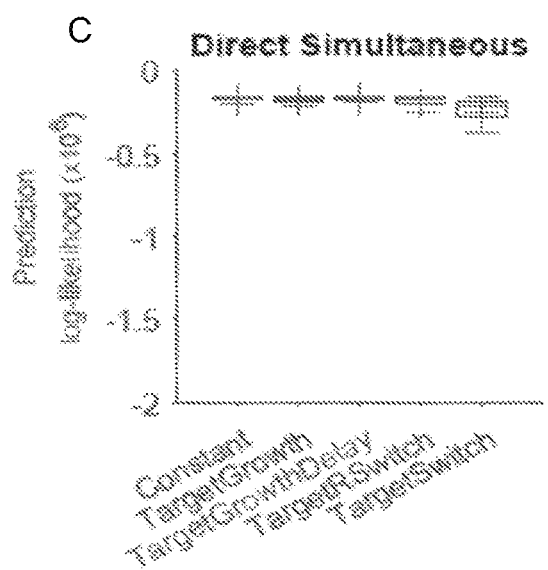
FIG. 7C graph showing the posterior predictive distribution quantified for direct dynamic characterisation using the simultaneous method for the 5 hypotheses about the dynamics of gene expression capacity shown in Table 1. The box-plots indicate the interquartile range of samples from the marginalized parameter posteriors. The plus symbols indicate the means of each distribution.
Figure 7D:
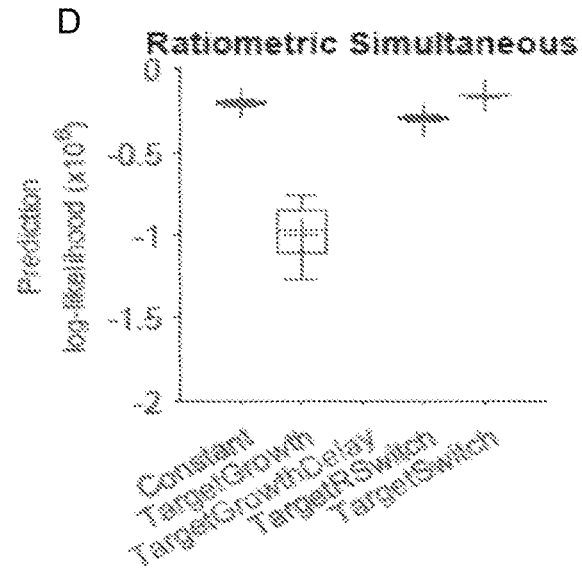
FIG. 7D graph showing the posterior predictive distribution quantified for the ratiometric dynamic characterisation using the simultaneous method for the 5 hypotheses about the dynamics of gene expression capacity shown in Table 1. The box-plots indicate the interquartile range of samples from the marginalized parameter posteriors. The plus symbols indicate the means of each distribution.
Figure 7E:
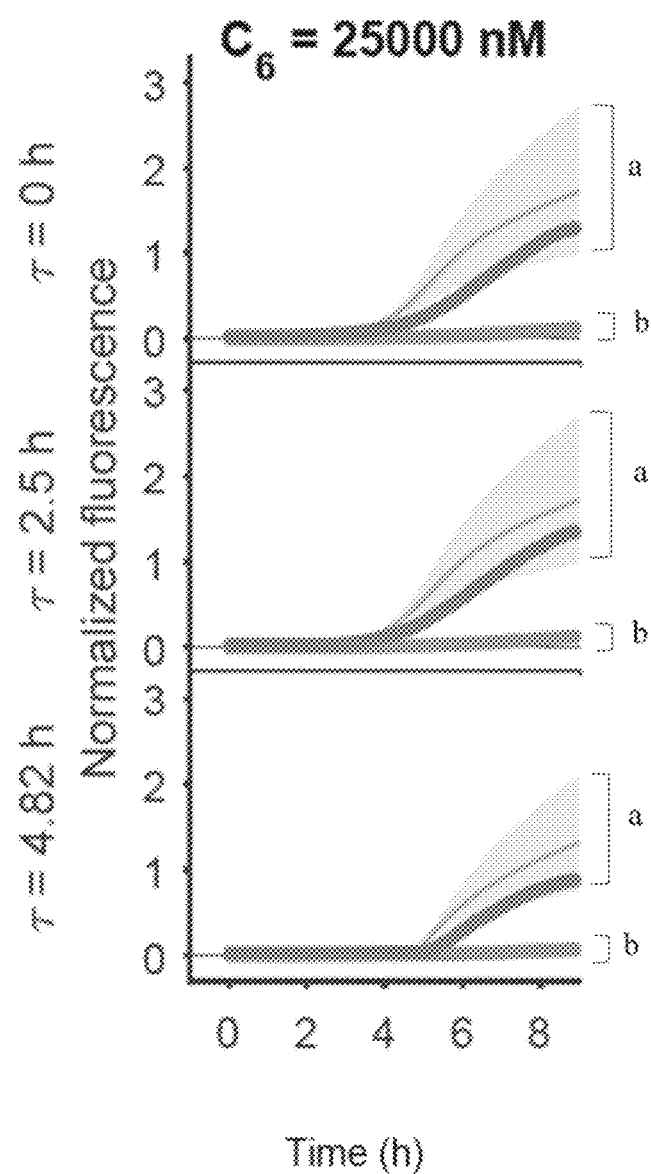
FIGS. 7E to J. Graphs showing a comparison of the posterior predictive distribution for the TargetSwitch model using the direct graph method. HSL treatment indicated above graph. Time of HSL addition: 0 h, 2.5 h and 4.82 h. YFP and CFP data are shown as thick lines, with model simulations depicted as the mean as thin lines, and 95% credibility intervals as the shaded regions marked at right hand edge as region a (for CFP) and region b (for YFP). Thick line and thin line within region a are CFP data and model lines, respectively.
Figure 7F:
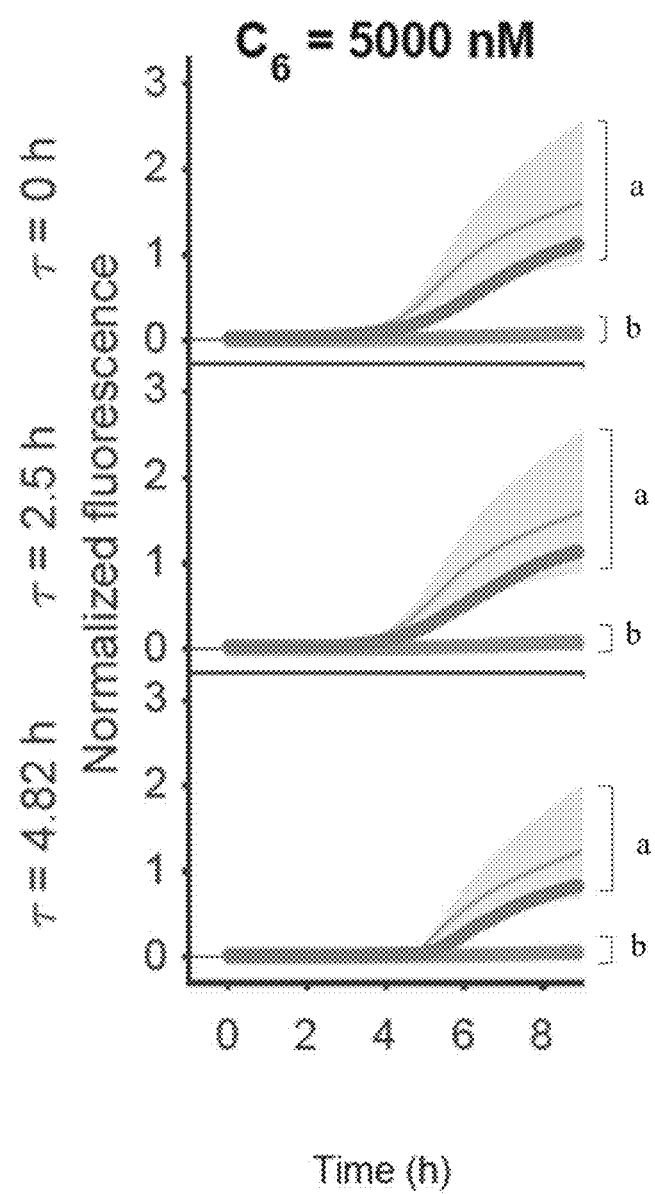
Figure 7G:
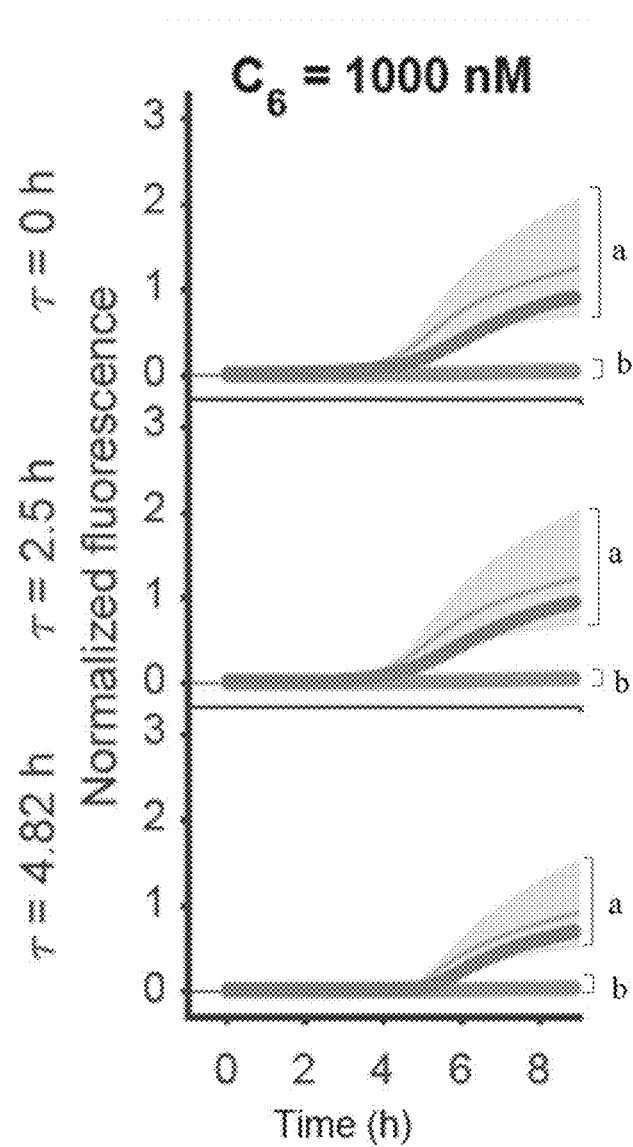
Figure 7H:
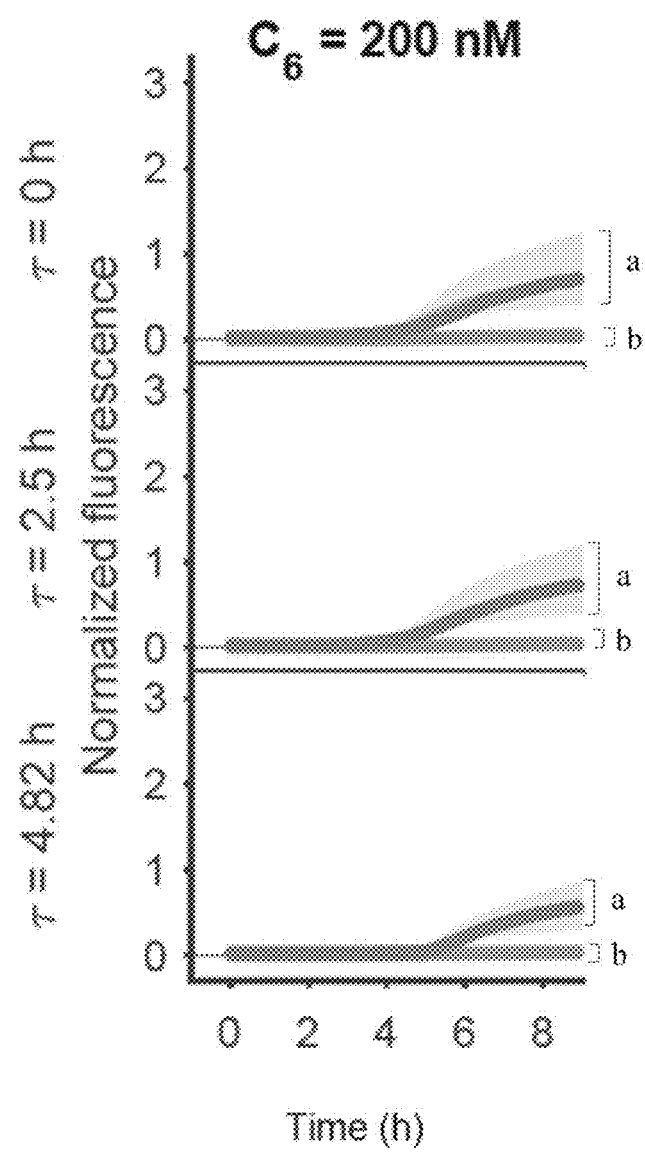
Figure 7I:
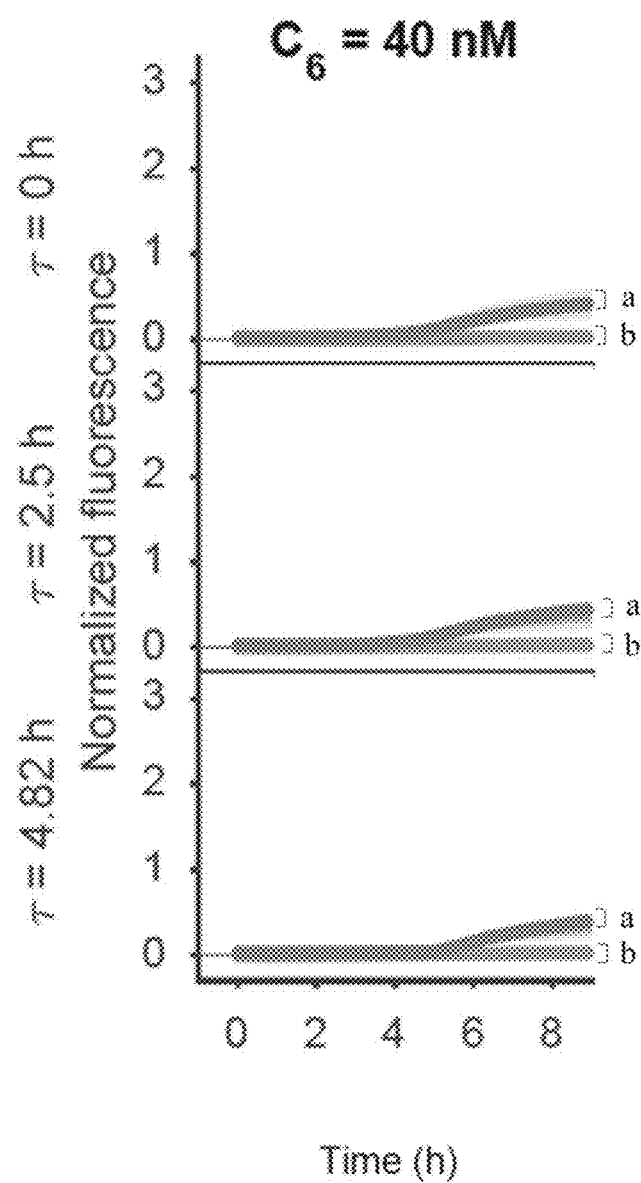
Figure 7J:
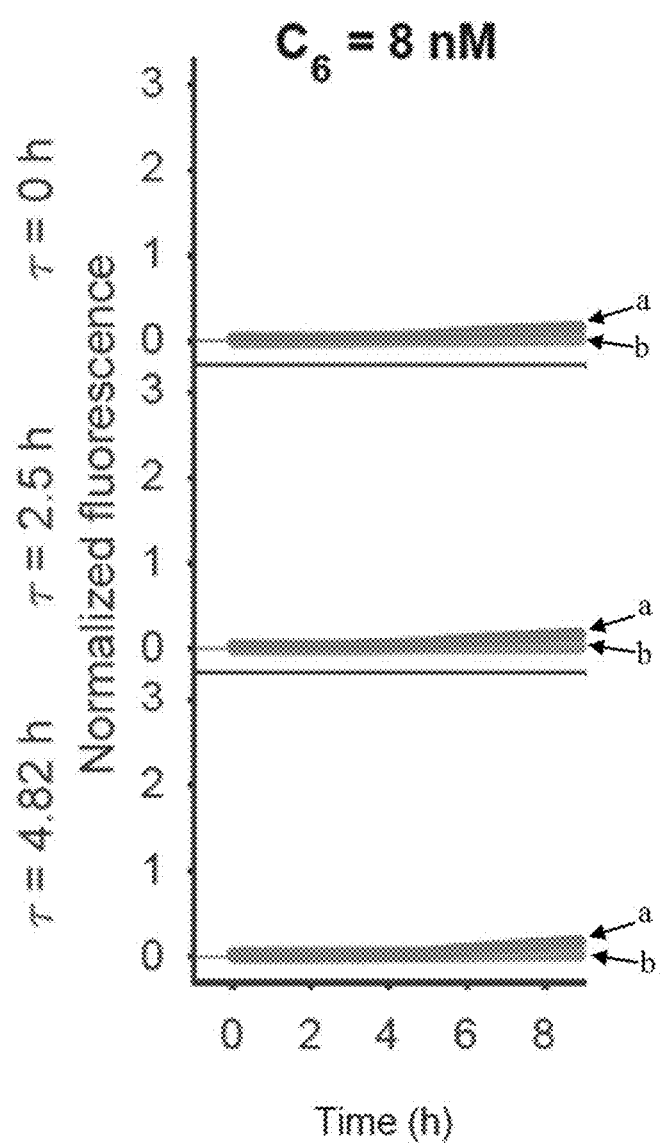
Figure 7K:
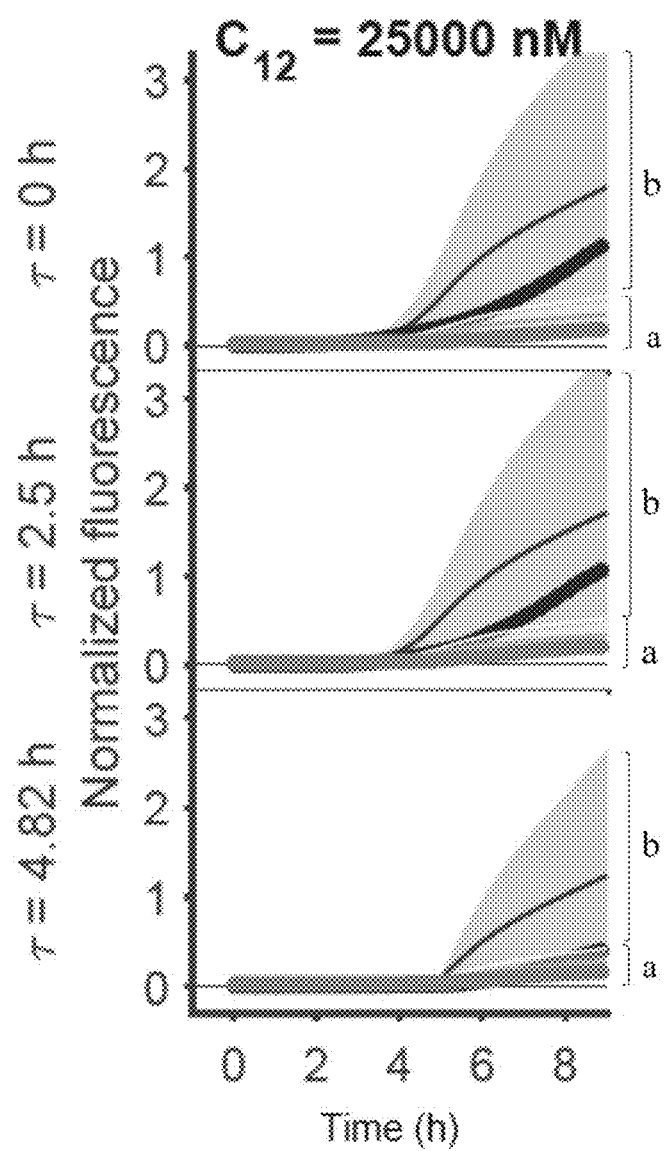
FIGS. 7K to P Graphs showing a comparison of the posterior predictive distribution for the TargetSwitch model using the direct graph method. HSL treatment indicated above graph. Time of HSL addition: 0 h, 2.5 h and 4.82 h. YFP and CFP data are shown as thick lines, with model simulations depicted as the mean as thin lines, and 95% credibility intervals as the shaded regions marked at right hand edge as region a (for CFP) and region b (for YFP). Thick line and thin line within region b are YFP data and model lines, respectively.
Figure 7L:
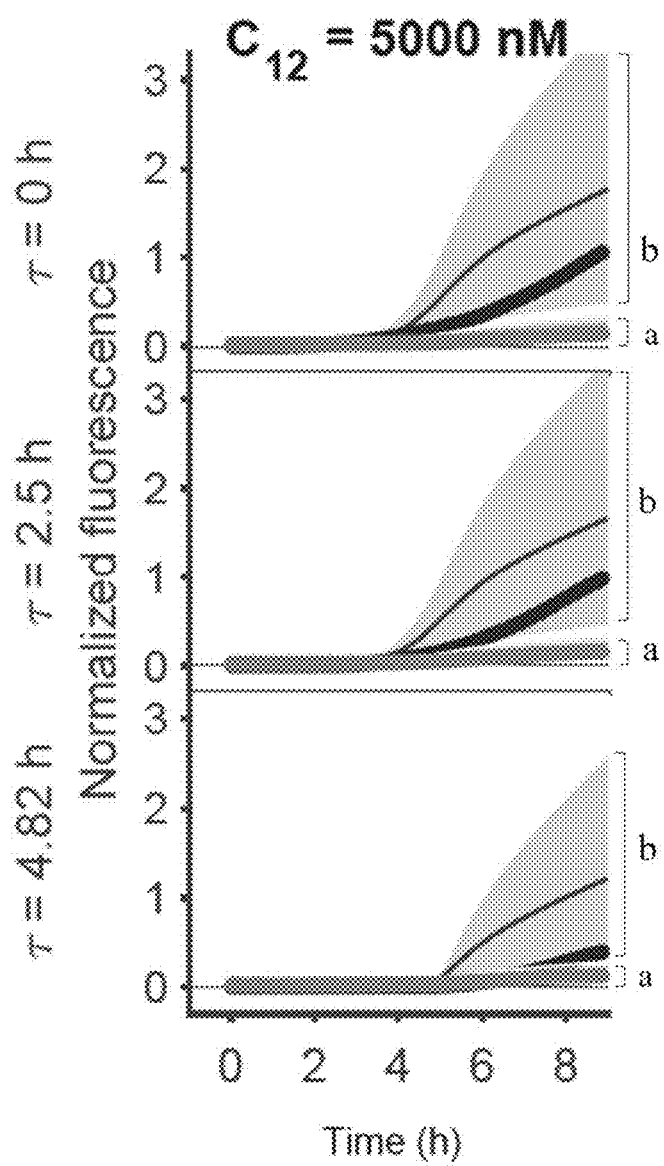
Figure 7M:
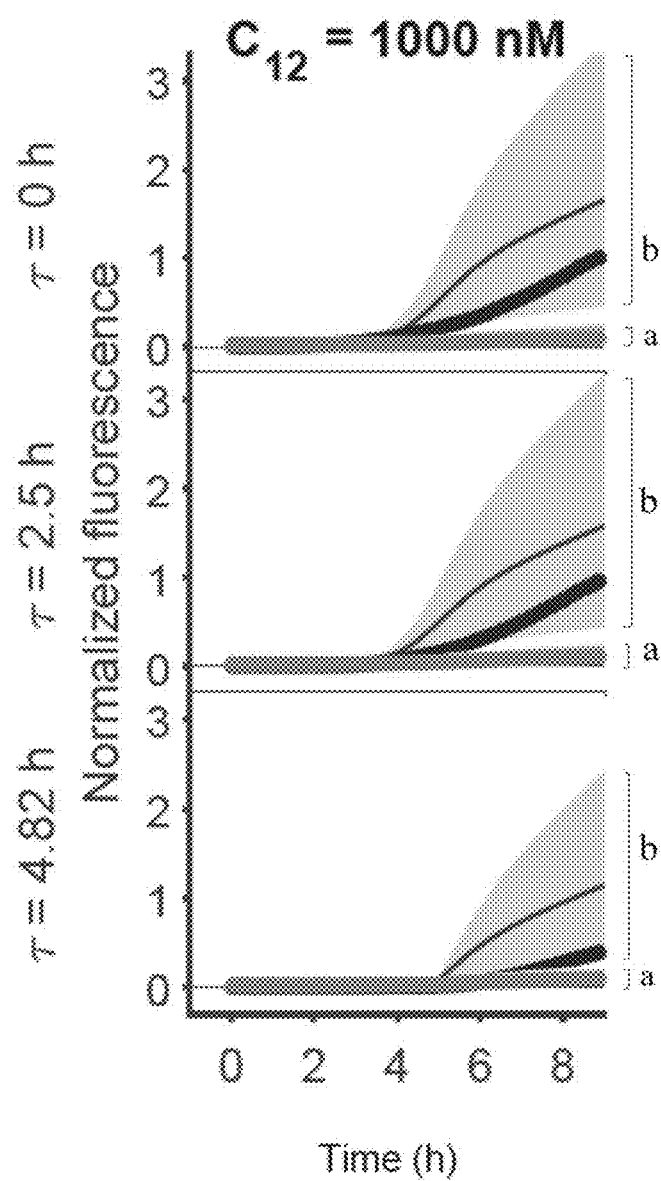
Figure 7N:
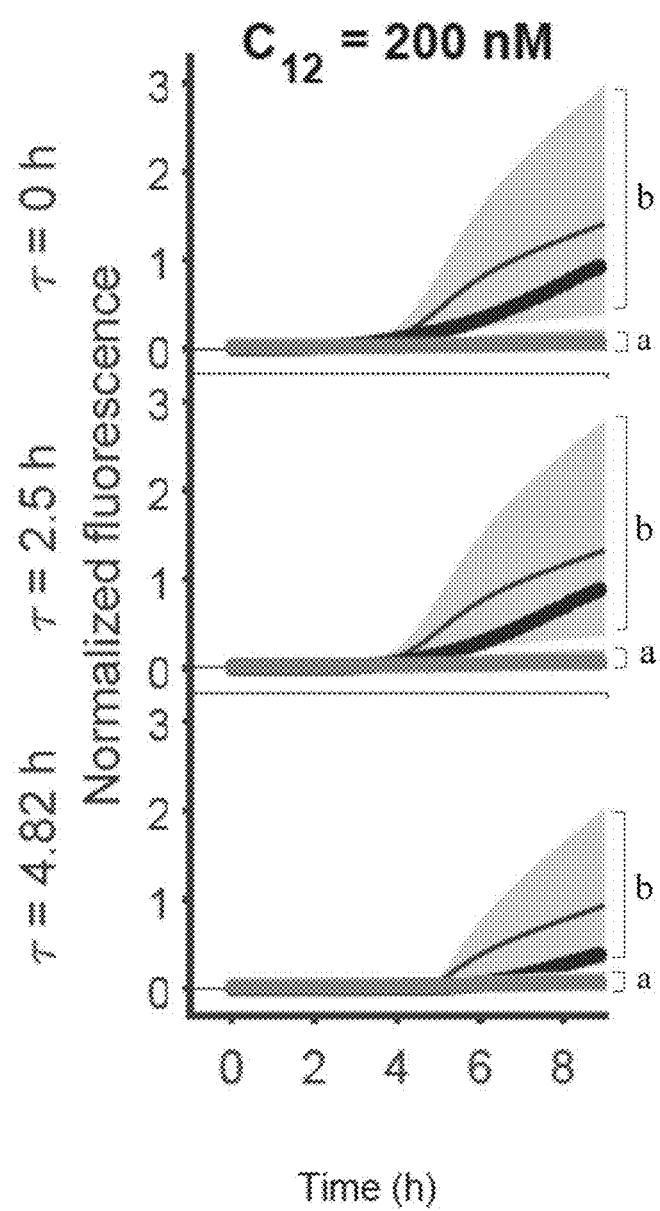
Figure 7O:
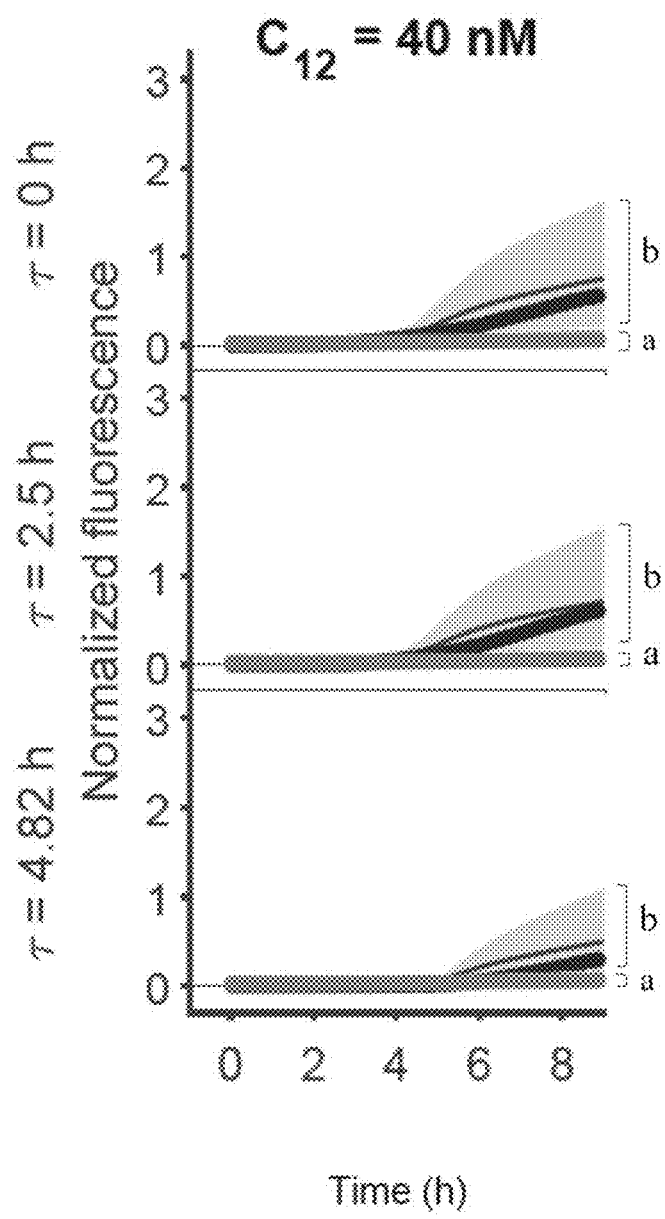
Figure 7P:
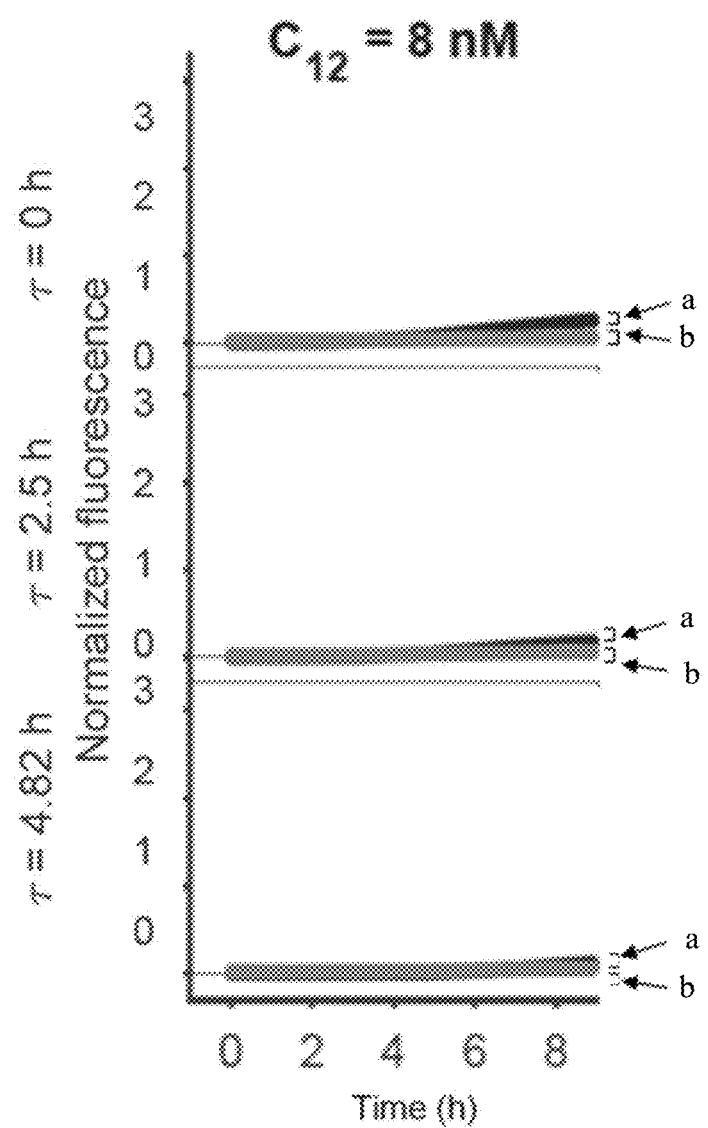
Figure 8:
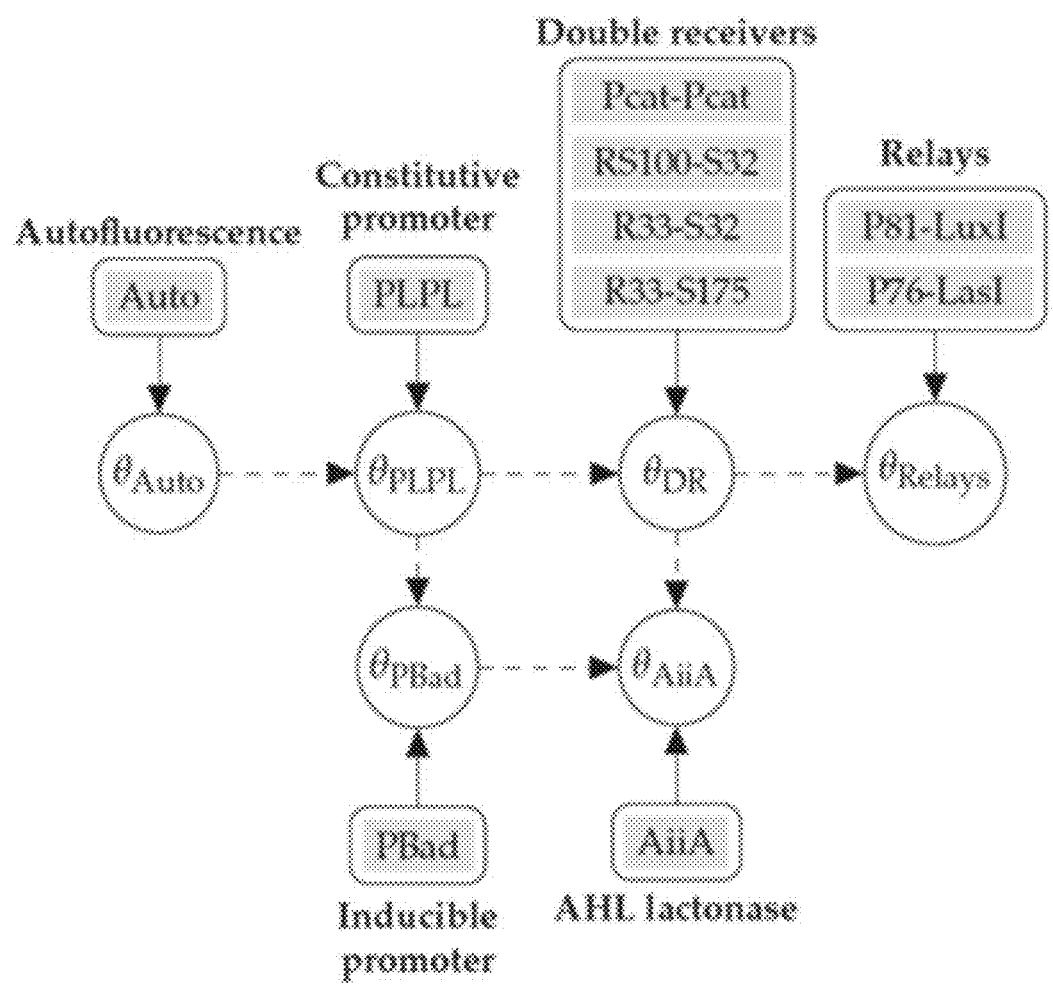
FIG. 8 Dependency graph for circuit parameters (white circles) and collections of circuit measurements (grey boxes enclosed in rounded rectangles). Each inference task is indicated by a solid arrow, representing the approximation of P (θ|Data, H) where H is the modelling hypothesis being used.

We describe herein how dynamic characterisation can be applied in a sequential manner to measurements of circuits of increasing complexity. Parameters of one circuit can be reused in models of circuits that embed components of the upstream circuit (FIG. 4B-D), by propagating the posterior marginal distributions of the upstream circuit parameters as priors of the downstream circuit parameters. For the six circuits shown in FIG. 5A-F, the dependency graph is non-trivial (FIG. 8), but acyclic, as is necessary for this approach. The alternative strategy to a graph-based approach would be to simultaneously parameterize the models of each circuit in a single application of dynamic characterisation. With the graph method one should only marginalize over MCMC chains that have reached the same local maximum of the likelihood function, and discard those stuck in other local maxima. With the A comparison of the two methods can be seen in FIGS. 6G and H.

Methods

Method for Obtaining Measurements of Synthetic Gene Circuits in a Microplate Fluorometer.

Plate fluorometer assays were conducted as previously described by Grant et al., (Mol Syst Biol. (2016) 12(1): 849, 2016). Briefly, overnight cultures of cells containing constitutive chromosomal mRFP1 and the plasmid construct of interest were diluted 1:100, grown to an OD of approximately 0.5, then diluted 1:1000 into M9 supplemented with 0.2% casamino acids and 0.4% glucose. 200 μl of culture was aliquoted into each well and measurements were taken every 10 min for 1,000-2,000 min in a BMG FLUOstar Omega plate fluorometer. 3-oxohexanoyl-homoserine lactone (3OC6HSL, Cayman Chemicals) and 3-oxododecanoyl-homoserine lactone (3OC12HSL, Cayman Chemicals) were dissolved to a concentration of 200 mM in DMSO then 3OC6HSL was diluted in supplemented M9 medium to the concentrations described, while 3OC12HSL, due to its limited solubility in aqueous media, was first diluted 1:50 in ethanol then diluted in supplemented M9 medium to the concentrations described. A 1M arabinose (Sigma) stock solution was made in water, filter sterilized, and diluted in supplemented M9 medium to the concentrations described. HSL receiver and sender plasmids were previously described (Mol Syst Biol. (2016) 12(1): 849, 2016), and all other plasmids were constructed using Gibson Assembly (Gibson et al., Nature Methods, 6(5): 343-345, May 2009) from parts obtained from the MIT Registry of Standard Biological Parts (http://partsregistry.org)

Example 1—No Plasmid (Auto)

Figure 9:
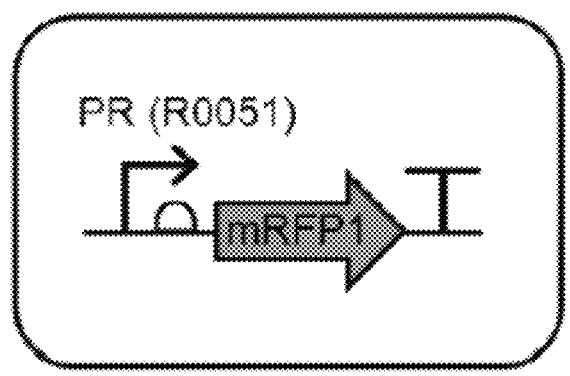
FIG. 9 shows circuit design of chromosomal RFP.

The simplest possible cell line to characterise is one in which there is no synthetic gene circuit at all. How-ever, applying dynamic characterisation to no circuit is useful to characterise how autofluorescence de-pends on cell density and gene expression capacity. Therefore, our chromosomal RFP-expressing cells were measured under a range of conditions, to explore how gene expression capacity influenced time-series measurements at fluorescence wavelengths corresponding to eYFP and eCFP. Design of chromosomal RFP circuit is shown in FIG. 9.

Model Definition

The model we used for autofluorescence assumes that the rate of autofluorescence is proportional to gene expression capacity, h(c), and that the fluorescent material dilutes with cell growth. Bulk autofluorescence is then quantified in exactly the same way as it is when there is a synthetic gene circuit inside the cells. As such, the equations for intracellular autofluorescence corresponding to eYFP and eCFP are $$\frac{dc}{dt} = \gamma(c) \cdot c \tag{1a}$$

$$\frac{d[F_{530}]}{dt} = a_{530} \cdot h(c) - \gamma(c)[F_{530}] \tag{1b}$$

$$\frac{d[F_{480}]}{dt} = a_{480} \cdot h(c) - \gamma(c)[F_{480}] \tag{1c}$$

To compare with experimental measurements, we consider the bulk fluorescence given by $$B_{480} = c \cdot [F_{480}] + B_{480}^{back} \tag{2a}$$

$$B_{530} = c \cdot [F_{530}] + B_{530}^{back} \tag{2b}$$

where $[F_{480}]$ and $[F_{530}]$ are modelled as in back $$B_{610} = ([RFP]) \times c + B_{610}^{back}$$

$$B_{480} = ([CFP] + [F_{480}]) \times c + B_{480}^{back}$$

$$B_{530} = ([YFP] + [F_{530}]) \times c + B_{530}^{back}$$

[YFP] and [CFP] are set to zero, as they are not expressed in this circuit.

Characterisation Experiment

We infer the Auto model parameters by using uniform priors on $\alpha_{480}$, $\alpha_{530}$, $B_{480}^{back}$ and $B_{530}^{back}$. The parameters within y are taken to be the maximum likelihood estimates from the cell density characterisation phase, and the (are either taken to be the maximum likelihood estimates from the control characterisation phase or are inferred within the target phase, depending on the hypothesis in question.

Example 2—Constitutive Expression (PRPR)

Figure 10:
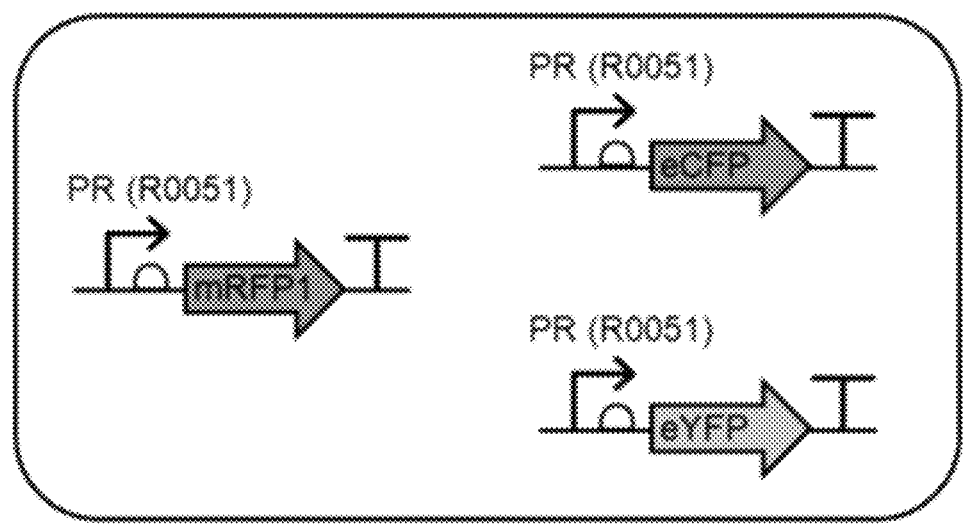
FIG. 10 shows design of constitutive expression circuit.

The simplest circuit that we consider in this article uses constitutive promoters to drive expression of eYFP and eCFP as shown in FIG. 10. Using such a simple circuit enables us to characterise properties of the fluorescent proteins, which can then be reused in to aide characterisation of circuits using the same fluorescent proteins.

Model Definition

As this is the first (non-trivial) synthetic gene circuit that we describe, we include a detailed derivation. We start by considering the chemical reactions introduced by the circuit in FIG. 10.

If we denote by g the plasmid containing the PL:eYFP and PL:eCFP cassettes, then we can write a system of chemical reactions that describe transcription, translation and fluorescent protein maturation as

$$g \xrightarrow{a_{r0011}} g + m\_b0034\_eYFP \tag{3a}$$

$$m\_b0034\_eYFP \xrightarrow{d_{m\_b0034\_eYFP}} \phi \tag{3b}$$

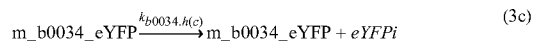
$$m\_b0034\_eYFP \xrightarrow{k_{b0034.h(c)}} m\_b0034\_eYFP + eYFPi \tag{3c}$$

$$eYFPi \xrightarrow{d_{YFP}} \phi \tag{3d}$$

$$eYFPi \xrightarrow{\mu_{YFP}} eYFP \tag{3e}$$

$$eYFP \xrightarrow{d_{YFP}} \phi \tag{3f}$$

$$g \xrightarrow{a_{r0011}} g + m\_b0034\_eCFP \tag{3g}$$

$$m\_b0034\_eCFP \xrightarrow{d_{m\_b0034\_eCFP}} \phi \tag{3h}$$

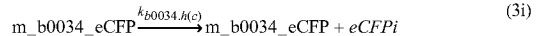
$$m\_b0034\_eCFP \xrightarrow{k_{b0034.h(c)}} m\_b0034\_eCFP + eCFPi \tag{3i}$$

$$eCFPi \xrightarrow{d_{CFP}} \phi \tag{3j}$$

$$eCFPi \xrightarrow{\mu_{CFP}} eCFP \tag{3k}$$

$$eCFP \xrightarrow{d_{CFP}} \phi \tag{3l}$$

where h(c) is the gene expression capacity, as introduced above in the detailed description.

Translating to ODEs, and replacing [g] with N, the plasmid copy number, we obtain $$\frac{dc}{dt} = \gamma(c) \cdot c \qquad (4a)$$

$$\frac{d[m\_b0034\_eYFP]}{dt} = \qquad (4b)$$
$$a_{r0011} \cdot N - (d_{m\_b0034\_eYFP} + \gamma(c))[m\_b0034\_eYFP]$$

$$\frac{d[eYFPi]}{dt} = \qquad (4c)$$
$$k_{b0034} \cdot h(c) \cdot [m\_b0034\_eYFP] - (d_{YFP} + \mu_{YFP} + \gamma(c))[eYFP]$$

$$\frac{d[eYFP]}{dt} = \mu_{YFP}[eYFPi] - (d_{YFP} + \gamma(c))[eYFP] \qquad (4d)$$

$$\frac{d[m\_b0034\_eCFP]}{dt} = a_{r0011} \cdot N - d_{m\_b0034\_eCFP}[m\_b0034\_eCFP] \qquad (4e)$$

$$\frac{d[eCFPi]}{dt} = \qquad (4f)$$
$$k_{b0034} \cdot h(c) \cdot [m\_b0034\_eCFP] - (d_{CFP} + \mu_{CFP} + \gamma(c))[eCFPi]$$

$$\frac{d[eCFP]}{dt} = \mu_{YFP}[eCFPi] - (d_{CFP} + \gamma(c))[eCFP] \qquad (4g)$$

where $\gamma(c)$ is the cellular dilution of each molecular concentration.

Assumption 1: By assuming that mRNA dynamics are fast, we can remove the mRNA species from the model entirely. That is, we equate (4b) and (4e) to zero, solve for [m_b0034_eYFP] and [m_b0034_eCFP], and then substitute into the remaining equations. This results in a reduced model.

$$\frac{dc}{dt} = \gamma(c) \cdot c \qquad (5a)$$

$$\frac{d[eYFPi]}{dt} = a_{YFP} \cdot h(c) - (d_{YFP} + \mu_{YFP} + \gamma(c))[eYFP] \qquad (5b)$$

$$\frac{d[eYFP]}{dt} = \mu_{YFP}[eYFPi] - (d_{YFP} + \gamma(c))[eYFP] \qquad (5c)$$

$$\frac{d[eCFPi]}{dt} = a_{CFP} \cdot h(c) - (d_{CFP} + \mu_{CFP} + \gamma(c))[eYFPi] \qquad (5d)$$

$$\frac{d[eCFP]}{dt} = \mu_{CFP}[eCFPi] - (d_{CFP} + \gamma(c))[eCFP] \qquad (5e)$$

where $$a_{YFP} = \frac{a_{r0011} \cdot N \cdot k_{b0034}}{d_{m\_b0034\_eYFP} + \gamma(c)} \approx \frac{a_{r0011} \cdot N \cdot k_{b0034}}{d_{m\_b0034\_eYFP}}, \qquad (6)$$

$$a_{CFP} = \frac{a_{r0011} \cdot N \cdot k_{b0034}}{d_{m\_b0034\_eCFP} + \gamma(c)} \approx \frac{a_{r0011} \cdot N \cdot k_{b0034}}{d_{m_{b0034_{eCFP}}}}$$

Here we remove $\gamma(c)$ from the denominator because dilution will normally be slower than mRNA degradation, and making this simplification results in $\alpha_{YFP}$ and $\alpha_{CFP}$ being constant. Finally, we note here that despite simplifying the parameterisation (removing $\alpha_{r0011}$, $k_{b0034}$, $d_{m\_b0034\_eYFP}$, and $d_{m\_b0034\_eCFP}$), we should keep in mind that there is a dependency of $a_{YFP}$ and $a_{CFP}$ on the biological parts in each cassette.

Assumption 2: By assuming that fluorescent protein maturation is fast, we can remove the equations for the concentration of immature fluorescent proteins. Let [YFP] be the sum of the concentrations of immature and mature fluorescent proteins. Adding (5b) to (5c), we obtain $$\frac{d}{dt}([eYFPi] + [eYFP]) = a_{YFP} \cdot h(c) - (d_{YFP} + \gamma(c))([eYFPi] + [eYPF]) \qquad (7)$$

$$\Rightarrow \frac{d[YFP]}{dt} = a_{YFP} \cdot h(c) - (d_{YFP} + y(c))[YFP]$$

and similarly for CFP. If we assume that the immature form is instantly converted to the mature form, then the concentration of the mature form is equal to the total concentration. Therefore, the resultant system of equations is given by $$\frac{dc}{dy} = \gamma(c) \cdot c \qquad (8a)$$

$$\frac{d[YFP]}{dt} = a_{YFP} \cdot h(c) - (d_{YFP} + y(c))[YFP] \qquad (8b)$$

$$\frac{d[CFP]}{dt} = a_{CFP} \cdot h(c) - (d_{CFP} + y(c))[CFP] \qquad (8c)$$

Parameter Prior for Target Characterisation Phase

We infer the PRPR model parameters by using (uninformative) uniform priors on the previously uncharacterised parameters $\alpha_{CFP}$, $\alpha_{YFP}$, $d_{CFP}$ and $d_{YFP}$, and (informative) truncated Gaussian priors on $\alpha_{480}$ and $\alpha_{530}$, with mean and standard deviation taken from the marginal posteriors of the Auto circuit characterisation. We also use uninformative priors on the $B_k^{back}$ parameters, without propagating their marginal posteriors from previous circuits.

Characterisation Experiment

We measured the PRPR circuit in response to varying concentrations of chloramphenacol, an inhibitor of protein translation. By inhibiting protein translation, we directly alter the gene expression capacity term in our models, enabling us to test whether h(c) can capture such an effect implicitly.

Example 3 Dynamic Characterisation of the Acyl Homoserine Lactone (AHL) Double Receiver (DR)

In this example we consider the dynamic characterisation of the AHL double receiver device introduced by Grant et al., (Mol Syst Biol. (2016) 12: 849). In this device, two variations of the wild-type $P_{Lux}$ promoter, $P_{OLux}$ and $P_{OLas}$, were engineered to bind preferentially to activated luxR and lasR complexes respectively. As LuxR favours binding of C6 homoserine lactone (3OC6-HSL) and LasR favours binding of C12 homoserine lactone (3OC12-HSL), optimised expression of LuxR and LasR can lead to near-orthogonal intracellular detection of C6-HSL and C12-HSL. The double receiver device was originally measured with $P_{OLux}$ upstream of the coding sequence for cyan fluorescent protein (CFP), and $P_{OLas}$ upstream of the coding sequence for yellow fluorescent protein (YFP). A plasmid containing all of this machinery was then inserted into cells chromosomally expressing monomeric red fluorescent protein (mRFP1), which could be used as a ratiometric control. The model we consider here builds on previously defined/parameterized models, but incorporates two important differences:

1. The concentrations of luxR and lasR become dynamic quantities, and are affected by dilution; and
2. luxR and lasR-based regulators (bound to HSLs) might bind to more than one promoter Example 3.1

We start by considering each HSL denoted by subscript k∈{6, 12}, luxR and lasR, and the presence of two different populations of $P_{Lux}$ promoters. Therefore, we start with the following equations:

$$\frac{d[R]}{dt} = a_R + u_{Rk}[R_k] - [R](\gamma + b_{Rk}[C_k])$$

$$\frac{d[S]}{dt} = a_S + u_{Sk}[S_k] - [S](\gamma + b_{Sk}[C_k])$$

$$\frac{d[R_k]}{dt} = b_{Rk}[R][C_k] + 2u_{Dk}[D_k] - [R_k](\gamma + u_{Rk} + 2b_{Dk}[R_k])$$

$$\frac{d[S_k]}{dt} = b_{Sk}[S][C_k] + 2u_{Ek}[E_k] - [S_k](\gamma + u_{Sk} + 2b_{Ek}[S_k])$$

$$\frac{d[D_k]}{dt} = b_{Dk}[R_k]^2 + u_{GDk}\sum_i [G_i \cdot D_k] - [D_k]\left(u_{Dk} + b_{GDk}\sum_i [G_i]\right)$$

$$\frac{d[E_k]}{dt} = b_{Ek}[S_k]^2 + u_{GEk}\sum_i [G_i \cdot E_k] - [E_k]\left(u_{Ek} + b_{GEk}\sum_i [G_i]\right)$$

$$\frac{d[G_i \cdot D_k]}{dt} = b_{GDk}[G_i][D_k] - u_{GDk}[G_i \cdot D_k]$$

$$\frac{d[G_i \cdot E_k]}{dt} = b_{GEk}[G_i][E_k] - u_{GEk}[G_i \cdot E_k]$$

$$\frac{d[G_i]}{dt} = u_{GDk}[G_i \cdot D_k] + u_{GEk}[G_i \cdot E_k] - [G_i](b_{GDk}[D_k] + b_{GEk}[E_k])$$

Here, $R_k$ refers to a luxR-HSL heterodimer and $D_k$ is the tetrameric complex comprising two $R_k$ complexes (no cross-binding of C6 and C12 dimers). Similarly, $S_k$ and $E_k$ are equivalent lasR-HSL complexes.

Solving most of the above system equal to zero, we obtain the quasi-equilibrium equilibrium $$[G_i \cdot D_k]^* = K_{GDk}[G_i][D_k], \quad [D_k]^* = K_{Dk}[R_k]^2, \quad [R_k]^* = K_{Rk}[R][C_k]$$

Where $$K_{Rk} = \frac{b_{Rk}}{\gamma + \mu_{Rk}}, \quad K_{Dk} = \frac{b_{Dk}}{\mu_{Dk}} \text{ and } K_{GDk} = \frac{b_{GDk}}{\mu_{GDk}}.$$

Therefore (also symmetry of R and S), $$[G_i \cdot D_k]^* = K_{GDk}K_{Dk}\left(\frac{K_{Rk}[C_k]r}{1 + K_{Rk}[C_k]}\right)^2$$

$$[G_i \cdot E_k]^* = K_{GEk}K_{Ek}\left(\frac{K_{Sk}[C_k]s}{1 + K_{Sk}[C_k]}\right)^2$$

where the new K's are defined as above, and $s=n_S/\gamma$.

By taking advantage of the conservation law $[G_i]+[G_i \cdot D_6]+[G_i \cdot D_{12}]+[G_i \cdot E_6]+[G_i \cdot E_{12}]=N$, we can derive the rate of production of mRNA as a function of $[R]$, $[S][C_6]$ and $[C_2]$ as $$\frac{a_0 + a_{Rk}K_{GRk}\left(\frac{K_{Rk}C_k r}{1+K_{Rk}C_k}\right)^2 + a_{Sk}K_{GSk}\left(\frac{K_{Sk}C_k s}{1+K_{Sk}C_k}\right)^2}{1 + K_{GRk}\left(\frac{K_{Rk}C_k r}{1+K_{Rk}C_k}\right)^2 + K_{GSk}\left(\frac{K_{Sk}C_k s}{1+K_{Sk}C_k}\right)^2}$$

where $K_{GRk} = K_{GDk}K_{Dk}$ and $K_{GSk} = K_{GEk}K_{Ek}$.

As before, we replace the exponent 2 of the HSL concentration with a parameter to-be-inferred, giving $$\frac{a_0 + a_{Rk}K_{GRk}r^2\left(\frac{K_{Rk}C_k}{1+K_{Rk}C_k}\right)^n + a_{Sk}K_{GSk}s^2\left(\frac{K_{Sk}C_k}{1+K_{Sk}C_k}\right)^n}{1 + K_{GRk}r^2\left(\frac{K_{Rk}C_k}{1+K_{Rk}C_k}\right)^n + K_{GSk}s^2\left(\frac{K_{Sk}C_k}{1+K_{Sk}C_k}\right)^n}$$

Accordingly, we obtain the following system of equations $$\frac{dx}{dt} = rx\left(1 - \frac{x}{K}\right)$$

$$\frac{d[luxR]}{dt} = a_R \cdot \xi(x) - (d_R + \gamma)[luxR]$$

$$\frac{d[lasR]}{dt} = a_S \cdot \xi(x) - (d_R + \gamma)[lasR]$$

$$\frac{d[CFP]}{dt} = a_C \cdot \xi(x) \cdot f_{76}([C_6], [C_{12}], [luxR], [lasR]) - (d_{CFP} + \gamma)[CFP]$$

$$\frac{d[YFP]}{dt} = a_Y \cdot \xi(x) \cdot f_{81}([C_6], [C_{12}], [luxR], [lasR]) - (d_{YFP} + \gamma)[YFP]$$

where $$f_{p(r,s,c_6 c_{12})} = \frac{a_0^{(p)} + a_1^R K_{GR}^{(p)} r^2 \frac{K_{R6}^n c_6^n + K_{R12}^n c_{12}^n}{(1+K_{R6}c_6+K_{R12}c_{12})^n} + a_1^S K_{GS}^{(p)} s^2 \frac{K_{S6}^n c_6^n + K_{S12}^n c_{12}^n}{(1+K_{S6}c_6+K_{S12}c_{12})^n}}{1 + K_{GR}^{(p)} r^2 \frac{K_{R6}^n c_6^n + K_{R12}^n c_{12}^n}{(1+K_{R6}c_6+K_{R12}c_{12})^n} + K_{GS}^{(p)} s^2 \frac{K_{S6}^n c_6^n + K_{S12}^n c_{12}^n}{(1+K_{S6}c_6+K_{S12}c_{12})^n}}$$

Example 3.2

Model Definition

Figure 11:
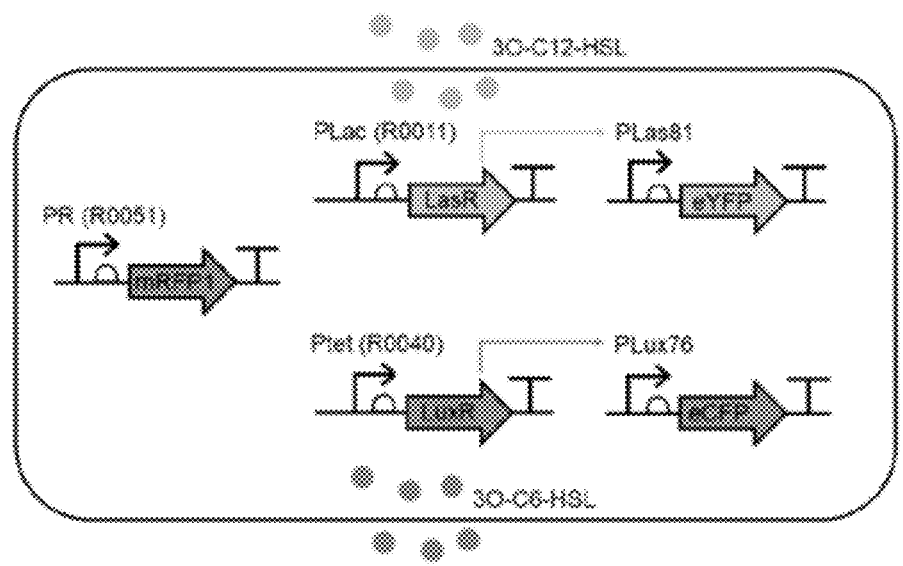
FIG. 11 shows the design of an AHL double receiver (DR) gene circuit.

As the modelling philosophy we are considering here describes dynamics of proteins, the model of DR circuits in this paper differs from model described previously (Grant et al., Mol. Sys. Biol. (2016) 12:849) as the concentrations of luxR and lasR become dynamic quantities affected by growth dilution. Furthermore, in Grant et al., we parameterised the double receiver by first parameterising circuits that only have one $P_{Lux}$ promoter. Here, we seek to parameterise the DR circuits directly, by inferring parameters against YFP and CFP measurements simultaneously. As such, the model must consider that luxR and lasR-based regulators (bound to HSLs) might bind to more than one ($P_{Lux}$) promoter. FIG. 11 shows the design of the double receiver circuit.

We denote by $C_k$ the HSL molecule with length k carbon chain, and by $G_i$ the pLux76 and pLas81 promoters. Then we can specify all of the reactions between the HSLs, luxR and lasR, and eventual binding of transcriptional regulators to the $P_{OLux}$ and $P_{OLas}$ promoters.

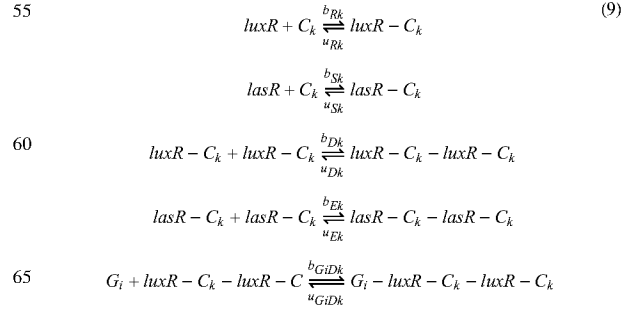

(9)

$$G_i + lasR - C_k - lasR - C_k \underset{u_{GiEk}}{\overset{b_{GiEk}}{\rightleftharpoons}} G_i - lasR - C_k - lasR - C_k$$

Constitutive expression of luxR, lasR is described by $$\emptyset \xrightarrow{a_{luxR}} luxR \quad \emptyset \xrightarrow{a_{lasR}} lasR \tag{10}$$

Inducible expression of eCFP and eYFP by $P_{OLux}$ and $P_{OLas}$ respectively is described by $$G_{pLux76} \xrightarrow{a0_{pLux76}} G_{pLux76} + m\_b0034\_eCFP \tag{11}$$

$$G_{pLux76} - luxR - C_k - luxR - C_k \xrightarrow{a1_{pLux76}} G_{pLux76} - luxR - C_k - luxR - C_k + m\_b0034\_eCFP$$

$$G_{pLux76} - lasR - C_k - lasR - C_k \xrightarrow{a1_{pLux76}} G_{pLux76} - lasR - C_k - lasR - C_k + m\_b0034\_eCFP$$

$$G_{pLas81} \xrightarrow{a0_{pLas81}} G_{pLas81} + m_{b0034_{eCFP}}$$

$$G_{pLas81} - luxR - C_k - luxR - C_k \xrightarrow{a0_{pLas81}} G_{pLas81} - luxR - C_k - luxR - C_k + m\_b0034\_eYFP$$

$$G_{pLas81} - lasR - C_k - lasR - C_k \xrightarrow{a1_{pLas81}} G_{pLas81} - lasR - C_k - lasR - C_k + m\_b0034\_eCFP$$

The full DR circuit comprises reactions (9), (10) and (11), and the same reactions as shown for the PLPL circuit that describe mRNA translation for eCFP and eYFP.

To produce a simplified ODE model amenable to parameter inference, we start with the equations describing luxR and lasR protein, their complexes involving $C_6$ and $C_{12}$, and the bound/unbound promoters.

Applying also Assumption 1 from before, we arrive a set of equations for the non-mRNA species as $$\frac{dc}{dt} = \gamma(c) \cdot c \tag{12a}$$

$$\frac{d[luxR]}{dt} = a_R + u_{Rk}[luxR - C_k] - [luxR](\gamma(c) + d_R + b_{Rk}[C_k]) \tag{12b}$$

$$\frac{d[lasR]}{dt} = a_S + u_{Sk}[lasR - C_k] - [lasR](\gamma(c) + d_S + b_{Sk}[C_k]) \tag{12c}$$

$$\frac{d[luxR - C_k]}{dt} = b_{Rk}[luxR][c_k] + 2u_{Dk}[luxR - C_k - luxR - C_k] - [luxR - C_k](\gamma(c) + d_R^1 + u_{Rk} + 2b_{Dk}[luxR - C_k]) \tag{12d}$$

$$\frac{d[lasR - C_k]}{dt} = b_{Sk}[lasR][c_k] + 2u_{Ek}[lasR - C_k - lasR - C_k] - [lasR - C_k](\gamma(c) + d_S^1 + u_{Sk} + 2b_{Ek}[lasR - C_k]) \tag{12e}$$

$$\frac{d[luxR - C_k - luxR - C_k]}{dt} = b_{Dk}[luxR - C_k]^2 + \tag{12f}$$

$$u_{GiDk}\sum_i[G_i - luxR - C_k - luxR - C_k] \ldots - [luxR - C_k - luxR - C_k]$$

$$\left(\gamma(c) + d_R^1 + u_{Dk} + b_{GiDk}\sum_i[G_i]\right)$$

$$\frac{d[lasR - C_k - lasR - C_k]}{dt} = b_{Ek}[lasR - c_k]^2 + \tag{12g}$$

$$u_{GiEk}\sum_i[G_i - lasR - C_k - lasR - C_k] \ldots - [lasR - C_k - lasR - C_k]$$

$$\left(\gamma(c) + d_R^1 + u_{Ek} + b_{GiEk}\sum_i[G_i]\right)$$

$$\frac{d[G_i - luxR - C_k - luxR - C_k]}{dt} = \tag{12h}$$

$$b_{GiDk}[G_i][luxR - C_k - luxR - C_k] -$$

$$(\gamma(c) + u_{GiDk})[G_i - luxR - C_k - luxR - C_k]$$

$$\frac{d[G_i - lasR - C_k - lasR - C_k]}{dt} = \tag{12i}$$

$$b_{GiEk}[G_i][lasR - C_k - lasR - C_k] -$$

$$(\gamma(c) + u_{GiEk})[G_i - lasR - C_k - lasR - C_k]$$

$$\frac{d[G_i]}{dt} = \gamma(c) \cdot n_G + u_{GiDk}[G_i - luxR - C_k - luxR - C_k] + \tag{12j}$$

$$u_{GiEk}[G_i - lasR - C_k - lasR - C_k] \ldots - [G_i](\gamma(c) +$$

$$b_{GiDk}[luxR - C_k - luxR - C_k] + b_{GiEk}[lasR - C_k - lasR - C_k])$$

Here, luxR-$C_k$ refers to a luxR-HSL heterodimer and luxR-$C_k$-luxR-$C_k$ is the tetrameric complex comprising two luxR-$C_k$ complexes (no cross-binding of C6 and C12 dimers). Similarly, lasR-$C_k$ and lasR-$C_k$-lasR-$C_k$ are equivalent lasR-HSL complexes. The luxR and lasR proteins are assumed to be stabilised by the binding of signal. Therefore, rates $d^1_j < d_j (j=R,S)$ are the slower rates for signal-bound luxR/lasR proteins.

Solving most of the above system equal to zero, we obtain the quasi-equilibrium $$[G_i - luxR - C_k - luxR - C_k]^* = K_{GDk}[G_i][luxR - C_k - luxR - C_k] \tag{13a}$$

$$[luxR - C_k - luxR - C_k]^* = K_{Dk}[luxR - C_k]^2 \tag{13b}$$

$$[luxR - C_k]^* = K_{Rk}[G_i][luxR][C_k] \tag{13c}$$

where $$K_{Rk} = \frac{b_{Rk}}{\gamma + u_{Rk}}, K_{Dk} = \frac{b_{Dk}}{u_{Dk}} \text{ and } K_{GiDk} = \frac{b_{GiDk}}{u_{GiDk}}$$

Therefore (also symmetry of luxR and lasR), $$[G_i\text{-luxR-}C_k\text{-luxR-}C_k]^* = K_{GiDk}K_{Dk}(K_{Rk}[C_k][luxR])^2 \tag{14a}$$

$$[G_i\text{-lasR-}C_k\text{-lasR-}C_k]^* = K_{GiEk}K_{Ek}(K_{Sk}[C_k][lasR])^2 \tag{14b}$$

where the new K's are defined as above.

In the reduced system, total luxR is described by the equations $$\frac{d[luxR]_T}{dt} = \tag{15a}$$

$$\frac{d[luxR]}{dt} + \sum_k \left(\frac{d[luxR - C_k]}{dt} + 2\frac{d[luxR - C_k - luxR - C_k]}{dt} + 2\sum_i \frac{d[G_i - luxR - C_k - luxR - C_k]}{dt}\right) = a_R - \gamma[luxR] - d_R[luxR]$$

$$-\sum_k \left((\gamma + d_R^1)[luxR - C_k] + \tag{15b}\right.$$

$$(\gamma + d_R^1)[luxR - C_k - luxR - C_k] + \sum_i[G_i - luxR - C_k - luxR - C_k]\right)$$

$$= a_R - \gamma[luxR]_T - d_R^1[luxR]_T - (d_R - d_R^1)[luxR] \tag{15c}$$

The final term needs careful attention, as we expect a difference between $d_R$ and $d_R^1$. Nevertheless, the obvious approximation is to ignore this difference, and model $[luxR]_T$ explicitly with no dependence on $[R]$. We can write down expressions for the fraction of $[luxR]_T$ that is bound to signal, dimerized, etc., using the equilibrium relationships above. E.g $$[luxR]_T = [luxR] + \sum_k ([luxR-C_k] + 2[luxR-C_k-luxR-C_k] + $$

$$2\sum_i [G_i - luxR-C_k - luxR-C_k])$$

$$= [luxR] + \sum_k (K_{Rk}[luxR][C_k] + 2K_{Dk}K_{Rk}^2[luxR]^2[C_k]^2 +$$

$$\sum_i 2K_{GiDk}[G_i]K_{Dk}K_{Rk}^2[luxR]^2[C_k]^2)$$

When $C_k$ is low, total LuxR is closely approximated by free LuxR, $[luxR]_T \approx [luxR]$. But when $C_k$ is high, $[luxR]_T$ should be partitioned between the $[luxR-C_k-luxR-C_k]$ and $[G_i-luxR-C_k-luxR-C_k]$ species. Therefore, to simplify the analysis, we propose modelling this by using the assumption $$[luxR]_T \approx [luxR] + \sum_k [luxR-C_k] = [luxR]\left(1 + \sum_k K_{Rk}[C_k]\right) \quad (16)$$

which still captures the saturation of luxR by $C_k$, using the approximations $$[luxR] \approx [luxR]_T \cdot \frac{1}{1 + \sum_k K_{Rk}[C_k]} \quad (17a)$$

$$[luxR-C_k] \approx [luxR]_T \cdot \frac{K_{Rk}[C_k]}{1 + \sum_k K_{Rk}[C_k]} \quad (17b)$$

$$[luxR-C_k-luxR-C_k] \approx K_{Dk}[luxR]_T^2 \left(\frac{K_{Rk}[C_k]}{1 + \sum_k K_{Rk}[C_k]}\right)^2 \quad (17c)$$

$$[G_i-luxR-C_k-luxR-C_k] \approx K_{GR}^{(i)}[G_i][luxR]_T^2 \left(\frac{K_{Rk}[C_k]}{1 + \sum_k K_{Rk}[C_k]}\right)^2 \quad (17d)$$

where $$K_{GR}^{(i)} = K_{GiDk}K_{Dk}$$

is assumed to be independent of which signal is bound (k).

The approximation also allows for saturation of $G_i$. By taking advantage of the conservation law $[G_i]+[G_i \cdot luxR-C_6-luxR-C_6]+[G_{12}-luxR-C]-luxR-C]+[G_6-lasR-C]-lasR-C]+[G_{12}-lasR-C]-lasR-C]=N_i$, we can derive the rate of production of mRNA as a function of $[R]_T$, $[S]_T$ $[C_6]$ and $[C_{12}]$. For notational convenience we drop the square brackets and T subscript, which allows us to write $$f_i(R, S, C_6, C_{12}) = \quad (18)$$

-continued $$\frac{\varepsilon^{(i)} + K_{GR}^{(i)}R^2\left(\frac{K_{Rk}C_k}{1+\sum_k K_{Rk}C_k}\right)^{n_R} + K_{GS}^{(i)}S^2\left(\frac{K_{Sk}C_k}{1+\sum_k K_{Sk}C_k}\right)^{n_S}}{1 + K_{GR}^{(i)}R^2\left(\frac{K_{Rk}C_k}{1+\sum_k K_{Rk}C_k}\right)^{n_R} + K_{GS}^{(i)}S^2\left(\frac{K_{Rk}C_k}{1+\sum_k K_{Rk}C_k}\right)^{n_S}}$$

where $K_{G_i\text{-}luxR}$ and $K_{G_i\text{-}lasR}$ are scaled to incorporate $K_{Dk}$ and $K_{Ek}$ respectively, and we introduce alternative exponents $n_R$ and $n_S$. Accordingly, we obtain the following system of equations $$\frac{dc}{dt} = \gamma(c) \cdot c \quad (19a)$$

$$\frac{d[luxR]}{dt} = a_R \cdot h(c) - (d_R + \gamma(c))[luxR] \quad (19b)$$

$$\frac{d[lasR]}{dt} = a_S \cdot h(c) - (d_R + \gamma(c))[lasR] \quad (19c)$$

$$\frac{d[CFP]}{dt} = a_C \cdot h(c) \cdot f_{76}([C_6], [C_{12}], [R], [S]) - (d_{CFP} + \gamma(c))[CFP] \quad (19d)$$

$$\frac{d[YFP]}{dt} = a_Y \cdot h(c) \cdot f_{81}([C_6], [C_{12}], [R], [S]) - (d_{YFP} + \gamma(c))[YFP] \quad (19e)$$

where the variables R and S now represent total luxR and lasR respectively.

Characterisation Experiment

To characterise the LuxR and LasR signalling components, we used measurements of the response of four DR circuits from Grant et al., (Mol. Systems Biol., 2016, 12(1): 849) to treatment with C6-HSL and C12-HSL over 3-fold dilutions. The maximum LuxR and LasR production rates were normalized to the values corresponding to the Pcat promoters, as done previously, thus setting the scale for unobserved concentrations of LuxR and LasR.

We used (uninformative) uniform priors on the previously uncharacterised parameters, and (informative) truncated Gaussian priors on $\alpha_{480}$, $\alpha_{530}$, $d_{CFP}$ and $d_{YFP}$ with mean and standard deviation taken from the marginal posteriors of the PRPR circuit characterisation. We also use uninformative priors on the $B_k^{back}$ parameters, without propagating their marginal posteriors from previous circuits.

Example 4 Dynamic Characterisation of Two Relay Signalling Devices

Figure 2A:
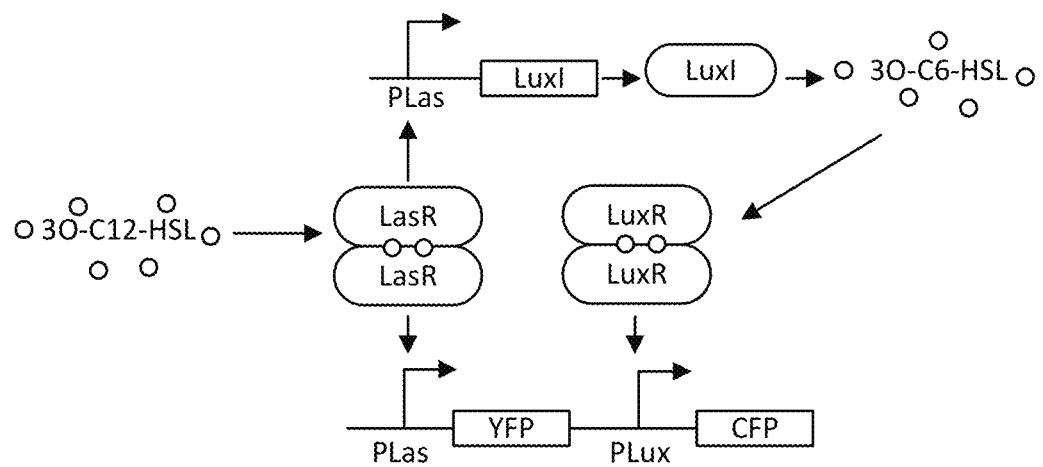
FIGS. 2A and 2B show relay circuit network diagrams.
Figure 2B:
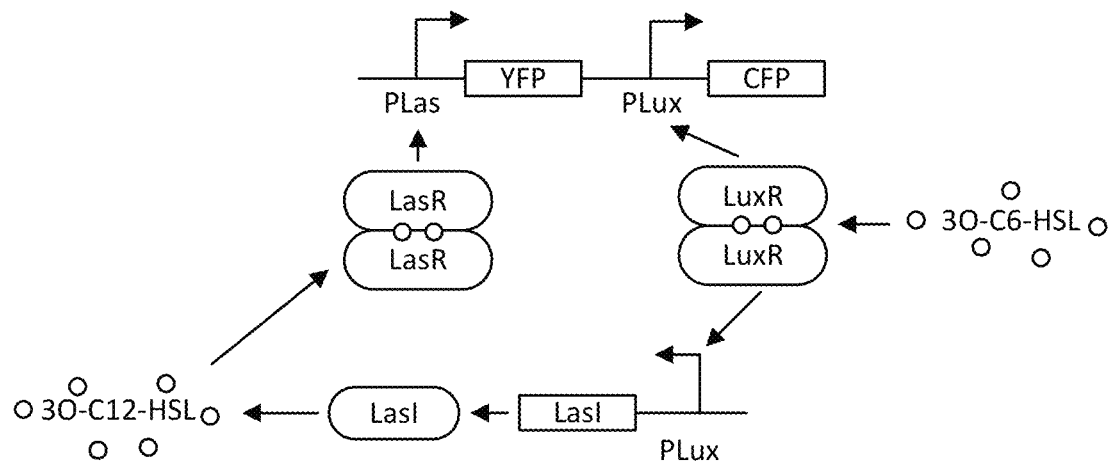

To test more directly the characterisation of dynamics in engineered gene expression circuits, we constructed two relay signalling devices. The first responds to C6-HSL via binding of constitutively expressed LuxR and activation of the engineered $P_{OLux}$ promoter, which synthesizes the C12-HSL-producing LasI enzyme and CFP.C12-HSL is then detected via binding of constitutively expressed LasR and activation of the engineered $P_{OLas}$ promoter, which synthesizes YFP. Accordingly, we can monitor the promoter activity of both stages of the relay. Chromosomally integrated RFP provides a ratiometric control, as before. The second device performs the receive-send receive in the other order, sensing C12-HSL via $P_{OLas}$, which synthesizes the C6-HSL-producing LuxI enzyme (and YFP), with C6-HSL then detected via $P_{OLux}$-CFP. This arrangement is shown in FIGS. 2A and 2B.

The relay circuit network diagrams are also provided in FIGS. 12A and 12B.

Building on the above approach, we can write down an equation for the intracellular production of LuxI or LasI. Each then synthesises C6-HSL and C12-HSL respectively, which we model as a linear function of [luxI] or [lasI]. In the models described above, it was assumed that transport between the intracellular and extracellular components was fast. As there was no de novo synthesis of HSL, and often a large extracellular excess, the system dynamics would unlikely be critically sensitive to this approximation, as any lag could be accounted for by adjustments in the other parameters. However, in the relay circuits, where HSLs are being produced, the transport between intracellular and extracellular compartments must be considered more carefully. For the C6-LuxI-C12 relay, the equations for the mass of each molecule in the intracellular (denoted by subscript i) and extracellular (denoted by subscript e) compartments is given by $$\frac{d(V_i \cdot [lasI])}{dt} = V_i \cdot \xi(x) \cdot \rho_L \cdot f_{76}([C_6], [C_{12}], [luxR], [lasR]) - V_i \cdot d_L[lasI]$$

$$\frac{d(V_i \cdot [C_{12}]_i)}{dt} = V_i \cdot k_{C12} \cdot [lasI] + \eta_{12}([C_{12}]_e - [C_{12}]_i)$$

$$\frac{d(V_e \cdot [C_{12}]_e)}{dt} = \eta_{12}([C_{12}]_i - [C_{12}]_e)$$

where $\rho_L$ is the relative production rate of lasI (relative to CFP production; see above), and $k_{C12}$ is the rate of C12-HSL synthesis by lasI. To arrive at a set of equations for the derivatives of the concentrations of each molecule (in each compartment), we expand the left-hand sides using the chain rule. Then, defining $$\gamma := \frac{1}{V_i}\frac{dV_i}{dt}$$

as the specific growth rate, or dilution factor, assuming that $V_e = V_{tot} - V_i$, and rescaling [lasI] according to $[lasI] = L/\rho_L$ we obtain $$\frac{dL}{dt} = \xi(x) \cdot f_{76}([C_6], [C_{12}], [luxR], [lasR]) - (d_L + \gamma)L$$

$$\frac{d[C_{12}]_i}{dt} = k'_{C12} \cdot L + \frac{\eta_{12}}{V_i}([C_{12}]_e - [C_{12}]_i) - \gamma[C_{12}]_i$$

$$\frac{d[C_{12}]_e}{dt} = \frac{\eta_{12}}{V_{tot} - V_i}([C_{12}]_i - [C_{12}]_e) + \frac{\gamma V_i}{V_{tot} - V_i}$$

where $k'_{C12} = k_{C12}/\rho_L$.

As we had no reliable estimates of HSL transport rates a priori, we started by using the model that combines (19) with (16). However, we also considered the assumption that HSL transport is fast, resulting in the relations $[Ck]_e = [Ck]$ for $k=6, 12$. By summing equations (18b) and (18c), we obtain $$\frac{d(V_{tot} \cdot [C_{12}])}{dt} = \frac{d(V_i \cdot [C_{12}]_i)}{dt} + \frac{d(V_e \cdot [C_{12}]_e)}{dt} = V_i \cdot k_{C12} \cdot [lasI]$$

which when rearranged gives an alternative model (19) as $$\frac{dL}{dt} = \xi(x) \cdot f_{76}([C_6], [C_{12}], [luxR], [lasR]) - (d_L + \gamma)L$$

-continued $$\frac{d[C_{12}]}{dt} = \frac{V_i}{V_{tot}} \cdot k'_{C12} \cdot L$$

with $k'_{C12}$ and L as defined above.

Example 5 Inducible Expression (PBad)

The arabinose-PBad system is commonly used to control expression in synthetic gene circuits. The PBad promoter is part of the arabinose operon, which also involves the araC protein. When arabinose is added to cell cultures at different concentrations, it increases expression of a downstream transcript. In this study, we have used PBad to control AHL lactonase expression (see further below).

To characterise the relationship between PBad and arabinose in vivo, we placed the coding sequence for eYFP downstream of PBad (as shown in FIG. 13) and measured the response to varying concentrations of arabinose.

Example 6 Dynamic Characterisation of AHL Lactonase (AiiA)

AHL molecules can be degraded by AHL lactonase enzymes. The most commonly used lactonase in synthetic biology applications is AiiA (Danino et al., Nature, 2010, 463(7279): 326-330; Chen et al., Science, 2015, 349(6251): 986-989), which originates with *Bacillus thurigensis*. AiiA is mostly non-specific; catalytic activity has been measured against a large variety of AHLs with varying length carbon chains (Liu et al., Biochemistry, 2008, 47(29): 7706-7714).

Figure 3:
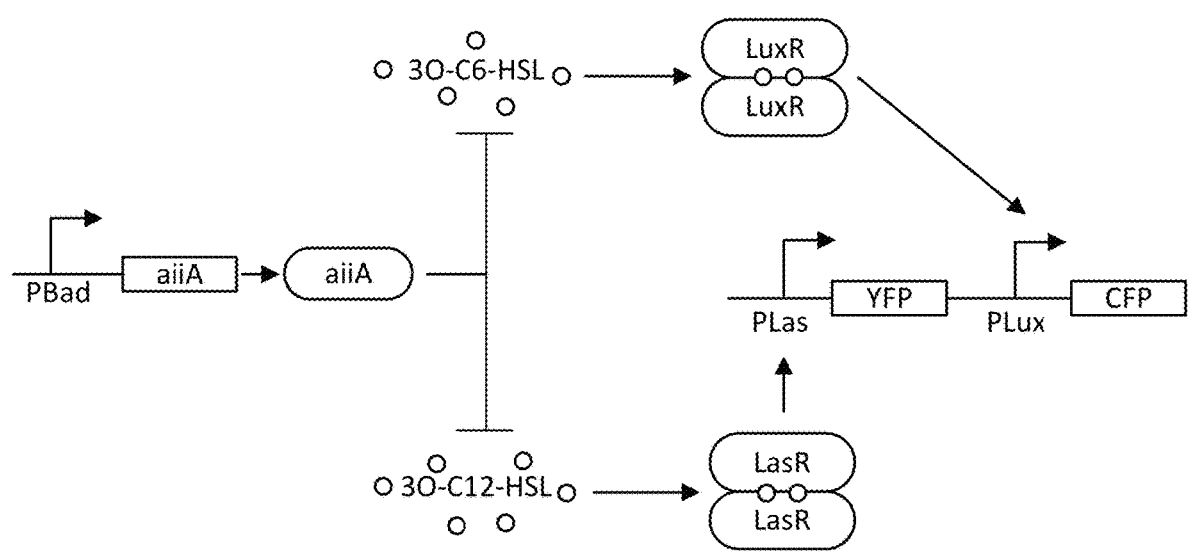
FIG. 3 shows circuit network diagram for the AHL lactonase module.
Figure 4A:
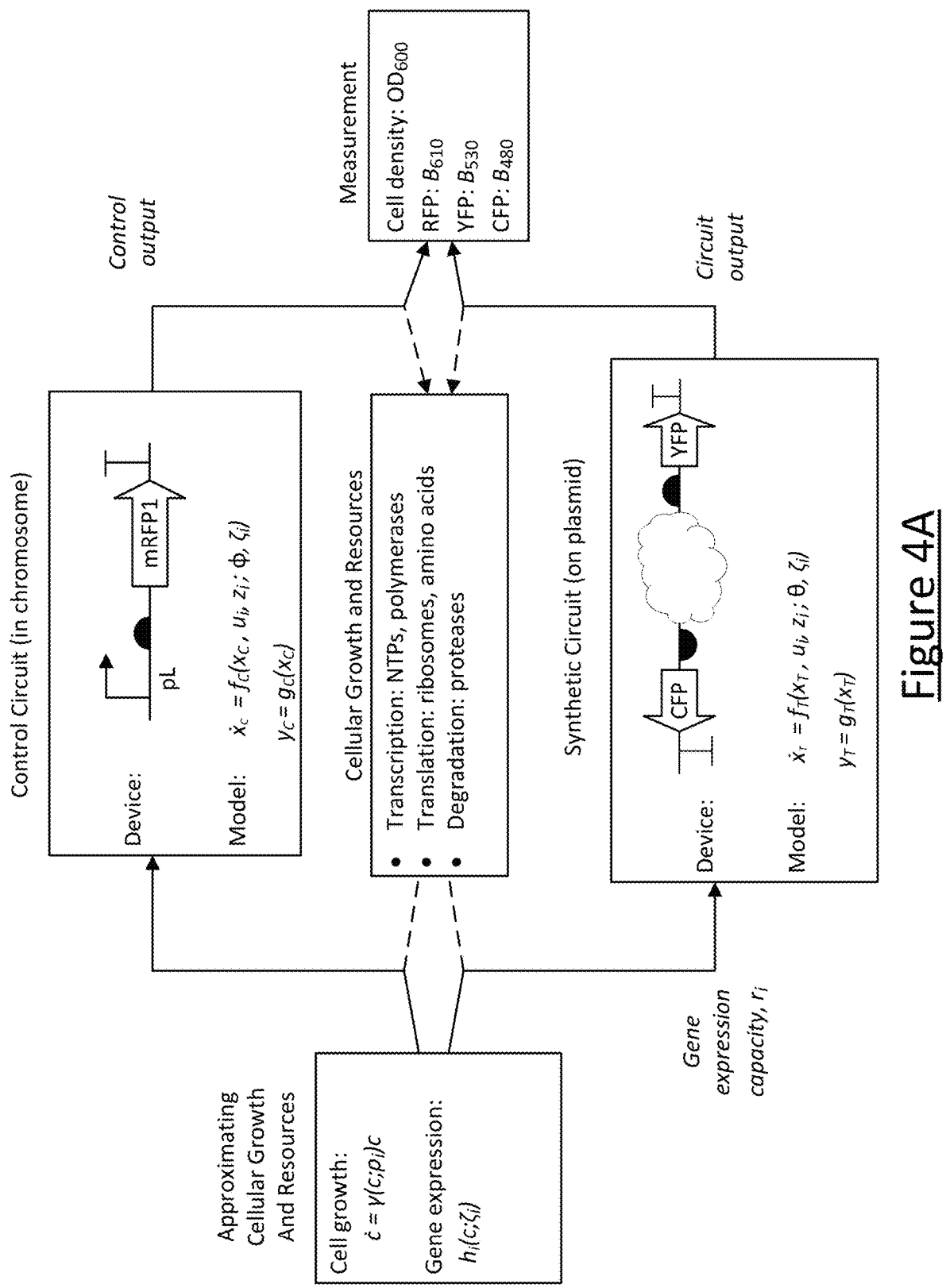
FIGS. 4A to D show a graphical depiction of dynamic characterisation methods of the invention.
Figure 4B:
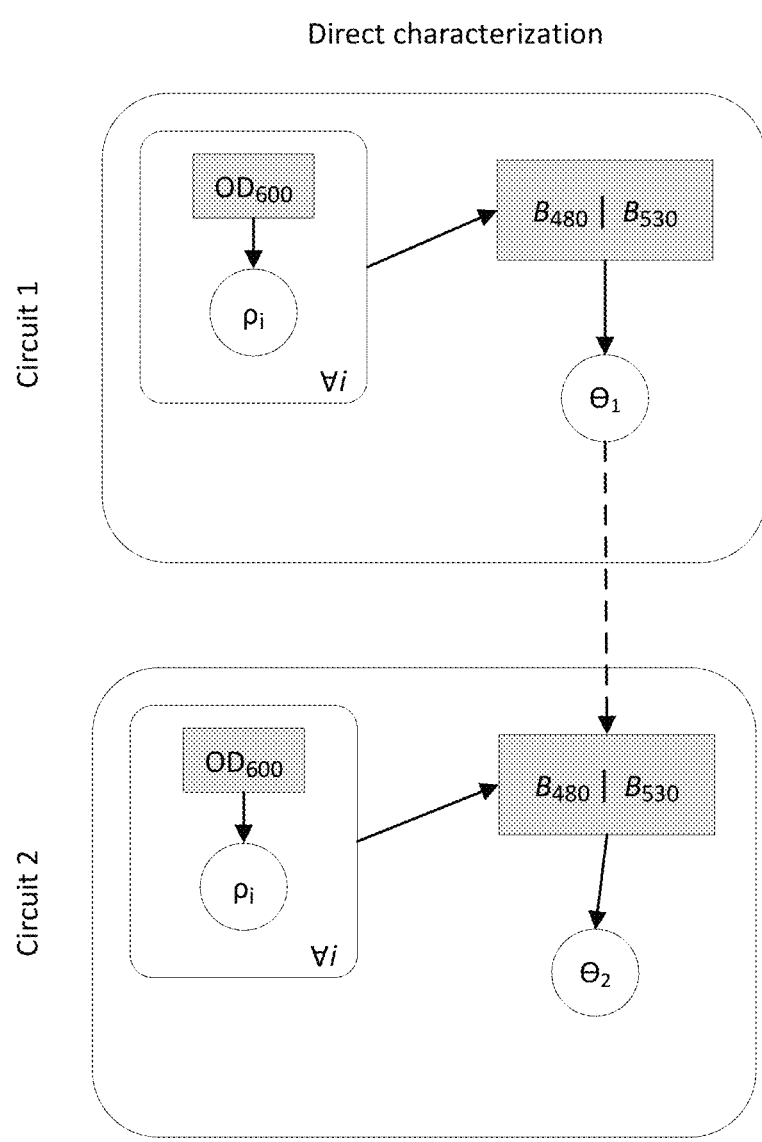
Figure 4C:
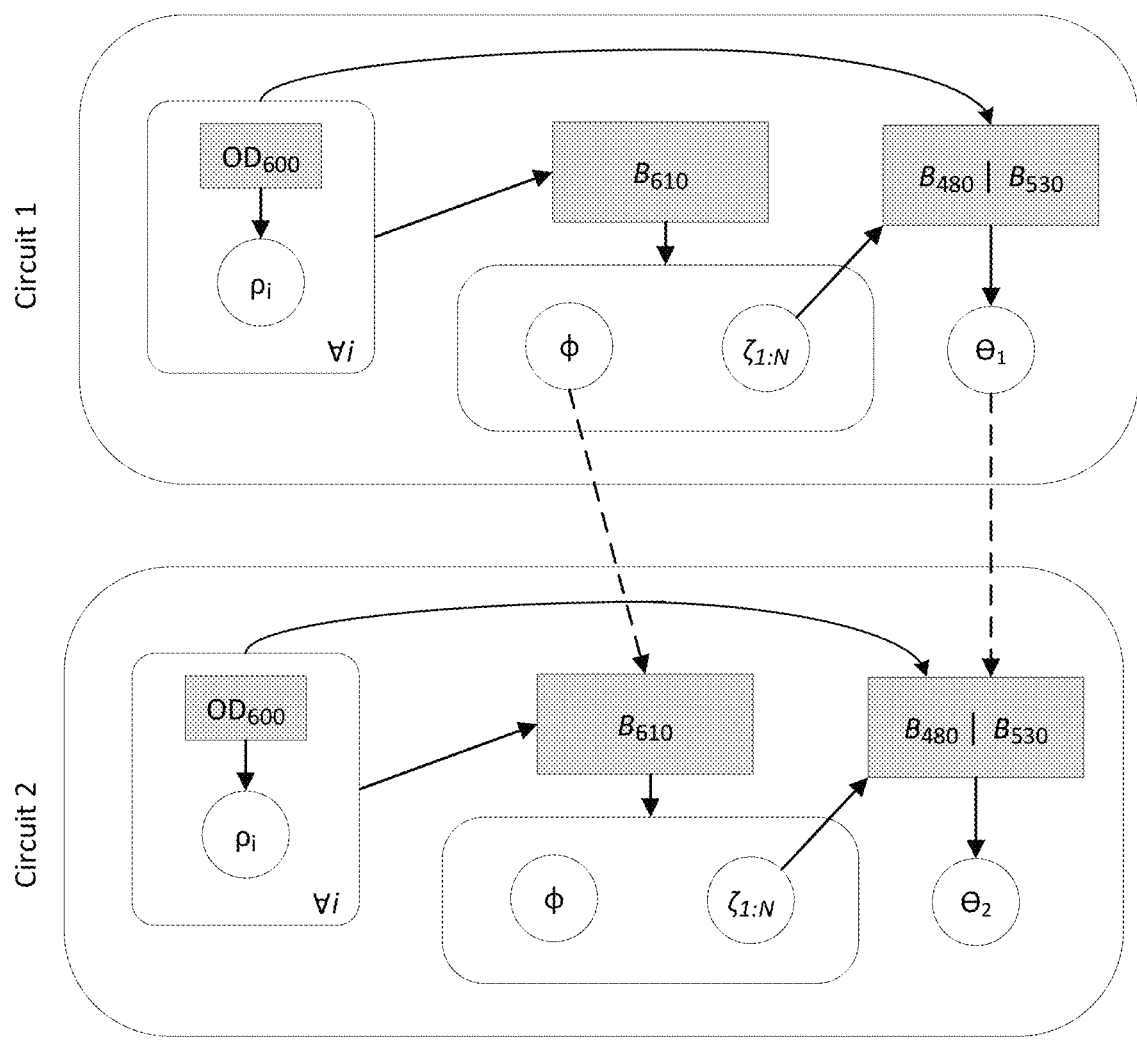
Figure 4D:
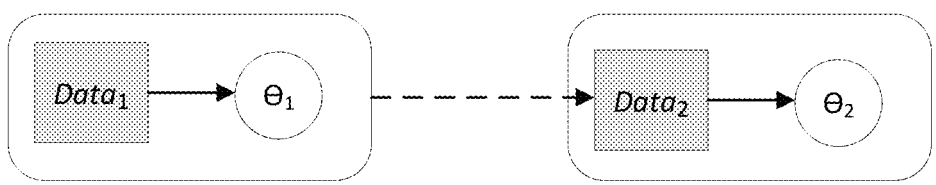
Figure 14:
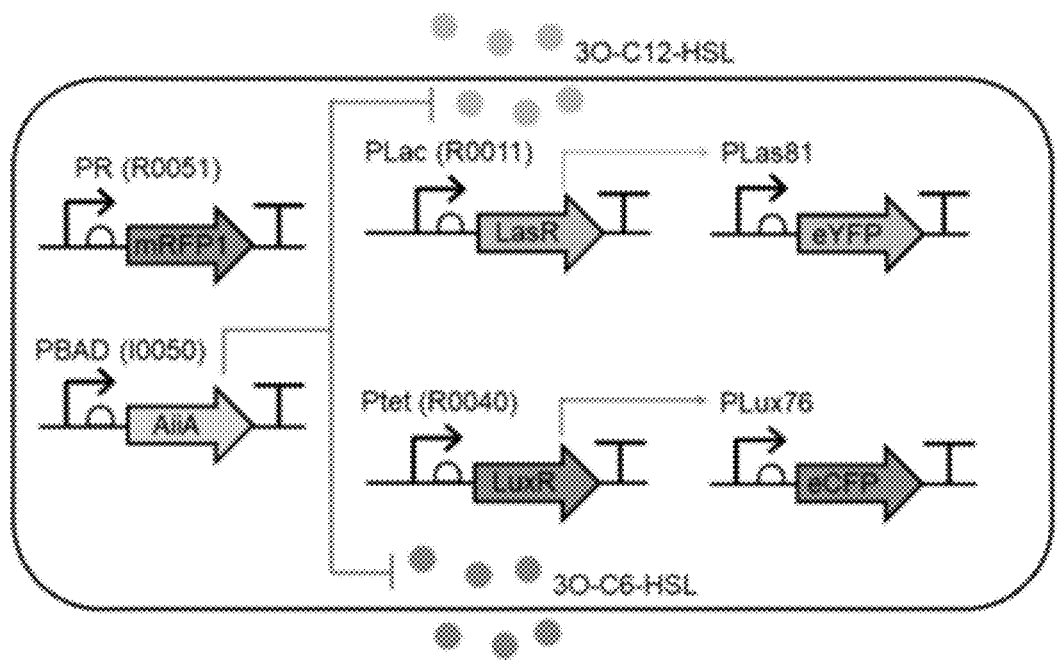
FIG. 14 shows the circuit network diagram for AHL lactonase module.

To characterise the AiiA lactonase activity in a synthetic gene circuit, we expressed AiiA under the control of the arabinose-inducible PBad promoter (as shown in FIG. 3 and in FIG. 14). As AHLs may translocate between cells and the extracellular medium, and AiiA is only expressed inside cells in this strategy, we must carefully consider the volume and concentration of these molecules over time, as before.

Assuming constitutive production, a few reactions describing the production, degradation and catalytic activity of AiiA can be as follows:

(21a)

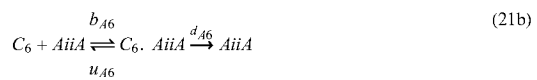
(21b)

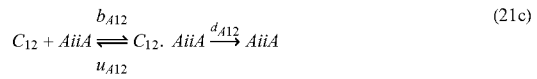
(21c)

Translating these reactions to ordinary differential equations, along with the equations for the double receiver module, we obtain $$\frac{d(V_i \cdot [A])}{dt} = V_i \cdot a_A \cdot f_{Pbad}(Ara) + \quad (22a)$$

$$V_i \cdot (u_{A6} + d_{A6})[A \cdot C_6] + V_i \cdot (u_{A12} + d_{A12})[A \cdot C_{12}]$$

$$-V_i \cdot (d_A + b_{A6}[C_6]_i + b_{A12}[C_{12}]_i)[A] \quad (22b)$$

$$\frac{d(V_i \cdot [C_6]_i)}{dt} = \quad (22c)$$

-continued $$V_i \cdot u_{A6} \cdot [A. \ C_6] + \eta_6([C_6]_e - [C_6]_i) - V_i \cdot (d_C + b_{A6}[A])[C_6]_i$$

$$\frac{d(V_i \cdot [C_{12}]_i)}{dt} = \quad (22d)$$

$$V_i \cdot u_{A12} \cdot [A. \ C_{12}] + \eta_{12}([C_{12}]_e - [C_{12}]_i) - V_i \cdot (d_C + b_{A122}[A])[C_{12}]_i$$

$$\frac{d(V_i \cdot [A. \ C_6])}{dt} = V_i \cdot b_{A6}[A][C_6]_i - V_i \cdot (u_{A6} + d_{A6})[A. \ C_6] \quad (22e)$$

$$\frac{d(V_i \cdot [A. \ C_{12}])}{dt} = V_i \cdot b_{A6}[A][C_{12}]_i - V_i \cdot (u_{A12} + d_{A12})[A. \ C_{12}] \quad (22f)$$

$$\frac{d(V_e \cdot [C_6]_e)}{dt} = \eta_6([C_6]_i - [C_6]_e) \quad (22g)$$

$$\frac{d(V_e \cdot [C_{12}]_e)}{dt} = \eta_{12}([C_{12}]_i - [C_{12}]_e) \quad (22h)$$

We can apply an equilibrium assumption to the AiiA-HSL intermediate by equating (22e) and (22f) to zero. This gives $$[A. \ C_j] = \frac{b_{Aj}}{\gamma + u_{Aj} + k_{Aj}}[A][C_j] \approx \frac{b_{Aj}}{u_{Aj} + k_{Aj}}[A][C_j] \quad (23)$$

where the approximation to suppress $\gamma$ is due to the catalytic activity of AiiA being significantly faster than the dilution rate.

Therefore, depending on the concentrations [C6] and [C12], the lactonase is bound according to the conservation equation $$[A] = [A_f] + [A. \ C_6] + [A. \ C_{12}] = [A] \cdot (1 + K_{A6}[C_6] + K_{A12}[C_{12}]) \quad (24)$$

where $K_{Aj} = \frac{b_{Aj}}{u_{Aj} + k_{Aj}}$.

Alternatively, depending on the concentrations [C6] and [C12], the lactonase is bound according to the conservation equation $$[A_{tot}] = [A] + [A. \ C_6] + [A. \ C_{12}] = [A] \cdot (1 + K_{A6}[C_6] + K_{A12}[C_{12}])$$

where $$K_{Aj} = \frac{b_{Aj}}{u_{Aj} + d_{Aj}}.$$

By cancelling the binding and unbinding terms with AiiA, we are left with the simpler set of equations $$\frac{d(V_i \cdot [A])}{dt} = V_i \cdot a_A \cdot f_{Pbad}(Ara) - V_i \cdot d_A \cdot [A] \quad (25a)$$

$$\frac{d(V_i \cdot [C_6]_i)}{dt} = \quad (25b)$$

$$\eta_6([C_6]_e - [C_6]_i) - V_i \cdot d_{A6} \cdot \frac{[A][C_6]_i}{1 + K_{A6}[C_6]_i + K_{A12}[C_{12}]_i} - V_i \cdot d_C \cdot [C_j]$$

$$\frac{d(V_i \cdot [C_{12}]_i)}{dt} = \eta_{12}([C_{12}]_e - [C_{12}]_i) - \quad (25c)$$

$$V_i \cdot d_{A12} \cdot \frac{[A][C_{12}]_i}{1 + K_{A6}[C_6]_i + K_{A12}[C_{12}]_i} - V_i \cdot d_C \cdot [C_j]$$

$$\frac{d(V_e \cdot [C_6]_e)}{dt} = \eta_6([C_6]_i - [C_6]_e) \quad (25d)$$

$$\frac{d(V_e \cdot [C_{12}]_e)}{dt} = \eta_{12}([C_{12}]_i - [C_{12}]_e) \quad (25e)$$

Or, alternatively, we are left with $$\frac{d(V_i \cdot [A_{Tot}])}{dt} = V_i \cdot a_A \cdot f_{Pbad}(Ara) - V_i \cdot d_A \cdot \frac{[A_{Tot}]}{1 + K_{A6}[C_6] + K_{A12}[C_{12}]}$$

$$\frac{d(V_i \cdot [C_6]_i)}{dt} =$$

$$\eta_6([C_6]_e - [C_6]_i) - V_i \cdot d_{A6} \cdot \frac{[A_{Tot}][C_6]_i}{1 + K_{A6}[C_6]_i + K_{A12}[C_{12}]_i} - V_i \cdot d_C \cdot [C_j]$$

$$\frac{d(V_i \cdot [C_{12}]_i)}{dt} = \eta_{12}([C_{12}]_e - [C_{12}]_i) -$$

$$V_i \cdot d_{A12} \cdot \frac{[A_{Tot}][C_{12}]_i}{1 + K_{A6}[C_6]_i + K_{A12}[C_{12}]_i} - V_i \cdot d_C \cdot [C_j]$$

$$\frac{d(V_e \cdot [C_6]_e)}{dt} = \eta_6([C_6]_i - [C_6]_e)$$

$$\frac{d(V_e \cdot [C_{12}]_e)}{dt} = \eta_{12}([C_{12}]_i - [C_6]_e)$$

As before, we seek a system of equations for the rates of change of the molecular concentrations, but distinguish between whether we assume that transport is fast enough to remove from the model or not. We additionally augment each equation system with the double receiver module.

Slow Transport Model

We start by expanding the derivative on the left-hand sides, then defining $$\gamma := \frac{1}{V_i}\frac{dV_i}{dt}$$

as the specific growth rate, or dilution factor. Therefore, we obtain $$\frac{d[A]}{dt} = a_A \cdot f_{Pbad}(Ara) - (d_A + \gamma) \cdot [A] \quad (26a)$$

$$\frac{d[C_6]_i}{dt} = \frac{1}{V_i} \cdot \eta_6([C_6]_e - [C_6]_i) - \quad (26b)$$

$$d_{A6} \cdot \frac{[A][C_6]_i}{1 + K_{A6}[C_6]_i + K_{A12}[C_{12}]_i} - (d_C + \gamma) \cdot [C_j]$$

$$\frac{d[C_{12}]_i}{dt} = \frac{1}{V_i} \cdot \eta_{12}([C_{12}]_e - [C_{12}]_i) - \quad (26c)$$

$$d_{A12} \cdot \frac{[A][C_{12}]_i}{1 + K_{A6}[C_6]_i + K_{A12}[C_{12}]_i} - (d_C + \gamma) \cdot [C_j]$$

$$\frac{d[C_6]_e}{dt} = \frac{1}{V_e} \cdot \eta_6([C_6]_i - [C_6]_e) - \frac{1}{V_e} \cdot \frac{dV_e}{dt} \quad (26d)$$

$$\frac{d[C_{12}]_e}{dt} = \frac{1}{V_e} \cdot \eta_{12}([C_{12}]_i - [C_6]_e) - \frac{1}{V_e} \cdot \frac{dV_e}{dt} \quad (26e)$$

Two assumptions could be applied to $V_e$: (1) Ve is constant, or (2) $V_e = V_{tot} - V_i$, where $V_{tot}$ is a fixed total volume.

Fast Transport Model

If we assume that HSL transport is infinitely fast, then this results in the relations $[C_k]_e = [C_k]_i = [C_k]$ for k=6,12. However, we must be careful to maintain conservation of mass with respect to AiiA-mediated degradation. That is, we must scale the stoichiometric loss of HSL by the ratio of the extracellular and intracellular volumes. To see this, we write out equations for the new variables $[C_k]$ in terms of its constituent compartments.

$$\frac{d(V_i \cdot [A])}{dt} = V_i \cdot a_A \cdot f_{Pbad}(Ara) - V_i \cdot d_A \cdot [A] \tag{27a}$$

$$\frac{d(V \cdot [C_6])}{dt} = \frac{d(V_i \cdot [C_6]_i)}{dt} + \frac{d(V_e \cdot [C_6]_e)}{dt} = \tag{27b}$$

$$-V_i \cdot d_{A6} \cdot \frac{[A][C_6]}{1 + K_{A6}[C_6] + K_{A12}[C_{12}]} - V_i \cdot d_C \cdot [C_6]$$

$$\frac{d(V \cdot C_{12}])}{dt} = \frac{d(V_i \cdot [C_{12}]_i)}{dt} + \frac{d(V_e \cdot [C_{12}]_e)}{dt} = \tag{27c}$$

$$-V_i \cdot d_{A12} \cdot \frac{[A][C_{12}]}{1 + K_{A6}[C_6] + K_{A12}[C_{12}]} - V_i \cdot d_C \cdot [C_{12}]$$

By dividing out the volumes from the derivatives on the left-hand sides, and assuming that V(the total volume) is constant and $d_C$ is negligible, we obtain $$\frac{d[A]}{dt} = a_A \cdot f_{Pbad}(Ara) - (d_A + \gamma) \cdot [A] \tag{28a}$$

$$\frac{d[C_6]}{dt} = -V_i \cdot d'_{A6} \cdot \frac{[A][C_6]}{1 + K_{A6}[C_6] + K_{A12}[C_{12}]} \tag{28b}$$

$$\frac{d[C_{12}]}{dt} = -V_i \cdot d'_{A12} \cdot \frac{[A][C_{12}]}{1 + K_{A6}[C_6] + K_{A12}[C_{12}]} \tag{28c}$$

where $\gamma$ is the dilution factor as before and $d'_{Aj} = d_{Aj}/V$ for each j.

As AiiA concentrations are never observed, we can arbitrarily rescale [A], reducing the parametric complexity of the model. By substituting $[A] = k_A \cdot \alpha$, we obtain $$\frac{da}{dt} = f_{OLux}([C_6], [C_{12}]) - (d_A + \gamma)a \tag{29a}$$

$$\frac{d[C_6]}{dt} = -V_i \cdot \hat{d}_6 \cdot \frac{a \cdot [C_6]}{1 + K_{A6}[C_6] + K_{A12}[C_{12}]} \tag{29b}$$

$$\frac{d[C_{12}]}{dt} = -V_i \cdot \hat{d}_{12} \cdot \frac{a \cdot [C_{12}]}{1 + K_{A6}[C_6] + K_{A12}[C_{12}]} \tag{29c}$$

where $$\hat{d}_j = d'_j \cdot a_{Aj}.$$

ITEMS

The invention may further relate to the following items:

A method for determining one or more intrinsic properties of a DNA component, from a plurality of measurements obtained over a time period from a cell culture, with each cell comprising the DNA component and a reference promoter, wherein the DNA component is involved in transcription of one or more target signals and the reference promoter initiates transcription of a reference signal, wherein the plurality of measurements comprises: (i) measurements relating to the density of the cell culture over the time period; (ii) measurements relating to the amount of the reference signal in the cell culture over the time period; and (iii) measurements relating to the amount of the one or more target signals in the cell culture over the time period, the method comprising:

(a) estimating parameter values for a first mathematical model that describes cell culture density over time, by minimizing a measure of the difference between the first mathematical model output and the measurements relating to the density of the cell culture over the time period;

(b) estimating parameter values for a second mathematical model that describes the capacity of the cell culture to produce the reference signal over time, by minimizing a measure of the difference between the second mathematical model output and the measurements relating to the amount of the reference signal in the cell culture over the time period, wherein the second mathematical model additionally uses the parameter values estimated in (a);

(c) estimating parameters quantifying the intrinsic properties of the DNA component, by embedding these parameters within a third mathematical model that describes the production of the one or more target signals over time, and by minimizing a measure of the difference between the model outputs and the measurements relating to the amount of the one or more target signals, wherein the third mathematical model additionally uses the parameter values estimated in (b) by taking the second mathematical model to provide an estimate of the capacity of the cell culture to produce the one or more target signals over time.

The method as described above, wherein the DNA component is a promoter or an enhancer.

The method as described above, wherein the intrinsic property is the ability to recruit a polymerase enzyme or the ability to bind transcription factors.

The method as described above, wherein the sequences encoding the reference signal and the one or more target signals are within the chromosome of the cells in the cell culture.

The method as described above, wherein the cell culture is a culture of bacterial, yeast or mammalian cells.

The method as described above, wherein the one or more target signals are one or more target proteins.

The method as immediately described above, wherein the one or more target proteins are fluorescent proteins, wherein the reference signal is a different fluorescent protein, and wherein the measurements relating to the amount of the reference signal in the cell culture over the time period and the measurements relating to the amount of the one or more target signals in the cell culture over the time period are fluorescence measurements.

The method as described above, wherein the measurements relating to the density of the cell culture over the time period are optical densities.

The method as described above, wherein (a) to (c) are performed simultaneously or sequentially.

The method as described above, wherein parameters for the first mathematical model are selected from per capita culture growth rate, carrying capacity, and initial cell density.

The method as described above, wherein the first mathematical model is a logistic growth model.

The method as described above, wherein in (a) minimizing a measure of the difference is minimizing a sum of squared errors or the absolute differences between the first mathematical model and the measurements relating to the density of the cell culture over the time period.

The method as described above, wherein minimizing a measure of the difference in (a) uses a Nelder-Mead simplex algorithm.

The method as described above, wherein the second mathematical model models the capacity of the cell culture to produce the reference signal over the time period as a chemical reaction network.

The method as described above, wherein minimizing a measure of the difference in (b) uses a Markov chain Monte Carlo method.

The method as described above, wherein the method is performed with measurements (i), (ii) and (iii) obtained from a plurality of separate cell cultures, wherein the plurality of separate cell cultures have been subjected to different culture conditions, wherein (a), (b) and (c) are performed for each separate cell culture, wherein in (b) variations in the capacity to produce the reference signal over time between the plurality of cell cultures are quantified and used in (c) to factor out equivalent variations in the functioning of the DNA component and the one or more target signals.

The method as described above, further comprising obtaining the measurements of (i), (ii) and (iii).

The method as described above, further comprising a step of adapting the DNA component in vitro based on the results of step (c).

The invention further provides a method of optimizing expression of at least one gene comprised in a genetic circuit, wherein the genetic circuit further comprises a DNA component which is involved in transcription of the at least one gene, wherein the method comprises: (1) determining one or more intrinsic properties of the DNA component using the method as described above; (2) using the one or more intrinsic properties of the DNA component determined in (1) to simulate expression of the at least one gene from the genetic circuit in at least two different arrangements of the genetic circuit; (3) selecting the arrangement in (2) that results in optimal expression of the at least one gene; and (4) making the arrangement of the genetic circuit selected in step (3).

The invention further provides a computer program product embodied on a computer readable storage and comprising code which is configured so as to perform the operations of the method described above when run on a computer system.

Other variants may become apparent to a person skilled in the art once given the disclosure herein. The scope of the present disclosure is not limited by the above-described embodiments but only by the accompanying claims.

The invention claimed is:

1. A method for determining an intrinsic property of a DNA component involved in transcription of a target signal, the method comprising:
   accessing a plurality of measurements obtained over a time period from a cell culture, wherein each cell in the cell culture comprises the DNA component, and wherein the plurality of measurements comprises a first measurement relating to an amount of the target signal in the cell culture over the time period and a second measurement relating to a density of the cell culture of the time period;
   estimating parameters quantifying the intrinsic property of the DNA component by:
      embedding the estimated parameters within a mathematical model that describes a production of the target signal over the time period; and
      minimizing a measure of a difference between outputs of the mathematical model and the first measurement;
   estimating parameter values for a second mathematical model that describes cell culture density over time by minimizing a measure of a difference between an output of the second mathematical model and the second measurement; and
   based on the estimated parameters and the estimated parameter values, identifying the intrinsic property.

2. The method according to claim 1, wherein each cell in the cell culture further comprises a reference promoter that initiates transcription of a reference signal.

3. The method according to claim 2, wherein the plurality of measurements comprises: measurements relating to amount of the reference signal in the cell culture over the time period.

4. The method according to claim 3, wherein the DNA component is an enhancer, and wherein the intrinsic property is an ability to recruit a polymerase enzyme.

5. The method according to claim 3, further comprising:
   estimating parameter values for a third mathematical model that describes a capacity of the cell culture to produce the reference signal over time, by minimizing a measure of a difference between an output of the third mathematical model and the measurements relating to the amount of the reference signal in the cell culture over the time period; and
   based on the estimated parameters for the second mathematical model, the estimated parameters of the third mathematical model, and the estimated parameter values, identifying the intrinsic property.

6. The method according to claim 5, wherein the third mathematical model models the capacity of the cell culture to produce the reference signal over the time period as a chemical reaction network.

7. The method according to claim 1, wherein minimizing the measure of the difference between outputs of the mathematical model and the first measurement uses a Markov chain Monte Carlo method.

8. The method according to claim 1, wherein the DNA component is a promoter, and wherein the intrinsic property is an ability to bind transcription factors.

9. The method according to claim 1, wherein the cell culture is a culture of bacterial, yeast or mammalian cells.

10. The method according to claim 1, wherein the target signal is a target protein.

11. The method according to claim 10, wherein the target protein is a fluorescent protein, and wherein the first measurement relating to the amount of the target signal in the cell culture over the time period are fluorescence measurements.

12. The method according to claim 1, further comprising:
   obtaining the plurality of measurements over the time period from the cell culture; and
   adapting the DNA component in vitro based on the one or more intrinsic properties.

13. A system for determining an intrinsic property of a DNA component involved in transcription of a target signal, the system comprising:
   a processor; and
   a memory comprising computer-executable instructions that, when executed by the processor, cause the processor to perform the following operations:
      accessing a plurality of measurements obtained over a time period from a cell culture, wherein each cell in the cell culture comprises the DNA component, and wherein the plurality of measurements comprises a first measurement relating to an amount of the target signal in the cell culture over the time period and a second measurement relating to a density of the cell culture of the time period;

estimating parameters quantifying the intrinsic property of the DNA component by:

embedding the estimated parameters within a mathematical model that describes a production of the target signal over the time period; and minimizing a measure of a difference between outputs of the mathematical model and the first measurement;

estimating parameter values for a second mathematical model that describes cell culture density over time by minimizing a measure of a difference between an output of the second mathematical model and the second measurement; and based on the estimated parameters and the estimated parameter values, identifying the intrinsic property.

14. The system according to claim 13, wherein each cell in the cell culture further comprises a reference promoter that initiates transcription of a reference signal.

15. The system according to claim 14, wherein the plurality of measurements comprises: measurements relating to an amount of the reference signal in the cell culture over the time period.

16. The system according to claim 14, wherein the memory further comprises computer-executable instructions that, when executed by the processor, cause the processor to perform one or more of the following operations:

estimating parameter values for a third mathematical model that describes a capacity of the cell culture to produce the reference signal over time, by minimizing a measure of a difference between an output of the third mathematical model and the measurements relating to the amount of the reference signal in the cell culture over the time period.

17. A computer-readable storage device comprising computer-executable instructions for determining an intrinsic property of a DNA component involved in transcription of a target signal, the computer-executable instructions when executed by a processor, cause the processor to perform the following operations:

accessing a plurality of measurements obtained over a time period from a cell culture, wherein each cell in the cell culture comprises the DNA component, and wherein the plurality of measurements comprises a first measurement relating to an amount of the target signal in the cell culture over the time period and a second measurement relating to a density of the cell culture of the time period;

estimating parameters quantifying the intrinsic property of the DNA component by:

embedding the estimated parameters within a mathematical model that describes a production of the target signal over the time period; and minimizing a measure of a difference between outputs of the mathematical model and the first measurement;

estimating parameter values for a second mathematical model that describes cell culture density over time by minimizing a measure of a difference between an output of the second mathematical model and the second measurement; and based on the estimated parameters and the estimated parameter values, identifying the intrinsic property.

18. The computer-readable storage device according to claim 17, wherein each cell in the cell culture further comprises a reference promoter that initiates transcription of a reference signal.

19. The computer-readable storage device according to claim 18, wherein the DNA component is an enhancer, and wherein the intrinsic property is an ability to recruit a polymerase enzyme.

20. The computer-readable storage device according to claim 17, wherein the computer-readable medium further comprises computer-executable instructions that, when executed by the processor, cause the processor to perform the following operations:

estimating parameter values for a third mathematical model that describes cell culture density over time, by minimizing a measure of a difference between an output of the third mathematical model and measurements relating to a density of the cell culture over the time period.

* * * * *